United States Patent [19]
Luna et al.

[11] Patent Number: 5,985,608
[45] Date of Patent: Nov. 16, 1999

[54] ACTIN-BINDING POLYPEPTIDES AND NUCLEIC ACIDS ENCODING THE SAME

[75] Inventors: Elizabeth J. Luna, Shrewsbury; Kersi N. Pestonjamasp; Robert K. Pope, both of Worcester; Julia D. Wulfkuhle, Shrewsbury, all of Mass.

[73] Assignee: University of Massachusetts, Boston, Mass.

[21] Appl. No.: 08/962,284

[22] Filed: Oct. 31, 1997

[51] Int. Cl.$^6$ .................................................. C12N 15/00
[52] U.S. Cl. ...................... 435/69.1; 435/320.1; 435/325; 435/252.3; 536/23.5; 536/23.1; 530/350
[58] Field of Search ................................. 435/69.1, 320.1, 435/325, 252.3; 536/23.5, 23.1; 530/350

[56] References Cited

PUBLICATIONS

Arpin et al., "Sequence of Human Villin: a Large Duplicated Domain Homologous with Other Actin–severing Proteins and a Unique Small Carboxy–terminal Domain Related to Villin Specificity," *The Journal of Cell Biology*, 107:1759–1766, 1988.
Hofmann et al., "The 100 kDa F–actin capping protein of *Dietyostelium amoebae* is a villin prototype ('protovillin')", *FEBS Letters*, 328:71–76, 1993.
Pringault et al., "A human villin cDNA clone to investigate the differentiation of intestinal and kidney cells in vivo and in culture", *The EMBO Journal*, 5:3119–3124, 1986.
Pestonjamasp et al., J.Cell Biol. 139(5): 1255–1269, Dec. 1997.
Callard et al, The Cytokine FactsBook, Academic Press Ltd, 1994, p. 31).
Chia et al. "Direct Binding of F–Actin to Ponticulin, an Integral Plasma Membrane Glycoprotein," *Cell Motility and the Cytoskeleton*, 18:164–179, 1991.
Chia et al., "The Integral Membrane Protein, Ponticulin, Acts as Monomer in Nucleating Actin Assembly, " *The Journal of Cell Biology*, 120:909–922, 1993.
Luna et al., "Actin–binding Membrane Proteins Identified by F–actin Blot Overlays, " *Cytoskeletal Regulation of Membrane function*, pp. 1–18, 1997.
Mandai et al., "Afadin: A Novel Actin Filament–binding Protein with one PDZ Domain Localized at Cadherin–based Cell–to–Cell Adherens Junction," *The Journal of Cell Biology*, 139:517–528, 1997.
Pestonjamasp et al., "Moesin, Ezrin, and p205 Are Actin–binding Proteins Associated with Neotrophil Plasma Membranes," *Molecular Biology of the Cell*, 6:247–259, 1995.
Villin., Genbank Sequence Database Accession No. 138530, Jul. 1, 1989.
Villin., Genbank Sequence Database Accession No. 138529, Aug. 1, 1990.
Mus musculus villin protein mRNA, complete cds., Genbank Sequence Database Accession No. M98454, Aug. 12, 1992.
Protovillin, Genbank Sequence Database Accession No. 549325, Jun. 1, 1994.
vh15d12.rl Soares mouse mammary gland nbMMG Mus musculus cDNA clone 875543 5', similar to SW:VIL1HUMAN P09327 Villin.; mRNA sequence, Genbank Sequence Database Accession No. AA475482, Jun. 18, 1997.
Gelsolin, Genbank Sequence Database Accession No. 121117, Oct. 1, 1994.
mj27f02.rl Soares mouse embryo NbME13.5 14.5 Mus musculus cDNA clone 477339 5', mRNA sequence, Genbank Sequence Database Accession No. AA048260, Sep. 9, 1996.
mj21c08.rl Life Tech mouse embryo 13 5dpc 10666014 Mus musculus cDNA clone 554222 5', mRNA sequence, Genbank Sequence Database Accession No. AA103419, Oct. 29, 1996.
Caenorhabditis elegans cosmid C10H11, Genbank Sequence Database Accession No. U388311, Feb. 7, 1997.
mp67e12.rl Soares 2NbMT Mus musculus cDNA clone 574318 5' similar to SW:VIL1HUMAN P09327 VILLIN.; mRNA sequence, Genbank Sequence Database Accession No. AA111215, Feb. 17, 1997.
z146ell.rl Soares pregnant uterus NbHPU Homo sapiens cDNA clone 505004 5', mRNA sequence, Genbank Sequence Database Accession No. AA151268, May 19, 1997.

*Primary Examiner*—Lorraine Spector
*Assistant Examiner*—Eliane Lazar-Wesley
*Attorney, Agent, or Firm*—Fish & Richardson P.C.

[57] ABSTRACT

The invention relates to supervillin polypeptides, nucleic acid molecules encoding supervillin, and uses thereof. Supervillin is related to the actin-binding proteins villin and gelsolin.

16 Claims, 16 Drawing Sheets

```
   1  MKRKERIARR  LEGIETDTQP  ILLQSCTGLV  THRLLEEDTP  RYMRATDPAS
  51  PHIGRSNEEE  ETSDSSLEKQ  TRSKQCTETS  GIHADSPYSS  GIMDTQSLES
 101  KAERIARYKA  ERRRQLAEKY  GLTLDPEADS  ETPSRYSRSR  KDPEAAEKRG
 151  VRSERSAKSS  RDAGSSYSRT  ELSGLRTCVA  ESKDYGLHRS  DGVSDTEVLL
 201  NAENQRRGQE  PSATGLARDL  PLAGEVSSSF  SFSGRDSALG  EVPRSPKAVH
 251  SLPSPSPGQP  ASPSHSTSDL  PLPAEARARS  TSNSEMPAAE  DEEKVDERAR
 301  LSVAAKRLLF  REMEKSFDEK  SVPKRRSRNA  AVEQRLRRLQ  DRSHTQPVTT
 351  EEVVIAATLQ  ASAHQKALAR  DQTNESKDSA  EQGEPDSSTL  SLAEKLALFN
 401  KLSQPVSKAI  STRNRLDMRQ  RRMNARYQTQ  PVTLGEVEQV  QSGKLMAFSP
 451  TINTSVSTVA  STVPPMYAGN  LRTKPLPDDS  FGATEQKFAS  SLENSDSPVR
 501  SILKSQGWQP  SVEGAGSKAM  LREFEETERK  GGLTGGDGGV  TKYGSFEEAE
 551  LSYPVLSRVR  EGDNHKEAIY  ALPRKGSLEL  AHPPIAQLGD  DLKEFSTPKS
 601  TMQASPDWKE  RQLFEEKVDL  ENVTKRKFSL  KAAEFGEPTS  EQTGAAAGKP
 651  AAPTATPVSW  KPQDPSEQPQ  EKRYQSPCAM  FAAGEIKAPA  VEGSLDSPSK
 701  TMSIKERLAL  LKKSGEEDWR  NRLNRKQEYG  KASITSSLHI  QETEQSLKKK
 751  RVTESRESQM  TIEERKHLIT  VREDAWKTRG  KGAANDSTQF  TVAGRMVKRG
 801  LASPTAITPV  ASPVSSKARG  TTPVSRPLED  IEARPDMQLE  SDLKLDRLET
 851  FLRRLNNKVG  GMQETVLTVT  GKSVKEVMKP  DDDETFAKFY  RSVDSSLPRS
 901  PVELDEDFDV  IFDPYAPRLT  SSVAEHKRAV  RPKRRVQASK  NPLKMLAARE
 951  DLLQEYTEQR  LNVAFVESKR  MKVEKLSANS  SFSEVTLAGL  ASKENFSNVS
1001  LRSVNLTEQN  SNNSAVPYKK  LMLLQVKGRR  HVQTRLVEPR  APSLNSGDCF
1051  LLLSPHHCFL  WVGEFANVIE  KAKASELASL  IQTKRELGCR  ATYIQTVEEG
1101  INTHTHAAKD  FWKLLGGQAS  YQSAGDPKED  ELYETAIIET  NCIYRLMDDK
1151  LVPDDDYWGK  IPKCSLLQSK  EVLVFDFGSE  VYVWHGKEVT  LAQRKIAFQL
1201  AKHLWNGTFD  YENCDINPLD  PGECNPLIPR  KGQGRPDWAI  FGRLTEHNET
1251  ILFKEKFLDW  TELKRPNEKN  ASELAQHKDD  ARAEVKPYDV  TRMVPVPQTT
1301  AGTVLDGVNV  GRGYGLVEGD  DRRQFEIASI  SVDVWHILEF  DYSRLPKQSI
1351  GQFHEGDAYV  VKWKFIVSTA  VGSRQKGEHS  VRVAGKEKCV  YFFWQGRQST
1401  VSEKGTSALM  TVELDEERGA  QVQVLQGKEP  PCFLQCFQGG  MVVHSGRREE
1451  EEENTQSEWR  LYCVRGEVPV  EGNLLEVACH  CSSLRSRTSM  VVLNVHKALI
1501  YLWHGCKAQA  HTKEVGRTAA  NKIKDQCPLE  AGLHSSSKVT  IHECDEGSEP
1551  LGFWDALGRR  DRKAYDCMLQ  DPGNFNFTPR  LFILSSSSGD  FSATEFMYPA
1601  RDPSVVNSMP  FLQEDLYSAP  QPALFLVDNH  HEVYLWQGWW  PIENKITGSA
1651  RIRWASDRKS  AMETVLQYCR  GKNLKKPPPK  SYLIHAGLEP  LTFTNMFPSW
1701  EHREDIAEIT  EMDTEVSNQI  TLVEDVLAKL  CKTIYPLADL  LARPLPEGVD
1751  PLKLEIYLTD  EDFEFALDMT  RDEYNALPAW  KQVNLKKAKG  LF*
```

(SEQ ID NO: 4)

FIG. 1

| FIG. 4A |
|---|
| FIG. 4B |
| FIG. 4C |
| FIG. 4D |

FIG. 4

| FIG. 5A |
|---|
| FIG. 5B |

FIG. 5

```
A.A.                                                                                                                    N.A.
     TCGGCGGGAAGCGGCGATCCTGCCACCCGGAGGTGTGAAGAGCCCGGTAGATTCTGGCTACATTGGAGAGATTGTTGCTTTCTAAAACTG                          -361
     AAGGAGAAGCCCATGAAGACAGATGTGATTCTCACTGAGTTTGACTAGCGCAGAGTTCAAGTGGATGGCCTTGAGGACT                                    -271
     TGAAAAGCTGAGATATGATTCCCAGCTGGATTCAACATGATTTAAATATCGCGTTAAGATTTCAACAAGAAAAACTTA                                     -181
     AGCTTCCTTGGATTCCAAGCTCAAAGGAAGAATTTCAAGCTTCAGAAGGAGTTCTCACTGCAGAATTAAGACAAATCTTGAACCAAAGAACAGCTCGCTAACCACGA          -91
     AGAGGAATCGATGCTCAGCTTTTAGTTGCACTTCCTGAAGGGATTGAAAATGACACTCAGCCCATCCTCTTGCAGAGCTGCACAGGATTGTG                          -1
     ATGAAAAGAAAAGAAAGAATTGCCAGGCGGATCCTGAGGAAGACACACCCCTGCCAGCCCCACATGGCCGATCAAATGAAGAGGAG                                90
      M  K  R  K  E  R  I  A  R  R  L  E  G  I  E  N  D  T  Q  P  I  L  L  Q  S  C  T  G  L  V
  1
     ACTTCACCCGCTGCTGAGGAGACACCCCTCGATACATGAGAGCCAGGACCCTGCCAGCCCCACATGGCCGATCAAATGAAGAGGAG                               180
      T  H  R  L  L  E  E  D  T  P  R  Y  M  R  A  S  D  P  A  S  P  H  I  G  R  S  N  E  E  M
 31
     GAAACTTCTGATTCTTCTAGAAAAGCAAACTCGATCCAAATACTGCACAGAAACCTCCGTGTCCACGGTGACTCACCCTATGGTTCG                               270
      E  T  S  D  S  S  L  E  K  Q  T  R  S  K  Y  C  T  E  T  S  G  V  H  G  D  S  P  Y  G  S
 61
     GGTACCATGGACACCCACAGTCTGGAGTCCAAAGCCGAAAGAATTGCAAGGTACAAAGCAGAAGAAGGCGACAGCTGGCAGAGAGAAGTAT                           360
      G  T  M  D  T  H  S  L  E  S  K  A  E  R  I  A  R  Y  K  A  E  R  R  Q  L  A  E  K  Y
 91
     GGGCTGACTCTGGATCCCGAGGCCGACTCCGAGTATTTATCCGCTATACCAAGTCCAGGAAGGAGCCTGATGCTGTCGAGAAGCGGGGA                             450
      G  L  T  L  D  P  E  A  D  S  E  Y  L  S  R  Y  T  K  S  R  K  E  P  D  A  V  E  K  R  G
121
     GGAAAAGTGACAAACAGGAAGAGTCAAGCAGAGATGCGAGTTCTGTACCCCGGGAGACCGAGACGATGGGCTCAGGACCTGTGCCGGT                              540
      G  K  S  D  K  Q  E  E  S  S  R  D  A  S  S  L  Y  P  G  T  E  T  M  G  L  R  T  C  A  G
151
     GAATCCAAGGACTATGCCCTCCATGCGGGTGACGGCTCTCTCCGACCCGAGAGTGCTGCTGAACATAGAAAACAAAGACGAGTCAAGAG                             630
      E  S  K  D  Y  A  L  H  A  G  D  G  S  S  D  P  E  V  L  L  N  I  E  N  Q  R  R  G  Q  E
181
     CTGAGTGCCACCCGGCTCCCCCAAGCACGACCTGTCCCCCAGCAGCCCACAGTCCTCCTGCAGCAGCCCCTTTGTGACCCCTCCTTCTTCTGGGCGAGACTCCTTCACT         720
      L  S  A  T  R  Q  A  H  D  L  S  P  A  A  E  S  S  T  F  S  S  S  G  R  D  S  S  F  T
211
     GAAGTGCCACGGTCCCCCAAGCACTGCACTTCACATTCAGAAACGCCAACTGTCAGATGATGAACAAAAATGTTCAAAGCGACGCTCAAGCCAGCGTCGAGCGC              810
      E  V  P  R  S  P  K  K  H  A  H  S  S  L  Q  Q  A  A  S  R  S  P  S  F  G  D  D  P  Q  L  S
241
     CCTGAGGCCCGACCCAGTGCACTTGCACTTCAGGAGATGGAAAAATCTTTGATGAACAAAATGTTCAAAGCGACGCTCAAGCTGTGGAG                              900
      P  E  A  R  P  R  C  T  S  H  S  E  T  P  T  V  D  D  E  E  K  V  D  E  R  A  K  L  S  V
271
     GCCGCCAAGAGGTTGCTTTTCAGGGAGATGGAAAAATCTTTGATGAACAAAATGTTCAAAGCGACGCTCAAGCTGTGGAG                                       990
      A  A  K  R  L  L  F  R  E  M  E  K  S  F  D  E  Q  N  V  P  K  R  R  S  R  N  T  A  V  E
301
     CAGAGGCTACGCCGTCTGCAGGACGACAGGTCCCTGACCCAGCCCATCACCACTGAAGAGGTTGTCATCGCAGCCACATTGCAGGCCTCTGCT                          1080
      Q  R  L  R  R  L  Q  D  R  S  L  T  Q  P  I  T  T  E  E  V  V  I  A  A  T  L  Q  A  S  A
331
     CACCAAAAGGCCTTAGCCAAGGACCAGACCAATGAGGGCAAAGAGCTTGCTGAGCAAGGAGAACCTGATTCCTCCACTCTAAGCTTGGCC                             1170
      H  Q  K  A  L  A  K  D  Q  T  N  E  G  K  E  L  A  E  Q  G  E  P  D  S  S  T  L  S  L  A
361
     GAAAAGTTGGCCTTGTTTAACAAATTGTCCCAGCCAGTCTCAAAAGCGATTTCTACCCGGAACAGAATAGACACGAGACAGAGGAGAATG                             1260
      E  K  L  A  L  F  N  K  L  S  Q  P  V  S  K  A  I  S  T  R  N  R  I  D  T  R  Q  R  R  M
391
     AACGCTCGCTATCAAACTCAGCCAGTCACACTGGGAGAGTGGAGCAGGTGGAGCAGTGGAGTCGAAAGCTCATTCCTTTCTCACCTGCCGTGAAC                        1350
      N  A  R  Y  Q  T  Q  P  V  T  L  G  E  V  E  Q  V  Q  S  G  K  L  I  P  F  S  P  A  V  N
421
     ACATCAGTGCTCTACCGTAGCATCCACCGGTTGCTCCAATGTATGTACGCGCCCATGTATGCGGAGATCTTCGCACAAAGCCACCTCTTGACCACAAAGCCACCTCCTCTTGACCACAATGCAAGTGCC  1440
      T  S  V  S  T  V  A  S  T  V  A  P  M  Y  A  G  D  L  R  T  K  P  P  L  D  H  N  A  S  A
451
```

FIG. 4A

```
481  ACTGACTATAAGTTTCTCTTCAATAGAAAATTCGGACTCTCCAGTTAGAAGCATTCTGAAATCGCAAGCTTGGCAGCCTTTGGTAGAG   1530
      T  D  Y  K  F  S  S  S  I  E  N  S  D  S  P  V  R  S  I  L  K  S  Q  A  W  Q  P  L  V  E

511  GGTAGCGAGAACAAGGGAATGTTGAGAATATGAGAGAGTTCAAGAGAGCTTTGACAGGTCGAGACAGTGGGATGGAGAAGTAT        1620
      G  S  E  N  K  G  M  L  R  E  Y  G  E  T  E  S  K  R  A  L  T  G  R  D  S  G  M  E  K  Y

541  GGGTCCTTTGAGGAAGCAGAAGCATCCTACCCCATCCTGAACAGAGCCAGGGAAGGAGACAGCCATAAGGAGAATCTAAATATGCTGTTCCC   1710
      G  S  F  E  E  A  S  Y  P  I  L  N  R  A  R  E  G  D  S  H  K  E  S  K  Y  A  V  P

571  AGAAGAGAAGCCTGAACGGGCGAACCCCCCATCCACCACTCGGGGATGAACCGAAGGAATTTTCCATGGCTAAAATGAATGCACAA    1800
      R  R  G  S  L  E  R  A  N  P  P  I  T  H  L  G  D  E  P  K  E  F  S  M  A  K  M  N  A  Q

601  GGAAACTTGGACTTGAGGGACAGGCTGCCCTTTGAAGAAGAAGTGGAGTGGAGAATGTTATGAAAAGGAAGTTTTCACTAAGAGCGGCA   1890
      G  N  L  D  L  R  D  R  L  P  F  E  E  K  V  E  V  E  N  V  M  K  K  F  S  L  R  A  A

631  GAGTTCGGGGAGCCCACTTCCAGCAGACGGGACAGCTGTCTGGGAAAACTATTGCTCAAACCACAGCCCCCGTGTCTGGAAGCCCCAG    1980
      E  F  G  E  P  T  S  E  Q  T  G  T  A  A  G  K  T  I  A  Q  T  T  A  P  V  S  W  K  P  Q

661  GATTCTTGACTCACCCAGCAGAGAAGCTCTGCAAGAATCCATGTGCGATGTTTGCTGTCTGAGAGATCAAAACGCCGACAGGGGAGGGC   2070
      D  S  S  E  Q  P  Q  E  K  L  C  K  N  P  C  A  M  F  A  A  G  E  I  K  T  P  T  G  E  G

691  CTTCTTGACTCCACCCAGCAAAACCATGTCTATTAAAGAACGATTGGCACTGTTGAAGAAAAAGCGGGAGGAAGATTGGAGAAACAGACTC  2160
      L  L  D  S  P  S  K  T  M  S  I  K  E  R  L  A  L  L  K  K  S  G  E  E  D  W  R  N  R  L

721  AGCAGGAGGCAGGAGGGCGGCAAGGCGCCCAGCCTGCACACCCAGGAAGCAGGGCGGTCCCTCATCAAGAAGCGGGTCACAGAA        2250
      S  R  R  Q  E  G  G  K  A  P  A  S  L  H  T  Q  E  A  G  R  S  L  I  K  K  R  V  T  E

751  AGTCGAGAGAGCCAAATGACGATTGAGGAAGCAGCTCATCATCGTGAGAGAGAAGCCTGGAAGACGAGAGGAGGCAGGAGAGCGGCC    2340
      S  R  E  S  Q  M  T  I  E  E  R  K  Q  L  I  T  V  R  E  E  A  W  K  T  R  G  R  G  A  A

781  AACGACTCGACCCAGTTCACTCAGTTTGTTGCTGGCAGGATGGTGAAGAAAGGTTGGCGTGCACCTACTGCCATAACCCCAGTAGCCTTCAGCCATT 2430
      N  D  S  T  Q  F  T  V  A  G  R  M  V  K  K  G  L  A  S  P  T  A  I  T  P  V  A  S  A  I

811  TGCGGTAAAACAAGAGGCCAGATGATGAAGCCTGAAGATATCGAAGCCAGAGCCAGATATGCAGTTAGAATCGGACCTGAAG         2520
      C  G  K  T  R  G  T  T  P  V  S  K  P  L  E  D  I  E  A  R  P  D  M  Q  L  E  S  D  L  K

841  TTGGACAGGCTGGAAACCTTTCTAAGAAGCTGAATAACAAAGTTGGCGGGATGCACGAAACGGTGCTCACTGTCACCGGCAAATCTGTG    2610
      L  D  R  L  E  T  F  L  R  R  L  N  N  K  V  G  G  M  H  E  T  V  L  T  V  T  G  K  S  V

871  AAGGAGGTGATGAAGCCAGATGATGAAGCCTTTGCCAAATTTTACCGCGGTGATTATATATGCCAAGAAGTCCTGTGGAGATG        2700
      K  E  V  M  K  P  D  D  E  T  F  A  K  F  Y  R  S  V  D  Y  N  M  P  R  S  P  V  E  M

901  GATGAGGACTTCGATGTCATTTTCGATCCTTATGCACCCAAAATTGACGTCTTCCGTGGCCAGTCACGGGCACAAGCGGGCAGTTAGGCCAAGCGC  2790
      D  E  D  F  D  V  I  F  D  P  Y  A  P  K  L  T  S  S  V  A  E  H  K  R  A  V  R  P  K  R
```

```
1441  TCGGGGAGGCGGGAAGAGGAAGAGAAATGTGCAAAGTGAGTGGGCTGTACTGCTGCGTCGTGAGAGGTGCCCGTGAAGGAATTG   4410
      S  G  R  R  E  E  E  E  N  V  Q  S  E  W  R  L  Y  C  V  R  G  E  V  P  V  E  G  N  L

1471  CTGGAAGTGGCCTGTCACTGCTGTAGCAGCCTGAGTCCAGAACTTCCATGTGGTGCTTAACGTCAACAAGGCCCTCATCTACCTGTGGCAC   4500
      L  E  V  A  C  H  C  S  S  L  R  S  R  T  S  M  V  V  L  N  V  N  K  A  L  I  Y  L  W  H

1501  GGATGCAAAGCCCAGGCCCACACGAAGGAGGTCGGAAGGACCGCTGCGAACAAGATCAAGGAACAATGTCCCCTGGAAGCAGGACTGCAT   4590
      G  C  K  A  Q  A  H  T  K  E  V  G  R  T  A  A  N  K  I  K  E  Q  C  P  L  E  A  G  L  H

1531  AGTAGCAGCAAAGTCACAATACACGAGTGTGATGAAGGCTCCGAGCCACTCGGATTCTGGGATGCCTTAGGAAGGAGAGACAGAAAGCC   4680
      S  S  S  K  V  T  I  H  E  C  D  E  G  S  E  P  L  G  F  W  D  A  L  G  R  R  R  D  R  K  A

1561  TACGATTGCATGCTTCAAGATCCTGGAAGTTTTAACTTCGCCCCGCTGTTCATCCTCGTCTTCTGGGATTTTGCAGCCACA   4770
      Y  D  C  M  L  Q  D  P  G  S  F  N  F  A  P  R  L  F  I  L  S  S  G  D  F  A  A  T

1591  GAGTTTGTGTACCCTGCCCGAGCCCCTCTGTGGTCAGTTGTACTCTGGCAAGGCTGGTGGCCCATGCAAGGCTGTACAGGCGGCCCCAGCCAGCACTT   4860
      E  F  V  Y  P  A  R  A  P  S  V  V  S  S  M  P  F  L  Q  E  D  L  Y  S  A  P  Q  P  A  L

1621  TTCCTTGTTGACAATCACCACGAGTGTACTCTGGCAAGCTGGATTGCTGTCCAGTACTGCAAGGCTACTGGGGCTGGTGGCCCATCGCAAGGGAAAAAATCAAGAACAAGATCACTGGTTCCGCCCATCCGCTGG   4950
      F  L  V  D  N  H  H  E  V  Y  L  W  Q  G  W  W  P  I  E  N  K  I  T  G  S  A  R  I  R  W

1651  GCCTCCGACCGCTCGAGCCCCTGACATTCACCAATGTTCCCAGCTGCAAGCTCTTAGCACGAAGCTCTGTAGCACGAAGATGGAAAGCGCCCCAAGTCTCTTACCTTATC   5040
      A  S  D  R  K  S  A  M  E  T  V  L  Q  Y  C  K  G  K  N  L  K  K  P  A  P  K  S  Y  L  I

1681  CACGCTGGTCTGGAGCCCCTGACATTCACCAATGTTCCCAGCTGGGAGCACAGAGACATCGCTGAGATCACAGAGATGGACACG   5130
      H  A  G  L  E  P  L  T  F  T  N  M  F  P  S  W  E  H  R  E  D  I  A  E  I  T  E  M  D  T

1711  GAAGTTTCCAATCAGATCACCCTCGTGGAAGACGTCTTAGCACAAGCTCTGTAAACCATTTACCCGCTGGCCGACCTCCTGGCCAGGCCA   5220
      E  V  S  N  Q  I  T  L  V  E  D  V  L  A  K  L  C  K  T  I  Y  P  L  A  D  L  L  A  R  P

1741  CTCCCGAGGGGTCGATCCTCTGAAGCTTGAGATCTATCTCACCGACGAAGACTTCGAGTTTGCACTAGACATGACGAGGGATGAATAC   5310
      L  P  E  G  V  D  P  L  K  L  E  I  Y  L  T  D  E  D  F  E  F  A  L  D  M  T  R  D  E  Y

1771  AACGCCCTGCCCGCCTGGAAGCAGGTGAACCTGAAGAAAGCAAAGGCCTGTTGAGTGGGAGACCCCAGGAGGCCTCACGGTCACG   5400
      N  A  L  P  A  W  K  Q  V  N  L  K  K  A  K  G  L  F  *  (SEQ ID NO: 2)

TCCAACAACACCACTGCCACCAGGGAAATGGATATATATTTTTGGACTGGTCTGTGTTTTTCACAAAGTATTTTTCAATCAGAGTTTTCAGAACC   5490
      TGACATTGTTAAAGATACTGCTTGTCCCGGAGTTGTGTATTTTGTAAATGTTCAAGGGAACTGTTTTGGAAAACTTCTTTCCACCATTCAGG   5580
      AGGTTATCAGAATTAATAAAAGTATCGTTATGTGCACTTAAGCCGCAGCTGCTTAGTGTTAGTTTTGATAGTTTGTGATTCTAAAATATATATTTATATAAAC   5670
      GCCTTTTTTTTTTTTGAAGCAGTGTATTTAACAAGCAATATGTTATTCATTTCAAGATTTCACTTTGGTGTCAAAATAACATGAAAAGGTA   5760
      ACCATATAAGTCAAATATGTATTTAACAAGCAATATGTTATTCATTTCAAGATTTCACTTTGGTGTCAAAATAACATGAAAAGGTA   5850
      GATGAGTTGCTTCTGTTGAATTAGCTCTGCCACCAATATGTATCTCATTACACGTTTGAAATGTTTCCTGACGATTAGTATGACTT   5940
      GTTCTGAGTACTGCTTCCGGTGCTAAAAATGTAGTGCCTTGTTTTTATGCATACAAAGAATTTGTACTTATACACGTTTATATACACACATTGCTTAAGTTTGCTCTGCATTTTTGATGATGGTT   6030
      ACCTTAATAATCTCCCCAAAATTTTACTCCAAATAGTCAAATAAAAACATCTCAATTTCTAATACCGGTTGTAAACAAACAGTACACATGTC   6120
      TGGAACATTATCTACCAATTTTACTCCAAATAGTCAAATAAAAACATCTCAATTTCTAATACCGGTTGTAAACAAACAGTACACATGTC   6210
      ATTTTGTGATATAGGACTCCCAAATAAAAGTATCAGAATAAACACCAACAATTAACTGG   6268

(SEQ ID NO: 1)
```

```
           BOVINE  1  MKRKERIARR  LEGIETDTQP  ILLQSCTGLV  THRLLEEDTP  RYMRATDPAS  PHIGRSNEEE  ETSDSSLEKQ
           HUMAN      MKRKERIARR  LEGIENDTQP  ILLQSCTGLV  THRLLEEDTP  RYMRASDPAS  PHIGRSNEEE  ETSDSSLEKQ

71  TRSKQCTETS  GIHADSPYSS  GIMDTQSLES  KAERIARYKA  ERRRQLAEKY  GLTLDPEADS  ETPSRYSRSR
                      TRSKYCTETS  GVHGDSPYGS  GTMDTHSLES  KAERIARYKA  ERRRQLAEKY  GLTLDPEADS  EYLSRYTKSR

141  KDPEAAEKRG  VRSERSAKSS  RDAGSSYSRT  ELSGLRTCVA  ESKDYGLHRS  DGVSDTEVLL  NAENQRRGQE
                      KEPDAVEKRG  GKSDKQEESS  RDASSLYPGT  ETMGLRTCAG  ESKDYALHAG  DGSSDPEVLL  NIENQRRGQE

211  PSATGLARDL  PLAGEVSSSF  SFSGRDSALG  EVPRSPKAVH  SLPSPSPGQP  ASPSHSTSDL  PLPAEARARS
                      LSATRQAHDL  SPAAESSSTF  SFSGRDSSFT  EVPRSPKHAH  SSSLQQA---  ASRSPSFGDP  QLSPEARPRC

281  TSNSEMPAAE  DEEKVDERAR  LSVAAKRLLF  REMEKSFDEK  SVPKRRSRNA  AVEQRLRRLQ  DRSHTQPVTT
                      TSHSETPTVD  DEEKVDERAK  LSVAAKRLLF  REMEKSFDEQ  NVPKRRSRNT  AVEQRLRRLQ  DRSLTQPITT

351  EEVVIAATLQ  ASAHQKALAR  DQTNESKDSA  EQGEPDSSTL  SLAEKLALFN  KLSQPVSKAI  STRNRLDMRQ
                      EEVVIAATLQ  ASAHQKALAK  DQTNEGKELA  EQGEPDSSTL  SLAEKLALFN  KLSQPVSKAI  STRNRIDTRQ

421  RRMNARYQTQ  PVTLGEVEQV  QSGKLMAFSP  TINTSVSTVA  STVPPMYAGN  LRTKPLPDDS  FGATEQKFAS
                      RRMNARYQTQ  PVTLGEVEQV  QSGKLIPFSP  AVNTSVSTVA  STVAPMYAGD  LRTKPPLDHN  ASATDYKFSS

491  SLENSDSPVR  SILKSQGWQP  SVEGAGSKAM  LREFEETERK  GGLTGGDGGV  TKYGSFEEAE  LSYPVLSRVR
                      SIENSDSPVR  SILKSQAWQP  LVEGSENKGM  LREYGETESK  RALTGRDSGM  EKYGSFEEAE  ASYPILNRAR

561  EGDNHKEAIY  ALPRKGSLEL  AHPPIAQLGD  DLKEFSTPKS  TMQASPDWKE  RQLFEEKVDL  ENVTKRKFSL
                      EGDSHKESKY  AVPRRGSLER  ANPPITHLGD  EPKEFSMAKM  NAQGNLDLRD  RLPFEEKVEV  ENVMKRKFSL

631  KAAEFGEPTS  EQTGAAAGKP  AAPTATPVSW  NRLNRKQEYG  KPQDPSEQPQ  EKRYQSPCAM  FAAGEIKAPA  VEGSLDSPSK
                      RAAEFGEPTS  EQTGTAAGKT  IAQTTAPVSW  NRLSRRQEGG  KPQDSSEQPQ  EKLCKNPCAM  FAAGEIKTPT  GEGLLDSPSK

701  TMSIKERLAL  LKKSGEEDWR  NRLNRKQEYG  KASITSSLHI  QETEQSLKKK  RVTESRESQM  TIEERKHLIT
                      TMSIKERLAL  LKKSGEEDWR  NRLSRRQEGG  KAP-ASSLHT  QEAGRSLIKK  RVTESRESQM  TIEERKQLIT

771  VREDAWKTRG  KGAAANDSTQF  TVAGRMVKRG  LASPTAITPV  ASPVSSKARG  TTPVSRPLED  IEARPDMQLE
                      VREEAWKTRG  RGAAANDSTQF  TVAGRMVKKG  LASPTAITPV  ASAICGKTRG  TTPVSKPLED  IEARPDMQLE

841  SDLKLDRLET  FLRRLNNKVG  GMQETVLTVT  GKSVKEVMKP  DDDETFAKFY  RSVDSSLPRS  PVELDEDFDV
                      SDLKLDRLET  FLRRLNNKVG  GMHETVLTVT  GKSVKEVMKP  DDDETFAKFY  RSVDYNMPRS  PVEMDEDFDV

911  SSVAEHKRAV  RPKRRVQASK  NPLKMLAARE  DLLQEYTEQR  LNVAFVESKR  MKVEKLSANS
                      SSVAEHKRAV  RPKRRVQASK  NPLKMLAARE  DLLQEYTEQR  LNVAFMESKR  MKVEKMSSNS
```

FIG. 5A

```
BOVINE  981  SFSEVTLAGL ASKENFSNVS LRSVNLTEQN SNNSAVPYKK LMLLQVKGRR HVQTRLVEPR APSLNSGDCF
HUMAN        NFSEVTLAGL ASKENFSNVS LRSVNLTEQN SNNSAVPYKR LMLLQIKGRR HVQTRLVEPR ASALNSGDCF

1051  LLLSPHHCFL WVGEFANVIE KAKASELASL IQTKRELGCR ATYIQTVEEG INTHTHAAKD FWKLLGGQAS
             LLSPHCCFL  WVGEFANVIE KAKASELATL IQTKRELGCR ATYIQTIEEG INTHTHAAKD FWKLLGGQTS

1121  YQSAGDPKED ELYETAIIET NCIYRLMDDK LVPDDDYWGK IPKCSLLQSK EVLVFDFGSE VYVWHGKEVT
             YQSAGDPKED ELYEAAIIET NCIYRLMDDK LVPDDDYWGK IPKCSLLQPK EVLVFDFGSE VYVWHGKEVT

1191  LAQRKIAFQL AKHLWNGTFD YENCDINPLD PGECNPLIPR KGQGRPDWAI FGRLTEHNET ILFKEKFLDW
             LAQRKIAFQL AKHLWNGTFD YENCDINPLD PGECNPLIPR KGQGRPDWAI FGRLTEHNET ILFKEKFLDW

1261  TELKRPNEKN ASELAQHKDD ARAEVKPYDV TRMVPVPQTT AGTVLDGVNV GRGYGLVEGD DRRQFEIASI
             TELKRSNEKN PGELAQHKED PRTDVKAYDV TRMVSMPQTT AGTILDGVNV GRGYGLVEGH DRRQFEITSV

1331  SVDVWHILEF DYSRLPKQSI GQFHEGDAYV VKWKFIVSTA VGSRQKGEHS VRVAGKEKCV YFFWQGRQST
             SVDVWHILEF DYSRLPKQSI GQFHEGDAYV VKWKFMVSTA VGSRQKGEHS VRAAGKEKCV YFFWQGRHST

1401  VSEKGTSALM TVELDEERGA QVQVLQGKEP PCFLQCFQGG MVVHSGRREE EEENTQSEWR LYCVRGEVPV
             VSEKGTSALM TVELDEERGA QVQVLQGKEP PCFLQCFQGG MVVHSGRREE EEENVQSEWR LYCVRGEVPV

1471  EGNLLEVACH CSSLRSRTSM VVLNVHKALI YLWHGCKAQA HTKEVGRTAA NKIKDQCPLE AGLHSSSKVT
             EGNLLEVACH CSSLRSRTSM VVLNVNKALI YLWHGCKAQA HTKEVGRTAA NKIKEQCPLE AGLHSSSKVT

1541  IHECDEGSEP LGFWDALGRR DRKAYDCMLQ DPGNFNFTPR LFILSSSGD  FSATEFMYPA RDPSVVNSMP
             IHECDEGSEP LGFWDALGRR DRKAYDCMLQ DPGSFNFAPR LFILSSSGD  FAATEFVYPA RAPSVVSSMP

1611  FLQEDLYSAP QPALFLVDNH HEVYLWQGWW PIENKITGSA RIRWASDRKS AMETVLQYCR GKNLKKPPPK
             FLQEDLYSAP QPALFLVDNH HEVYLWQGWW PIENKITGSA RIRWASDRKS AMETVLQYCK GKNLKKPAPK

1681  SYLIHAGLEP LTFTNMFPSW EHREDIAEIT EMDTEVSNQI KQVNLKKAKG TLVEDVLAKL CKTIYPLADL
             SYLIHAGLEP LTFTNMFPSW EHREDIAEIT EMDTEVSNQI KQVNLKKAKG TLVEDVLAKL CKTIYPLADL

1751  PLKLEIYLTD EDFEFALDMT RDEYNALPAW KQVNLKKKAKG LF* (SEQ ID NO: 4)
             PLKLEIYLTD EDFEFALDMT RDEYNALPAW KQVNLKKKAKG LF* (SEQ ID NO: 2)
```

FIG. 5B

Bovine Supervillin cDNA Sequence (Start ATG codon at nt 201)

```
   1 ATTTGAACAA GAAAAACTTA AGCCTCGTTG GATTCCCGTG TCAAAGGAAA
  51 GTTCCAAGCT TTCAGAAAGA GTTCTTGCTT GAAGACaAAG AACAGCTTGA
 101 TaACCACAAA AGAAGGATCG ATGCTCAGCT TTTAGCTGCC CTTCCTAAAG
 151 TTGCAGAATT AAGAAAAATC TTTGAACCaA AGAgGAAAGA ATTTTTAGAA
 201 ATGAAAAGAA AGAAAGAAT TGCCCGGCGC TTAGAAgGAA TTGAAACCGA
 251 CACGCAGCCC ATCCTCTTGC AGAGCTGCAC GGGCTTGGTG ACTCATCGCC
 301 TGCTGGAGGA GGACACACCC AGATACATGC GTGCCACAGA CCCGGCCAGC
 351 CCGCACATTG GTCGATCAAA TGAAGAAgAA GAAACTTCAG ATTCTTCACT
 401 AGAAAAGCAG ACTCGATCCA AACAGTGCAC AGAAACCTCA GGCATCCATG
 451 CTGACTCGCC CTACAGTTCA GGCATCATGG ACACCCAGAG CCTCGAGTCC
 501 AAAGCCGAAA GAATCGCCAG GTACAAAGCA GAGAGAAgAC GGCAGCTGGC
 551 AGAAAAGTAT GGGCTCACCC TGGATCCGGA AGCAGACTCT GAAACTCCAT
 601 CTCGATACAG CAGGTCCAGA AAgGACCCCG AGGCTGCGGA GAAAAgGGgA
 651 GTAaGAAGCG AGCGATCGGC CaAGTcCAGC AGAGACGCCG GCTCATCcTA
 701 CTCCAGGACT GAGCTCTCGG GGCTCAGGAC cTGCGTGGCT GAGTCCAAGG
 751 ACTATGGCcT GCACCGGAGT GACGGTGTTT CCGACACAGA gGTGCTGCTC
 801 AATGCAGAAA ACCAAaGACG CGGTCAAGAG CCCAGTGCCA CCGGGCTGGC
 851 CCGAGACCTG CCCCTTGCAG GGGAGGTCTC CTCTTCTTTC TCATTCTCCG
 901 GGCGAGACTC TGCCCTCGGT GAAGTGCCAA GGTCCCCAAA GGCAGTGCAC
 951 AGCCTGCCCA GTCCATCGCC TGGGCAGCCG GCCTCCCCAA GCCACTCCAC
1001 CAGTGACCcTG CCACTCCcTG CGGaGGCTCG AGCCAGGTCA ACTTCAAATT
1051 CAGAAATGCC AGCTGCCGAG GATGAAGAAA AGGTCGATGA GCGAGCGAGG
1101 CTGAGCGTCG cTGCTaAGAG GCTGCTCTTC AGGGAGATGG AGAAGTCGTT
1151 tGACGAGAAG AGCGTCCCAA AGCGCCGCTC CCGCAATGCG GCCGTGGAGC
1201 AGAGGCTGCG GCGCCTCCAG GACCGGTCCC ACACGCAGCC CGTCACCACC
1251 GAGGAGGTGG TCATTGCAGC CACATTGCAG GCGTCTGCTC ACCAaAAGGC
1301 ACTaGCCAGA GACCAGACAa ACGAGAGCaA AGATTCTGCT GAGCAGGGAG
1351 AACCTGACTC CTCCACTCTG AGCTtAGCGG AGAAgCTGGC CTtGTTTAAC
1401 AAACTATCTC AGCCGGTCTC AAAAGCCATT TCAACaCGGA ACAGATtAGA
1451 CaTGAGACAG AgGAGGATGA ATGCTCGTTA TCAAaCCCaG CCGGTCACGC
1501 TTGGAgAAGT GGAACAGGTG CAGAgTgGCA aGCTCATGGc TTTCTCTCCC
1551 ACCATTAACA CTTCCGTGTC CACCGTGGCA TCTACCGTCC CCCCCATGTA
1601 TGCAGGAAAT CTTCGGACAA AGCCACTTCC AGATGACAGC TTTGGTGCCA
1651 CTGAGCAGAA GTTTGCTTCT TCGCTAGAAA ACTCCGACTC CCCAGTTAGA
1701 AGCATCCTGA AATCCCAAGG CTGGCAGCcC TCGGTCGAGG GTGCTGGGAG
1751 CAAAGCAATG TTGAgAGAAT TTGAAGAGAC AGAACGCAAG GGAGGCTTGA
1801 CAGGTGGAGA TGGCGGGGTT ACAAAGTATG GGTCCTTCGA GGAAGCAGAG
1851 CTGTCCTACC CCGTCCTCAG CAGAGTCCGG GAGGGAGACA ACCATAAAGA
1901 GGCCATCTAT GCCCTTCCGA GGAAAGGAAG CCTGGAGCTC GCCCATCCTC
1951 CCATCGCCCA GCTTGGTGAT GACCTGAAgG AATTTTCCAC CCCAAAGAGC
2001 ACCATGCAGG CAAGCCCAGA CTGGAAGGAG AGGCAGcTCT TTGAAGAGAA
2051 GGTGGACTTG GAGAATGTCA CAAAGAGGAA GTTTTCGCTG AAAGCCGCGG
2101 AGTTCGGGGA ACCCACTTCT GAGCAGACCG GCGCGGCTGC TGGGAAACCG
2151 GCTGCTCCGA CTGCAACCCC GGTGTCCTGG AAGCCGCAGG ATCCCTCCGA
2201 ACAGCCTCAG GAGAAGCGGT ATCAGAGCCC gTGTGCGATG TTTGCTGCTG
2251 GAGAGATCAA AGCCCGGCG GTGGAGGGCA GCcTCGACTC CCCCAGCAAA
2301 ACCATGTCCA TTAAAGAAAG ATTAGCACTG TTgAAGAAGA GCGGTGAGGA
2351 AGACTGGAGA AACAGACTCA ACAGAAAGCA GGAATACGGC AAAGCCTCCA
2401 TCACCAGCAG CCTGCACAtC CAAGAGACGG AGCAGTCACT CAAGAAGAAG
2451 CGGGTCACAG AAAGTCGAGA GAGCCAGATG ACTATTGAAG AGAGAAAGCA
2501 TCTCATCACC GTGAGAGAGg ACGCCTGGAA GACCAGGGGC AAAGGAGCAG
2551 CCAACGACTc TACCCAGTTT ACTGTGGCCG GCAGGATGGT GAAGCGAGGT
2601 CTGGCGTCCC CCACTGCCAT CACCCCGGTa gCATCCCCTG TTTCCAGCAA
2651 AGCAAGGGGC ACTACACCAG TTTCCAGACC CCTGGAAGAT ATCGAAGCCA
2701 GACCAGACAT GCAGTTaGAG TCGGACCTCA AGCTGGACAG GCTGGAAACC
```

FIG. 9A

2751 TTCCTaAGAA GGCTGAATAA cAaAGTTGGT GGGATGCAAG AAACAGTCcT
2801 CACTGTCACT GGGaAATCGG TGAAAGAGGT GATGAAGCCG GACGATGATG
2851 AAACCTTTGC CAAGTtTtAC CGCAGCGTGG ACTCCTcTCT ACCGAGAAGC
2901 CCCGTAGAGC TGGACgAGGA tTTcGATGTC ATTTTTGATC CTTATGCCCC
2951 CAGGTTGACA TCCTCGGTGG CTGAGCACaA gCGTGCCGTG CGgcCCAAGC
3001 GCCGGGTCCA GGCTTCCAAA AACCCCCTgA AGATGCTGGC CGCGAGGGAA
3051 GATCTCCTGC AGGAGTACAC TGAGcAGAGA CTGAACGTGG CCTTCGTGGA
3101 GTcAAAGCGG ATGAAaGTCG AAAAGTTGTC CGCCAACTCC AGCTTCTCAG
3151 AAGTCACCCT GGCgGGGTTA GCCAGCAAAG AAAaCTTCAG CAACGTCAGC
3201 CTGCGGaGCG TCAACCTGAC GGAACAGAAT TCCAACAACA GTgCAGTGCC
3251 CTACAAGAAG CTGATGCTGC TGCAGGTTAA AGGAAGAAgA CACGTGCAGA
3301 CGCGGCTGGT GGAgCCTCGC GCCCCCTCCC TcAACAGCGG GGACTGCTTC
3351 CTCcTGCTCT CGCCCCATCA CTGCTTCCTG TGGGTCGGAG AGTTCGCCAA
3401 CGTGATCGAg AAGGCGAAGG CCTCAgAACT TGCGAgTTTA ATTCAgACCA
3451 AGAGGGAACT TGGTTGTAgA GCAACTTACA TCCAgACTGT TGAAgAAGGA
3501 ATTAATACAC ACACACATGC AGCCAAAGAC TTCTGGAAGC TTCTGGGCGG
3551 CCAAGCCAGT TACCAATCCG CCGGAgACCC AAAGGAGGAT GAGCTCTATG
3601 AAACGGCCAT AATAgAgACC AACTGCATTT ACCGTCTGAT GGATGACAAA
3651 CTCGTTCCTG ATGATGACTA CTGGGGGAAg ATCCCAAAGT GCTCCCTCCT
3701 GCAATCAAAA gAGGTACTGG TGTTTGATTT TGGGAGTGAA GTTTACGTGT
3751 GGCATGGAAA AGAAGTCACA TTAGCACAAC GGaAAATCGC CTTTCAGCTG
3801 GCAAAGCACT TGTGGAATGG AACCTTTGAc TACGAGAATT GTGACATTAA
3851 CCCGCTGGAT CCTGGGGAAT GCAATCCCCT CATTCCCAGG AAAGGACAGG
3901 GGCGGCCCGA CTGGGCAATA TTTGGGAGAC TTACAGAACA CAATGAGACG
3951 ATCTTGTTCA AGAGAAATT CCTTGATTGG ACGGAACTGA AGAGACCTAA
4001 CGAGAAGAAC GCCAGCGAAC TCGCGCAGCA CAAGGACGAT GCCcGGGCAG
4051 AGGTCAAGCC TTACGACGTG ACGCGGATGG TGCCCGTGCC CCAGACAACA
4101 GCCGGCACCG TGCTGGATgG GGTCAACGTG GGCCGAGGCT ACGGGCTGGT
4151 GGAAgGGGAC GACCGGAGGC AGTTCGAGAT CGCCAGCATC TCAGTGGACG
4201 TCTGGCACAT CCTGGAGTTC GACTACAGCA GGCTCCCCAA GcAGAGCATC
4251 GGGCAGTTCC ACGAAgGCgA TGCcTACGTG GTGAAGTGGA AGTTCATCGT
4301 GAGCACTGCA GTGGGAAGCC GGCAGAAGGG GGAGCACTCG GTCAGGGTGG
4351 CTGGCAAAGA GAAATGTGTC TACTTCTTCT GGCAAGGCCG CCAGTCGACC
4401 GTGAGTGAGA AGGGCACAtC AGCTCTGATG ACAGTGGAGC TGGACgAgGA
4451 AAGGGGGGCC CAGGTCCAGG TCCTGCAGGG CAAGGAGCCC CCCTGTTTCC
4501 TGCAGTGCTT CCAgGGGGGG ATGGTGGTCC ACTCCGGGAG ACGGGAGGAG
4551 GAgGAAgAgA ACACACAGAG CGAGTGGCGG CTGTACTGTG TGCGCGGAGA
4601 GGtGCCTGTG GAGGGGAaCT TGCTGGAGGT GGCCTGTCAC TGCAGCAGCC
4651 TCAGGTCTAG GACGTCCATG GTTGTCCtCA ACGTCCACAA AGCCCcTcAtc
4701 TACCTGTGGC ATGGATGCAA AGCCCAgGCC CACACgAAgG AggTCGGACG
4751 GACTGCAgCC AATAAAATCA AgGACCAATG TCCCCTGgAG GCCGGGCTGC
4801 ACAGTAgCAg CaAAGTGACA ATTCATGAGT GTgATGAAGG CTCGGAGCCC
4851 CTGGGGTTCT GGGACGcTCT GGGGAGGAgA gACCGGAAAG CCTACGACTG
4901 CATGCTTCAA GATCCTGgAA ATTTTAACTT CaCACCCCGC CTGTTCATCC
4951 TCAGCAGCTC cTCTGGTGAC TTCTCAGCCA CAGAGTTCAT GTATCCCGCC
5001 CGAGACCCCT CTGTGGTCAA CTcTATGCCC TTCCTGCAGG AAGACCcTATa
5051 CAGTGCCCCA CAGCCAGCAC TcTTCcTTGT TGACAATCAC CACGAGGTGT
5101 ACcTCTGGCA AGGCTGGTGG CCCATCGAGA ACAAGATCAC GGGCTCCGCG
5151 CGCATCCGCT GGGCCTCGGA CCGGAAGAgC GCCATGGAGA CAGTGCTGCA
5201 GTACTGCCGA GGGAAAAACC TGAAGAAGCC GCCCCCCAAG TCTTACcTCa
5251 TCCACGCTGG cCTGGAACCC CTGACCTTCA CCAACATGTT CCCCAGCTGG
5301 GAGCACAGAG AAgACATTGC AGAGATCACG GAGATGGACA CGGAAGTTTC
5351 AAATCAGATC ACCCTAGTGG AGGATGTCTT AGCCAaACTG TGTAAGACCA
5401 TTTACCCACT GGCCGACCTC CTAGCCAGGC CGCTCCCTGA GGGAGTTGAC
5451 CCTCTGAAGC TGGAGATCTA TCTCACCGAC GAGGACTTCG AGTTTGCACt
5501 AGACATGACC CGAGACGAGT ACAATGCACT GCCCGCTTGG AAgCAGGTGA
5551 ACCTGAAGAA AGCGAAAGGT CTGTTcTGAG TCAGGAGATG CTGGAGGAAC
5601 CTGGGTGGTC ACTTTCaATA CTGATGGACC AGGAAAATGG ATGTTTTAGT

FIG. 9B

```
5651  GGGGGAGCCT GGTATTTTtA AATATGTTTT TTCATcTGCA TTTTTAAAAC
5701  CTGAAGTGAC CAGCTcTCCT GCTTGTTTGG GAGTTGTGTA TTTTGTAAAT
5751  GTTCCAGAGA ACTcTcTGGG AACATGCTTT CCACACATCA GCAGGTGATG
5801  TTcGTGAGGT ATCCGTGGCC CTACACGCAc TTATGCAGCA GGTCCTCAGT
5851  GGCGGCCACG GCACCGCCCT CCCGCTCCAG CTcAGCGTTG CCTATTTTTT
5901  TGAAGCAGTT cTcTTTATAA AGTGTTATtT TGATAGTTTG TGGATTcTAA
5951  AATATATATA TATTTATATA AACACCATaT AAATCAAATA TGTATTtAAC
6001  AAACCAGTAT GTATTCATTC ACTTTTAAGA TTTTTTTTTT TtGGTGTCAA
6051  AATAATATTA AAAGGCAGTT GCCTCTGTTG AGTTAGTTCT GCCACCTGTG
6101  TGTACTTTCA CCCACGTTCA GAAGCGTcTC CTTtGGTGTG AAGTCTGACT
6151  CGTTCTGAGT GCTGCTTCCG GTGCTAAGAT gAaCAAaGGC TcTTAAGAAT
6201  CTGTGCGAAT CCACCTTTcT ACCTTAATAT CGCCCCCAAA TGTATAGTGC
6251 .CTTGTTTTAT GTACAGTTTA TATACAGAAA AGTTTGCTCT GCATTTTTTG
6301  ACGATGGTTT GGAACAGTAT CTACAATTTT ACTCTAAAAT AGTAGAAATT
6351  TCgAAAAAAA AAAAAAyyAA CTCTATTTCT AATACCTGTT GTAAACATTA
6401  TACATGTCAT TTGGTGACGG AGGAATCCAA AATAAAAGCT TCAGAATAAA
6451  CACAACTTAA AAA
```

FIG. 9C

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 6718 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: Coding Sequence
      (B) LOCATION: 451...5814

(xi) SEQUENCE DESCRIPTION: SEQ ID NO:1:

```
TCGGCGGGAA GCGGCGATCC TGCCACCGGG AGGTGTGGAA GAGCCGGGTA GATTCTGGCT      60

ACATTGGAGA TTGGTTGCTT TCTAAAACTG AAGGAGAAGC CCATGAAGAG ATGGTGGATT     120

CTCACTGAGT TTTGACTAGC GGAAGAAAAG AGAGAGTTCA AGTGGATGGC CTTGAGGACT     180

TGAAAAGCTG AGATATGATG ATTTTGAAGT CATTTCACAT CGAAGCCATG ATTTAAATAT     240

CGGCGTTAAG ATTTCAACAA GAAAAACTTA AGCTTCCTTG GATTCCCACG TCAAAGGAAA     300

GTTTCAAGCT TTCAGAAGGA GTTCTCACTC GAAGATAAAG AACAGCTCGC TAACCACGAA     360

AGAGGAATCG ATGCTCAGCT TTTAGTTGCA CTTCCTAAAG TTGCAGAATT AAGACAAATC     420

TTTGAACCAA AGAAGAAAGA ATTCTTAGAA  ATG AAA AGA AAA GAA AGA ATT GCC     474
                                 Met Lys Arg Lys Glu Arg Ile Ala
                                  1               5

AGG CGC CTG GAA GGG ATT GAA AAT GAC ACT CAG CCC ATC CTC TTG CAG       522
Arg Arg Leu Glu Gly Ile Glu Asn Asp Thr Gln Pro Ile Leu Leu Gln
     10              15                  20

AGC TGC ACA GGA TTG GTG ACT CAC CGC CTG CTG GAG GAA GAC ACC CCT       570
Ser Cys Thr Gly Leu Val Thr His Arg Leu Leu Glu Glu Asp Thr Pro
 25              30                  35                  40

CGA TAC ATG AGA GCC AGC GAC CCT GCC AGC CCC CAC ATC GGC CGA TCA       618
Arg Tyr Met Arg Ala Ser Asp Pro Ala Ser Pro His Ile Gly Arg Ser
                 45                  50                  55

AAT GAA GAG GAG GAA ACT TCT GAT TCT TCT CTA GAA AAG CAA ACT CGA       666
Asn Glu Glu Glu Glu Thr Ser Asp Ser Ser Leu Glu Lys Gln Thr Arg
                     60                  65                  70

TCC AAA TAC TGC ACA GAA ACC TCC GGT GTC CAC GGT GAC TCA CCC TAT       714
Ser Lys Tyr Cys Thr Glu Thr Ser Gly Val His Gly Asp Ser Pro Tyr
             75                  80                  85

GGT TCG GGT ACC ATG GAC ACC CAC AGT CTG GAG TCC AAA GCC GAA AGA       762
Gly Ser Gly Thr Met Asp Thr His Ser Leu Glu Ser Lys Ala Glu Arg
         90                  95                 100

ATT GCA AGG TAC AAA GCA GAA AGA AGG CGA CAG CTG GCA GAG AAG TAT       810
```

-continued

```
              Ile Ala Arg Tyr Lys Ala Glu Arg Arg Gln Leu Ala Glu Lys Tyr
              105                 110                 115                 120

GGG CTG ACT CTG GAT CCC GAG GCC GAC TCC GAG TAT TTA TCC CGC TAT              858
Gly Leu Thr Leu Asp Pro Glu Ala Asp Ser Glu Tyr Leu Ser Arg Tyr
            125                 130                 135

ACC AAG TCC AGG AAG GAG CCT GAT GCT GTC GAG AAG CGG GGA GGA AAA              906
Thr Lys Ser Arg Lys Glu Pro Asp Ala Val Glu Lys Arg Gly Gly Lys
            140                 145                 150

AGT GAC AAA CAG GAA GAG TCA AGC AGA GAT GCG AGT TCT CTG TAC CCC              954
Ser Asp Lys Gln Glu Glu Ser Ser Arg Asp Ala Ser Ser Leu Tyr Pro
            155                 160                 165

GGG ACC GAG ACG ATG GGC CTC AGG ACC TGT GCC GGT GAA TCC AAG GAC             1002
Gly Thr Glu Thr Met Gly Leu Arg Thr Cys Ala Gly Glu Ser Lys Asp
            170                 175                 180

TAT GCC CTC CAT GCG GGT GAC GGC TCT TCC GAC CCG GAG GTG CTG CTG             1050
Tyr Ala Leu His Ala Gly Asp Gly Ser Ser Asp Pro Glu Val Leu Leu
185                 190                 195                 200

AAC ATA GAA AAC CAA AGA CGA GGT CAA GAG CTG AGT GCC ACC CGG CAG             1098
Asn Ile Glu Asn Gln Arg Arg Gly Gln Glu Leu Ser Ala Thr Arg Gln
            205                 210                 215

GCC CAT GAC CTG TCC CCA GCA GCC GAG AGT TCC TCG ACC TTC TCT TTC             1146
Ala His Asp Leu Ser Pro Ala Ala Glu Ser Ser Ser Thr Phe Ser Phe
            220                 225                 230

TCT GGG CGA GAC TCC TCC TTC ACT GAA GTG CCA CGG TCC CCC AAG CAC             1194
Ser Gly Arg Asp Ser Ser Phe Thr Glu Val Pro Arg Ser Pro Lys His
            235                 240                 245

GCC CAC AGC TCC TCC CTG CAG CAG GCA GCC TCC CGG AGC CCC TCC TTT             1242
Ala His Ser Ser Ser Leu Gln Gln Ala Ala Ser Arg Ser Pro Ser Phe
            250                 255                 260

GGT GAC CCA CAG CTA TCC CCT GAG GCC CGA CCC AGG TGC ACT TCA CAT             1290
Gly Asp Pro Gln Leu Ser Pro Glu Ala Arg Pro Arg Cys Thr Ser His
265                 270                 275                 280

TCA GAA ACG CCA ACT GTC GAT GAT GAA GAA AAG GTG GAT GAA CGA GCC             1338
Ser Glu Thr Pro Thr Val Asp Asp Glu Glu Lys Val Asp Glu Arg Ala
            285                 290                 295

AAG CTG AGC GTC GCC GCC AAG AGG TTG CTT TTC AGG GAG ATG GAA AAA             1386
Lys Leu Ser Val Ala Ala Lys Arg Leu Leu Phe Arg Glu Met Glu Lys
            300                 305                 310

TCT TTT GAT GAA CAA AAT GTT CCA AAG CGA CGC TCA AGA AAC ACA GCT             1434
Ser Phe Asp Glu Gln Asn Val Pro Lys Arg Arg Ser Arg Asn Thr Ala
            315                 320                 325

GTG GAG CAG AGG CTA CGC CGT CTG CAG GAC AGG TCC CTC ACC CAG CCC             1482
Val Glu Gln Arg Leu Arg Arg Leu Gln Asp Arg Ser Leu Thr Gln Pro
            330                 335                 340

ATC ACC ACT GAA GAG GTG GTC ATC GCA GCC ACA TTG CAG GCC TCT GCT             1530
Ile Thr Thr Glu Glu Val Val Ile Ala Ala Thr Leu Gln Ala Ser Ala
345                 350                 355                 360

CAC CAA AAG GCC TTA GCC AAG GAC CAG ACA AAT GAG GGC AAA GAG CTT             1578
His Gln Lys Ala Leu Ala Lys Asp Gln Thr Asn Glu Gly Lys Glu Leu
            365                 370                 375

GCT GAG CAA GGA GAA CCT GAT TCC TCC ACT CTA AGC TTG GCC GAA AAG             1626
Ala Glu Gln Gly Glu Pro Asp Ser Ser Thr Leu Ser Leu Ala Glu Lys
            380                 385                 390

TTG GCC TTG TTT AAC AAA TTG TCC CAG CCA GTC TCA AAA GCG ATT TCT             1674
Leu Ala Leu Phe Asn Lys Leu Ser Gln Pro Val Ser Lys Ala Ile Ser
            395                 400                 405

ACC CGG AAC AGA ATA GAC ACG AGA CAG AGG AGA ATG AAC GCT CGC TAT             1722
Thr Arg Asn Arg Ile Asp Thr Arg Gln Arg Arg Met Asn Ala Arg Tyr
            410                 415                 420

CAA ACT CAG CCA GTC ACA CTG GGA GAG GTG GAG CAG GTG CAG AGT GGA             1770
```

```
Gln Thr Gln Pro Val Thr Leu Gly Glu Val Glu Gln Val Gln Ser Gly
425                 430                 435                 440

AAG CTC ATT CCT TTC TCA CCT GCC GTG AAC ACA TCA GTG TCT ACC GTA    1818
Lys Leu Ile Pro Phe Ser Pro Ala Val Asn Thr Ser Val Ser Thr Val
                    445                 450                 455

GCA TCC ACG GTT GCT CCA ATG TAT GCC GGA GAT CTT CGC ACA AAG CCA    1866
Ala Ser Thr Val Ala Pro Met Tyr Ala Gly Asp Leu Arg Thr Lys Pro
                460                 465                 470

CCT CTT GAC CAC AAT GCA AGT GCC ACT GAC TAT AAG TTT TCT TCT TCA    1914
Pro Leu Asp His Asn Ala Ser Ala Thr Asp Tyr Lys Phe Ser Ser Ser
            475                 480                 485

ATA GAA AAT TCG GAC TCT CCA GTT AGA AGC ATT CTG AAA TCG CAA GCT    1962
Ile Glu Asn Ser Asp Ser Pro Val Arg Ser Ile Leu Lys Ser Gln Ala
        490                 495                 500

TGG CAG CCT TTG GTA GAG GGT AGC GAG AAC AAG GGA ATG TTG AGA GAA    2010
Trp Gln Pro Leu Val Glu Gly Ser Glu Asn Lys Gly Met Leu Arg Glu
505                 510                 515                 520

TAT GGA GAG ACA GAA AGC AAG AGA GCT TTG ACA GGT CGA GAC AGT GGG    2058
Tyr Gly Glu Thr Glu Ser Lys Arg Ala Leu Thr Gly Arg Asp Ser Gly
                525                 530                 535

ATG GAG AAG TAT GGG TCC TTT GAG GAA GCA GAA GCA TCC TAC CCC ATC    2106
Met Glu Lys Tyr Gly Ser Phe Glu Glu Ala Glu Ala Ser Tyr Pro Ile
                540                 545                 550

CTG AAC AGA GCC AGG GAA GGA GAC AGC CAT AAG GAA TCT AAA TAT GCT    2154
Leu Asn Arg Ala Arg Glu Gly Asp Ser His Lys Glu Ser Lys Tyr Ala
            555                 560                 565

GTT CCC AGA AGA GGA AGC CTG GAA CGG GCG AAC CCT CCC ATC ACC CAC    2202
Val Pro Arg Arg Gly Ser Leu Glu Arg Ala Asn Pro Pro Ile Thr His
        570                 575                 580

CTC GGG GAT GAA CCG AAG GAA TTT TCC ATG GCT AAA ATG AAT GCA CAA    2250
Leu Gly Asp Glu Pro Lys Glu Phe Ser Met Ala Lys Met Asn Ala Gln
585                 590                 595                 600

GGA AAC TTG GAC TTG AGG GAC AGG CTG CCC TTT GAA GAG AAG GTG GAG    2298
Gly Asn Leu Asp Leu Arg Asp Arg Leu Pro Phe Glu Glu Lys Val Glu
                605                 610                 615

GTG GAG AAT GTT ATG AAA AGG AAG TTT TCA CTA AGA GCG GCA GAG TTC    2346
Val Glu Asn Val Met Lys Arg Lys Phe Ser Leu Arg Ala Ala Glu Phe
                620                 625                 630

GGG GAG CCC ACT TCC GAG CAG ACG GGG ACA GCT GCT GGG AAA ACT ATT    2394
Gly Glu Pro Thr Ser Glu Gln Thr Gly Thr Ala Ala Gly Lys Thr Ile
            635                 640                 645

GCT CAA ACC ACA GCC CCC GTG TCC TGG AAG CCC CAG GAT TCT TCG GAA    2442
Ala Gln Thr Thr Ala Pro Val Ser Trp Lys Pro Gln Asp Ser Ser Glu
        650                 655                 660

CAG CCA CAG GAG AAG CTC TGC AAG AAT CCA TGT GCG ATG TTT GCT GCT    2490
Gln Pro Gln Glu Lys Leu Cys Lys Asn Pro Cys Ala Met Phe Ala Ala
665                 670                 675                 680

GGA GAG ATC AAA ACG CCG ACA GGG GAG GGC CTT CTT GAC TCA CCC AGC    2538
Gly Glu Ile Lys Thr Pro Thr Gly Glu Gly Leu Leu Asp Ser Pro Ser
                685                 690                 695

AAA ACC ATG TCT ATT AAA GAA AGA TTG GCA CTG TTG AAG AAA AGC GGG    2586
Lys Thr Met Ser Ile Lys Glu Arg Leu Ala Leu Leu Lys Lys Ser Gly
                700                 705                 710

GAG GAA GAT TGG AGA AAC AGA CTC AGC AGG AGG CAG GAG GGC GGC AAG    2634
Glu Glu Asp Trp Arg Asn Arg Leu Ser Arg Arg Gln Glu Gly Gly Lys
            715                 720                 725

GCG CCG GCC AGC AGC CTG CAC ACC CAG GAA GCA GGG CGG TCC CTC ATC    2682
Ala Pro Ala Ser Ser Leu His Thr Gln Glu Ala Gly Arg Ser Leu Ile
        730                 735                 740

AAG AAG CGG GTC ACA GAA AGT CGA GAG AGC CAA ATG ACG ATT GAG GAG    2730
```

```
Lys Lys Arg Val Thr Glu Ser Arg Glu Ser Gln Met Thr Ile Glu Glu
745                 750                 755                 760

AGG AAG CAG CTC ATC ACT GTG AGA GAG GAG GCC TGG AAG ACG AGA GGC       2778
Arg Lys Gln Leu Ile Thr Val Arg Glu Glu Ala Trp Lys Thr Arg Gly
                765                 770                 775

AGA GGA GCG GCC AAC GAC TCG ACC CAG TTC ACT GTG GCT GGC AGG ATG       2826
Arg Gly Ala Ala Asn Asp Ser Thr Gln Phe Thr Val Ala Gly Arg Met
                    780                 785                 790

GTG AAG AAA GGT TTG GCG TCA CCT ACT GCC ATA ACC CCA GTA GCC TCA       2874
Val Lys Lys Gly Leu Ala Ser Pro Thr Ala Ile Thr Pro Val Ala Ser
            795                 800                 805

GCC ATT TGC GGT AAA ACA AGA GGC ACC ACA CCC GTT TCC AAA CCC CTG       2922
Ala Ile Cys Gly Lys Thr Arg Gly Thr Thr Pro Val Ser Lys Pro Leu
        810                 815                 820

GAA GAT ATC GAA GCC AGA CCA GAT ATG CAG TTA GAA TCG GAC CTG AAG       2970
Glu Asp Ile Glu Ala Arg Pro Asp Met Gln Leu Glu Ser Asp Leu Lys
825                 830                 835                 840

TTG GAC AGG CTG GAA ACC TTT CTA AGA AGG CTG AAT AAC AAA GTT GGC       3018
Leu Asp Arg Leu Glu Thr Phe Leu Arg Arg Leu Asn Asn Lys Val Gly
                845                 850                 855

GGG ATG CAC GAA ACG GTG CTC ACT GTC ACC GGC AAA TCT GTG AAG GAG       3066
Gly Met His Glu Thr Val Leu Thr Val Thr Gly Lys Ser Val Lys Glu
                    860                 865                 870

GTG ATG AAG CCA GAT GAT GAT GAA ACC TTT GCC AAA TTT TAC CGC AGC       3114
Val Met Lys Pro Asp Asp Asp Glu Thr Phe Ala Lys Phe Tyr Arg Ser
            875                 880                 885

GTG GAT TAT AAT ATG CCA AGA AGT CCT GTG GAG ATG GAT GAG GAC TTC       3162
Val Asp Tyr Asn Met Pro Arg Ser Pro Val Glu Met Asp Glu Asp Phe
        890                 895                 900

GAT GTC ATT TTC GAT CCT TAT GCA CCC AAA TTG ACG TCT TCC GTG GCC       3210
Asp Val Ile Phe Asp Pro Tyr Ala Pro Lys Leu Thr Ser Ser Val Ala
905                 910                 915                 920

GAG CAC AAG CGG GCA GTT AGG CCC AAG CGC CGG GTT CAG GCC TCC AAA       3258
Glu His Lys Arg Ala Val Arg Pro Lys Arg Arg Val Gln Ala Ser Lys
                925                 930                 935

AAC CCC CTG AAA ATG CTG GCG GCA AGA GAA GAT CTC CTT CAG GAA TAC       3306
Asn Pro Leu Lys Met Leu Ala Ala Arg Glu Asp Leu Leu Gln Glu Tyr
                    940                 945                 950

ACT GAG CAG AGA TTA AAC GTT GCC TTC ATG GAG TCA AAG CGG ATG AAA       3354
Thr Glu Gln Arg Leu Asn Val Ala Phe Met Glu Ser Lys Arg Met Lys
            955                 960                 965

GTA GAA AAG ATG TCT TCC AAC TCC AAC TTC TCA GAA GTC ACC CTG GCG       3402
Val Glu Lys Met Ser Ser Asn Ser Asn Phe Ser Glu Val Thr Leu Ala
        970                 975                 980

GGT TTA GCC AGT AAA GAA AAC TTC AGC AAC GTC AGC CTG CGG AGC GTC       3450
Gly Leu Ala Ser Lys Glu Asn Phe Ser Asn Val Ser Leu Arg Ser Val
985                 990                 995                 1000

AAC CTG ACG GAA CAG AAC TCT AAC AAC AGC GCC GTG CCC TAC AAG AGG       3498
Asn Leu Thr Glu Gln Asn Ser Asn Asn Ser Ala Val Pro Tyr Lys Arg
                1005                1010                1015

CTG ATG CTG TTG CAG ATT AAA GGA AGA AGA CAT GTG CAG ACC AGG CTG       3546
Leu Met Leu Leu Gln Ile Lys Gly Arg Arg His Val Gln Thr Arg Leu
                    1020                1025                1030

GTG GAA CCT CGA GCT TCG GCG CTC AAC AGT GGG GAC TGC TTC CTC CTG       3594
Val Glu Pro Arg Ala Ser Ala Leu Asn Ser Gly Asp Cys Phe Leu Leu
            1035                1040                1045

CTC TCT CCC CAC TGC TGC TTC CTG TGG GTA GGA GAG TTT GCA AAC GTC       3642
Leu Ser Pro His Cys Cys Phe Leu Trp Val Gly Glu Phe Ala Asn Val
        1050                1055                1060

ATA GAA AAG GCG AAG GCC TCA GAA CTT GCA ACT TTA ATT CAG ACA AAG       3690
```

-continued

```
Ile Glu Lys Ala Lys Ala Ser Glu Leu Ala Thr Leu Ile Gln Thr Lys
1065                1070                1075                1080

AGG GAA CTT GGT TGT AGA GCT ACT TAT ATC CAA ACC ATT GAA GAA GGA         3738
Arg Glu Leu Gly Cys Arg Ala Thr Tyr Ile Gln Thr Ile Glu Glu Gly
                1085                1090                1095

ATT AAT ACA CAC ACT CAT GCA GCC AAA GAC TTC TGG AAG CTT CTG GGT         3786
Ile Asn Thr His Thr His Ala Ala Lys Asp Phe Trp Lys Leu Leu Gly
1100                1105                1110

GGC CAA ACC AGT TAC CAA TCT GCT GGA GAC CCA AAA GAA GAT GAA CTC         3834
Gly Gln Thr Ser Tyr Gln Ser Ala Gly Asp Pro Lys Glu Asp Glu Leu
                1115                1120                1125

TAT GAA GCA GCC ATA ATA GAA ACT AAC TGC ATT TAC CGT CTC ATG GAT         3882
Tyr Glu Ala Ala Ile Ile Glu Thr Asn Cys Ile Tyr Arg Leu Met Asp
                1130                1135                1140

GAC AAA CTT GTT CCT GAT GAC GAC TAC TGG GGG AAA ATT CCG AAG TGC         3930
Asp Lys Leu Val Pro Asp Asp Asp Tyr Trp Gly Lys Ile Pro Lys Cys
1145                1150                1155                1160

TCC CTT CTG CAA CCC AAA GAG GTA CTG GTG TTT GAT TTT GGT AGT GAA         3978
Ser Leu Leu Gln Pro Lys Glu Val Leu Val Phe Asp Phe Gly Ser Glu
                1165                1170                1175

GTT TAC GTA TGG CAT GGG AAA GAA GTC ACA TTA GCA CAA CGA AAA ATA         4026
Val Tyr Val Trp His Gly Lys Glu Val Thr Leu Ala Gln Arg Lys Ile
                1180                1185                1190

GCA TTT CAG CTG GCA AAG CAC TTA TGG AAT GGA ACC TTT GAC TAT GAG         4074
Ala Phe Gln Leu Ala Lys His Leu Trp Asn Gly Thr Phe Asp Tyr Glu
                1195                1200                1205

AAC TGT GAC ATC AAT CCC CTG GAT CCT GGA GAA TGC AAT CCG CTT ATC         4122
Asn Cys Asp Ile Asn Pro Leu Asp Pro Gly Glu Cys Asn Pro Leu Ile
                1210                1215                1220

CCC AGA AAA GGA CAG GGG CGG CCC GAC TGG GCG ATA TTT GGG AGA CTT         4170
Pro Arg Lys Gly Gln Gly Arg Pro Asp Trp Ala Ile Phe Gly Arg Leu
1225                1230                1235                1240

ACT GAA CAC AAT GAG ACG ATT TTG TTC AAA GAG AAG TTT CTG GAT TGG         4218
Thr Glu His Asn Glu Thr Ile Leu Phe Lys Glu Lys Phe Leu Asp Trp
                1245                1250                1255

ACG GAA CTG AAG AGA TCG AAT GAG AAG AAC CCC GGG GAA CTT GCC CAG         4266
Thr Glu Leu Lys Arg Ser Asn Glu Lys Asn Pro Gly Glu Leu Ala Gln
                1260                1265                1270

CAC AAG GAA GAC CCC AGG ACT GAT GTC AAG GCA TAC GAT GTG ACA CGG         4314
His Lys Glu Asp Pro Arg Thr Asp Val Lys Ala Tyr Asp Val Thr Arg
                1275                1280                1285

ATG GTG TCC ATG CCC CAG ACG ACA GCA GGC ACC ATC CTG GAC GGA GTG         4362
Met Val Ser Met Pro Gln Thr Thr Ala Gly Thr Ile Leu Asp Gly Val
                1290                1295                1300

AAC GTC GGC CGT GGC TAT GGC CTG GTG GAA GGA CAC GAC AGG AGG CAG         4410
Asn Val Gly Arg Gly Tyr Gly Leu Val Glu Gly His Asp Arg Arg Gln
1305                1310                1315                1320

TTT GAG ATC ACC AGC GTT TCC GTG GAT GTC TGG CAC ATC CTG GAA TTC         4458
Phe Glu Ile Thr Ser Val Ser Val Asp Val Trp His Ile Leu Glu Phe
                1325                1330                1335

GAC TAT AGC AGG CTC CCC AAA CAA AGC ATC GGG CAG TTC CAT GAG GGG         4506
Asp Tyr Ser Arg Leu Pro Lys Gln Ser Ile Gly Gln Phe His Glu Gly
                1340                1345                1350

GAT GCC TAT GTG GTC AAG TGG AAG TTC ATG GTG AGC ACG GCA GTG GGA         4554
Asp Ala Tyr Val Val Lys Trp Lys Phe Met Val Ser Thr Ala Val Gly
                1355                1360                1365

AGT CGC CAG AAG GGA GAG CAC TCG GTG AGG GCA GCC GGC AAA GAG AAG         4602
Ser Arg Gln Lys Gly Glu His Ser Val Arg Ala Ala Gly Lys Glu Lys
                1370                1375                1380

TGC GTC TAC TTC TTC TGG CAA GGC CGG CAC TCC ACC GTG AGT GAG AAG         4650
```

```
                Cys Val Tyr Phe Phe Trp Gln Gly Arg His Ser Thr Val Ser Glu Lys
                1385                1390                1395                1400

GGC ACG TCG GCG CTG ATG ACG GTG GAG CTG GAC GAG GAA AGG GGG GCC          4698
Gly Thr Ser Ala Leu Met Thr Val Glu Leu Asp Glu Glu Arg Gly Ala
                1405                1410                1415

CAG GTC CAG GTT CTC CAG GGA AAG GAG CCC CCC TGT TTC CTG CAG TGT          4746
Gln Val Gln Val Leu Gln Gly Lys Glu Pro Pro Cys Phe Leu Gln Cys
                1420                1425                1430

TTC CAG GGG GGG ATG GTG GTG CAC TCG GGG AGG CGG GAA GAG GAA GAA          4794
Phe Gln Gly Gly Met Val Val His Ser Gly Arg Arg Glu Glu Glu Glu
                1435                1440                1445

GAA AAT GTG CAA AGT GAG TGG CGG CTG TAC TGC GTG CGT GGA GAG GTG          4842
Glu Asn Val Gln Ser Glu Trp Arg Leu Tyr Cys Val Arg Gly Glu Val
                1450                1455                1460

CCC GTG GAA GGG AAT TTG CTG GAA GTG GCC TGT CAC TGT AGC AGC CTG          4890
Pro Val Glu Gly Asn Leu Leu Glu Val Ala Cys His Cys Ser Ser Leu
1465                1470                1475                1480

AGG TCC AGA ACT TCC ATG GTG GTG CTT AAC GTC AAC AAG GCC CTC ATC          4938
Arg Ser Arg Thr Ser Met Val Val Leu Asn Val Asn Lys Ala Leu Ile
                1485                1490                1495

TAC CTG TGG CAC GGA TGC AAA GCC CAG GCC CAC ACG AAG GAG GTC GGA          4986
Tyr Leu Trp His Gly Cys Lys Ala Gln Ala His Thr Lys Glu Val Gly
                1500                1505                1510

AGG ACC GCT GCG AAC AAG ATC AAG GAA CAA TGT CCC CTG GAA GCA GGA          5034
Arg Thr Ala Ala Asn Lys Ile Lys Glu Gln Cys Pro Leu Glu Ala Gly
                1515                1520                1525

CTG CAT AGT AGC AGC AAA GTC ACA ATA CAC GAG TGT GAT GAA GGC TCC          5082
Leu His Ser Ser Ser Lys Val Thr Ile His Glu Cys Asp Glu Gly Ser
                1530                1535                1540

GAG CCA CTC GGA TTC TGG GAT GCC TTA GGA AGG AGA GAC AGG AAA GCC          5130
Glu Pro Leu Gly Phe Trp Asp Ala Leu Gly Arg Arg Asp Arg Lys Ala
1545                1550                1555                1560

TAC GAT TGC ATG CTT CAA GAT CCT GGA AGT TTT AAC TTC GCG CCC CGC          5178
Tyr Asp Cys Met Leu Gln Asp Pro Gly Ser Phe Asn Phe Ala Pro Arg
                1565                1570                1575

CTG TTC ATC CTC AGC AGC TCC TCT GGG GAT TTT GCA GCC ACA GAG TTT          5226
Leu Phe Ile Leu Ser Ser Ser Ser Gly Asp Phe Ala Ala Thr Glu Phe
                1580                1585                1590

GTG TAC CCT GCC CGA GCC CCC TCT GTG GTC AGT TCC ATG CCC TTC CTG          5274
Val Tyr Pro Ala Arg Ala Pro Ser Val Val Ser Ser Met Pro Phe Leu
                1595                1600                1605

CAG GAA GAT CTG TAC AGC GCG CCC CAG CCA GCA CTT TTC CTT GTT GAC          5322
Gln Glu Asp Leu Tyr Ser Ala Pro Gln Pro Ala Leu Phe Leu Val Asp
                1610                1615                1620

AAT CAC CAC GAG GTG TAC CTC TGG CAA GGC TGG TGG CCC ATC GAG AAC          5370
Asn His His Glu Val Tyr Leu Trp Gln Gly Trp Trp Pro Ile Glu Asn
1625                1630                1635                1640

AAG ATC ACT GGT TCC GCC CGC ATC CGC TGG GCC TCC GAC CGG AAG AGT          5418
Lys Ile Thr Gly Ser Ala Arg Ile Arg Trp Ala Ser Asp Arg Lys Ser
                1645                1650                1655

GCG ATG GAG ACT GTG CTC CAG TAC TGC AAA GGA AAA AAT CTC AAG AAA          5466
Ala Met Glu Thr Val Leu Gln Tyr Cys Lys Gly Lys Asn Leu Lys Lys
                1660                1665                1670

CCA GCC CCC AAG TCT TAC CTT ATC CAC GCT GGT CTG GAG CCC CTG ACA          5514
Pro Ala Pro Lys Ser Tyr Leu Ile His Ala Gly Leu Glu Pro Leu Thr
                1675                1680                1685

TTC ACC AAT ATG TTT CCC AGC TGG GAG CAC AGA GAG GAC ATC GCT GAG          5562
Phe Thr Asn Met Phe Pro Ser Trp Glu His Arg Glu Asp Ile Ala Glu
                1690                1695                1700

ATC ACA GAG ATG GAC ACG GAA GTT TCC AAT CAG ATC ACC CTC GTG GAA          5610
```

```
                Ile Thr Glu Met Asp Thr Glu Val Ser Asn Gln Ile Thr Leu Val Glu
                1705                1710                1715                1720

GAC GTC TTA GCC AAG CTC TGT AAA ACC ATT TAC CCG CTG GCC GAC CTC          5658
Asp Val Leu Ala Lys Leu Cys Lys Thr Ile Tyr Pro Leu Ala Asp Leu
            1725                1730                1735

CTG GCC AGG CCA CTC CCG GAG GGG GTC GAT CCT CTG AAG CTT GAG ATC          5706
Leu Ala Arg Pro Leu Pro Glu Gly Val Asp Pro Leu Lys Leu Glu Ile
        1740                1745                1750

TAT CTC ACC GAC GAA GAC TTC GAG TTT GCA CTA GAC ATG ACG AGG GAT          5754
Tyr Leu Thr Asp Glu Asp Phe Glu Phe Ala Leu Asp Met Thr Arg Asp
        1755                1760                1765

GAA TAC AAC GCC CTG CCC GCC TGG AAG CAG GTG AAC CTG AAG AAA GCA          5802
Glu Tyr Asn Ala Leu Pro Ala Trp Lys Gln Val Asn Leu Lys Lys Ala
        1770                1775                1780

AAA GGC CTG TTC TGAGTGGGGA GACGCCAGAG GAGCCTCACG GTCACGTCCA ACAAC        5859
Lys Gly Leu Phe
1785

ACCACTGCAC CAGGGAAATG GATATATATT TTTGGACTGG TGTTTTTCAC AAAGTATTTT         5919

TCAATCAGAG TTTTCAGAAC CTGACATTGT TAAAGATACT GCTTGTCCCG GAGTTGTGTA         5979

TTTTGTAAAT GTTCAAGGGA ACTGTTTGGA AACTTCTTTC CACCATTCAG GAGGTTATCA         6039

GAATTAATAA AAGTATCTGT TATGTGCACT TAAGCCGCAG CTGCTATAGA TAGCACTGCC         6099

TTCTTGTTCC AGCTAGGCAA TGCCTTTTTT TTTTTTTTG AAGCAGTTCT CTTTATAAAG          6159

TGTTATTTTG ATAGTTTGTG GATTCTAAAA TATATATATA TTTATATAAA CACCATATAA         6219

GTCAAATATG TATTTAACAA AGCAATATGT ATTCATTCAC TTTCAAGATT TGTTTTGGTG         6279

TCAAAATAAC ATGAAAAGGT AGATGGAGTT GCTTCTGTTG AATTAGCTCT GCCACCAATA         6339

TGTATCTTCA TACACGTTTG GAAATGTTTC CTGCAGCATT AGGTATGACT TGTTCTGAGT         6399

ACTGCTTCCG GTGCTAAAAT GAACAAAGAA TTTGTACTTA ATGGCATGGA CTCTGGAGAA         6459

TCTATGCGAA TCAACCTTTC TACCTTAATA TCTCCCCAAA AATGTATAGT GCCTTGTTTT         6519

TATGTACAGT TTATATACAG AAAAGTTTGC TCTGCATTTT TGATGATGGT TTGGAACATT         6579

ATCTACAATT TTACTCTCAA ATAGTCAAAA TAAAAACATC TCAATTTCTA ATACCGGTTG         6639

TAAACAAACA GTACACATGT CATTTTGTGA TATAGGACTC CCAAATAAAA GTATCAGAAT         6699

AAACACAACA ATTAACTGG                                                     6718

(2) INFORMATION FOR SEQ ID NO:2:

(i) SEQUENCE CHARACTERISTICS:
        (A) LENGTH: 1788 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

Met Lys Arg Lys Glu Arg Ile Ala Arg Arg Leu Glu Gly Ile Glu Asn
 1               5                  10                  15

Asp Thr Gln Pro Ile Leu Leu Gln Ser Cys Thr Gly Leu Val Thr His
            20                  25                  30

Arg Leu Leu Glu Glu Asp Thr Pro Arg Tyr Met Arg Ala Ser Asp Pro
        35                  40                  45

Ala Ser Pro His Ile Gly Arg Ser Asn Glu Glu Glu Thr Ser Asp
    50                  55                  60

Ser Ser Leu Glu Lys Gln Thr Arg Ser Lys Tyr Cys Thr Glu Thr Ser
```

-continued

```
                65                  70                  75                  80
Gly Val His Gly Asp Ser Pro Tyr Gly Ser Gly Thr Met Asp Thr His
                    85                  90                  95
Ser Leu Glu Ser Lys Ala Glu Arg Ile Ala Arg Tyr Lys Ala Glu Arg
                   100                 105                 110
Arg Arg Gln Leu Ala Glu Lys Tyr Gly Leu Thr Leu Asp Pro Glu Ala
                   115                 120                 125
Asp Ser Glu Tyr Leu Ser Arg Tyr Thr Lys Ser Arg Lys Glu Pro Asp
                   130                 135                 140
Ala Val Glu Lys Arg Gly Gly Lys Ser Asp Lys Gln Glu Glu Ser Ser
145                 150                 155                 160
Arg Asp Ala Ser Ser Leu Tyr Pro Gly Thr Glu Thr Met Gly Leu Arg
                   165                 170                 175
Thr Cys Ala Gly Glu Ser Lys Asp Tyr Ala Leu His Ala Gly Asp Gly
                   180                 185                 190
Ser Ser Asp Pro Glu Val Leu Leu Asn Ile Glu Asn Gln Arg Arg Gly
                   195                 200                 205
Gln Glu Leu Ser Ala Thr Arg Gln Ala His Asp Leu Ser Pro Ala Ala
                   210                 215                 220
Glu Ser Ser Ser Thr Phe Ser Phe Ser Gly Arg Asp Ser Ser Phe Thr
225                 230                 235                 240
Glu Val Pro Arg Ser Pro Lys His Ala His Ser Ser Ser Leu Gln Gln
                   245                 250                 255
Ala Ala Ser Arg Ser Pro Ser Phe Gly Asp Pro Gln Leu Ser Pro Glu
                   260                 265                 270
Ala Arg Pro Arg Cys Thr Ser His Ser Glu Thr Pro Thr Val Asp Asp
                   275                 280                 285
Glu Glu Lys Val Asp Glu Arg Ala Lys Leu Ser Val Ala Ala Lys Arg
                   290                 295                 300
Leu Leu Phe Arg Glu Met Glu Lys Ser Phe Asp Glu Gln Asn Val Pro
305                 310                 315                 320
Lys Arg Arg Ser Arg Asn Thr Ala Val Glu Gln Arg Leu Arg Arg Leu
                   325                 330                 335
Gln Asp Arg Ser Leu Thr Gln Pro Ile Thr Thr Glu Glu Val Val Ile
                   340                 345                 350
Ala Ala Thr Leu Gln Ala Ser Ala His Gln Lys Ala Leu Ala Lys Asp
                   355                 360                 365
Gln Thr Asn Glu Gly Lys Glu Leu Ala Glu Gln Gly Glu Pro Asp Ser
                   370                 375                 380
Ser Thr Leu Ser Leu Ala Glu Lys Leu Ala Leu Phe Asn Lys Leu Ser
385                 390                 395                 400
Gln Pro Val Ser Lys Ala Ile Ser Thr Arg Asn Arg Ile Asp Thr Arg
                   405                 410                 415
Gln Arg Arg Met Asn Ala Arg Tyr Gln Thr Gln Pro Val Thr Leu Gly
                   420                 425                 430
Glu Val Glu Gln Val Gln Ser Gly Lys Leu Ile Pro Phe Ser Pro Ala
                   435                 440                 445
Val Asn Thr Ser Val Ser Thr Val Ala Ser Thr Val Ala Pro Met Tyr
                   450                 455                 460
Ala Gly Asp Leu Arg Thr Lys Pro Pro Leu Asp His Asn Ala Ser Ala
465                 470                 475                 480
Thr Asp Tyr Lys Phe Ser Ser Ile Glu Asn Ser Asp Ser Pro Val
                   485                 490                 495
```

-continued

```
Arg Ser Ile Leu Lys Ser Gln Ala Trp Gln Pro Leu Val Glu Gly Ser
            500                 505                 510

Glu Asn Lys Gly Met Leu Arg Glu Tyr Gly Glu Thr Glu Ser Lys Arg
        515                 520                 525

Ala Leu Thr Gly Arg Asp Ser Gly Met Glu Lys Tyr Gly Ser Phe Glu
    530                 535                 540

Glu Ala Glu Ala Ser Tyr Pro Ile Leu Asn Arg Ala Arg Glu Gly Asp
545                 550                 555                 560

Ser His Lys Glu Ser Lys Tyr Ala Val Pro Arg Arg Gly Ser Leu Glu
            565                 570                 575

Arg Ala Asn Pro Pro Ile Thr His Leu Gly Asp Glu Pro Lys Glu Phe
        580                 585                 590

Ser Met Ala Lys Met Asn Ala Gln Gly Asn Leu Asp Leu Arg Asp Arg
    595                 600                 605

Leu Pro Phe Glu Glu Lys Val Glu Val Glu Asn Val Met Lys Arg Lys
610                 615                 620

Phe Ser Leu Arg Ala Ala Glu Phe Gly Glu Pro Thr Ser Glu Gln Thr
625                 630                 635                 640

Gly Thr Ala Ala Gly Lys Thr Ile Ala Gln Thr Thr Ala Pro Val Ser
            645                 650                 655

Trp Lys Pro Gln Asp Ser Ser Glu Gln Pro Gln Glu Lys Leu Cys Lys
        660                 665                 670

Asn Pro Cys Ala Met Phe Ala Ala Gly Glu Ile Lys Thr Pro Thr Gly
    675                 680                 685

Glu Gly Leu Leu Asp Ser Pro Ser Lys Thr Met Ser Ile Lys Glu Arg
690                 695                 700

Leu Ala Leu Leu Lys Lys Ser Gly Glu Glu Asp Trp Arg Asn Arg Leu
705                 710                 715                 720

Ser Arg Arg Gln Glu Gly Gly Lys Ala Pro Ala Ser Ser Leu His Thr
            725                 730                 735

Gln Glu Ala Gly Arg Ser Leu Ile Lys Lys Arg Val Thr Glu Ser Arg
        740                 745                 750

Glu Ser Gln Met Thr Ile Glu Glu Arg Lys Gln Leu Ile Thr Val Arg
    755                 760                 765

Glu Glu Ala Trp Lys Thr Arg Gly Arg Gly Ala Ala Asn Asp Ser Thr
770                 775                 780

Gln Phe Thr Val Ala Gly Arg Met Val Lys Lys Gly Leu Ala Ser Pro
785                 790                 795                 800

Thr Ala Ile Thr Pro Val Ala Ser Ala Ile Cys Gly Lys Thr Arg Gly
            805                 810                 815

Thr Thr Pro Val Ser Lys Pro Leu Glu Asp Ile Glu Ala Arg Pro Asp
        820                 825                 830

Met Gln Leu Glu Ser Asp Leu Lys Leu Asp Arg Leu Glu Thr Phe Leu
    835                 840                 845

Arg Arg Leu Asn Asn Lys Val Gly Gly Met His Glu Thr Val Leu Thr
850                 855                 860

Val Thr Gly Lys Ser Val Lys Glu Val Met Lys Pro Asp Asp Asp Glu
865                 870                 875                 880

Thr Phe Ala Lys Phe Tyr Arg Ser Val Asp Tyr Asn Met Pro Arg Ser
            885                 890                 895

Pro Val Glu Met Asp Glu Asp Phe Asp Val Ile Phe Asp Pro Tyr Ala
        900                 905                 910

Pro Lys Leu Thr Ser Ser Val Ala Glu His Lys Arg Ala Val Arg Pro
    915                 920                 925
```

Lys Arg Arg Val Gln Ala Ser Lys Asn Pro Leu Lys Met Leu Ala Ala
            930                 935                 940

Arg Glu Asp Leu Leu Gln Glu Tyr Thr Gln Arg Leu Asn Val Ala
945                 950                 955                 960

Phe Met Glu Ser Lys Arg Met Lys Val Glu Lys Met Ser Ser Asn Ser
                965                 970                 975

Asn Phe Ser Glu Val Thr Leu Ala Gly Leu Ala Ser Lys Glu Asn Phe
            980                 985                 990

Ser Asn Val Ser Leu Arg Ser Val Asn Leu Thr Glu Gln Asn Ser Asn
            995                1000                1005

Asn Ser Ala Val Pro Tyr Lys Arg Leu Met Leu Leu Gln Ile Lys Gly
        1010                1015                1020

Arg Arg His Val Gln Thr Arg Leu Val Glu Pro Arg Ala Ser Ala Leu
025                 1030                1035                1040

Asn Ser Gly Asp Cys Phe Leu Leu Ser Pro His Cys Cys Phe Leu
            1045                1050                1055

Trp Val Gly Glu Phe Ala Asn Val Ile Glu Lys Ala Lys Ala Ser Glu
            1060                1065                1070

Leu Ala Thr Leu Ile Gln Thr Lys Arg Glu Leu Gly Cys Arg Ala Thr
        1075                1080                1085

Tyr Ile Gln Thr Ile Glu Glu Gly Ile Asn Thr His Thr His Ala Ala
        1090                1095                1100

Lys Asp Phe Trp Lys Leu Leu Gly Gly Gln Thr Ser Tyr Gln Ser Ala
105                 1110                1115                1120

Gly Asp Pro Lys Glu Asp Glu Leu Tyr Glu Ala Ala Ile Ile Glu Thr
                1125                1130                1135

Asn Cys Ile Tyr Arg Leu Met Asp Asp Lys Leu Val Pro Asp Asp
            1140                1145                1150

Tyr Trp Gly Lys Ile Pro Lys Cys Ser Leu Leu Gln Pro Lys Glu Val
        1155                1160                1165

Leu Val Phe Asp Phe Gly Ser Glu Val Tyr Val Trp His Gly Lys Glu
        1170                1175                1180

Val Thr Leu Ala Gln Arg Lys Ile Ala Phe Gln Leu Ala Lys His Leu
185                 1190                1195                1200

Trp Asn Gly Thr Phe Asp Tyr Glu Asn Cys Asp Ile Asn Pro Leu Asp
            1205                1210                1215

Pro Gly Glu Cys Asn Pro Leu Ile Pro Arg Lys Gly Gln Gly Arg Pro
            1220                1225                1230

Asp Trp Ala Ile Phe Gly Arg Leu Thr Glu His Asn Glu Thr Ile Leu
        1235                1240                1245

Phe Lys Glu Lys Phe Leu Asp Trp Thr Glu Leu Lys Arg Ser Asn Glu
        1250                1255                1260

Lys Asn Pro Gly Glu Leu Ala Gln His Lys Glu Asp Pro Arg Thr Asp
265                 1270                1275                1280

Val Lys Ala Tyr Asp Val Thr Arg Met Val Ser Met Pro Gln Thr Thr
                1285                1290                1295

Ala Gly Thr Ile Leu Asp Gly Val Asn Val Gly Arg Gly Tyr Gly Leu
            1300                1305                1310

Val Glu Gly His Asp Arg Arg Gln Phe Glu Ile Thr Ser Val Ser Val
        1315                1320                1325

Asp Val Trp His Ile Leu Glu Phe Asp Tyr Ser Arg Leu Pro Lys Gln
        1330                1335                1340

Ser Ile Gly Gln Phe His Glu Gly Asp Ala Tyr Val Val Lys Trp Lys

```
     345              1350               1355                1360

Phe Met Val Ser Thr Ala Val Gly Ser Arg Gln Lys Gly Glu His Ser
            1365                1370                1375

Val Arg Ala Ala Gly Lys Glu Lys Cys Val Tyr Phe Phe Trp Gln Gly
        1380                1385                1390

Arg His Ser Thr Val Ser Glu Lys Gly Thr Ser Ala Leu Met Thr Val
    1395                1400                1405

Glu Leu Asp Glu Glu Arg Gly Ala Gln Val Gln Val Leu Gln Gly Lys
1410                1415                1420

Glu Pro Pro Cys Phe Leu Gln Cys Phe Gln Gly Met Val Val His
 425                1430                1435                1440

Ser Gly Arg Arg Glu Glu Glu Glu Asn Val Gln Ser Glu Trp Arg
            1445                1450                1455

Leu Tyr Cys Val Arg Gly Glu Val Pro Val Glu Gly Asn Leu Leu Glu
        1460                1465                1470

Val Ala Cys His Cys Ser Ser Leu Arg Ser Arg Thr Ser Met Val Val
    1475                1480                1485

Leu Asn Val Asn Lys Ala Leu Ile Tyr Leu Trp His Gly Cys Lys Ala
1490                1495                1500

Gln Ala His Thr Lys Glu Val Gly Arg Thr Ala Ala Asn Lys Ile Lys
 505                1510                1515                1520

Glu Gln Cys Pro Leu Glu Ala Gly Leu His Ser Ser Ser Lys Val Thr
            1525                1530                1535

Ile His Glu Cys Asp Glu Gly Ser Glu Pro Leu Gly Phe Trp Asp Ala
        1540                1545                1550

Leu Gly Arg Arg Asp Arg Lys Ala Tyr Asp Cys Met Leu Gln Asp Pro
    1555                1560                1565

Gly Ser Phe Asn Phe Ala Pro Arg Leu Phe Ile Leu Ser Ser Ser Ser
1570                1575                1580

Gly Asp Phe Ala Ala Thr Glu Phe Val Tyr Pro Ala Arg Ala Pro Ser
 585                1590                1595                1600

Val Val Ser Ser Met Pro Phe Leu Gln Glu Asp Leu Tyr Ser Ala Pro
            1605                1610                1615

Gln Pro Ala Leu Phe Leu Val Asp Asn His His Glu Val Tyr Leu Trp
        1620                1625                1630

Gln Gly Trp Trp Pro Ile Glu Asn Lys Ile Thr Gly Ser Ala Arg Ile
    1635                1640                1645

Arg Trp Ala Ser Asp Arg Lys Ser Ala Met Glu Thr Val Leu Gln Tyr
1650                1655                1660

Cys Lys Gly Lys Asn Leu Lys Lys Pro Ala Pro Lys Ser Tyr Leu Ile
 665                1670                1675                1680

His Ala Gly Leu Glu Pro Leu Thr Phe Thr Asn Met Phe Pro Ser Trp
            1685                1690                1695

Glu His Arg Glu Asp Ile Ala Glu Ile Thr Glu Met Asp Thr Glu Val
        1700                1705                1710

Ser Asn Gln Ile Thr Leu Val Glu Asp Val Leu Ala Lys Leu Cys Lys
    1715                1720                1725

Thr Ile Tyr Pro Leu Ala Asp Leu Leu Ala Arg Pro Leu Pro Glu Gly
1730                1735                1740

Val Asp Pro Leu Lys Leu Glu Ile Tyr Leu Thr Asp Glu Asp Phe Glu
 745                1750                1755                1760

Phe Ala Leu Asp Met Thr Arg Asp Glu Tyr Asn Ala Leu Pro Ala Trp
            1765                1770                1775
```

```
Lys Gln Val Asn Leu Lys Lys Ala Lys Gly Leu Phe
        1780                1785

(2) INFORMATION FOR SEQ ID NO:3:

(i) SEQUENCE CHARACTERISTICS:
        (A) LENGTH: 6463 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 201...5576

(xi) SEQUENCE DESCRIPTION: SEQ ID NO:3:

ATTTGAACAA GAAAAACTTA AGCCTCGTTG GATTCCCGTG TCAAAGGAAA GTTCCAAGCT         60

TTCAGAAAGA GTTCTTGCTT GAAGACAAAG AACAGCTTGA TAACCACAAA AGAAGGATCG       120

ATGCTCAGCT TTTAGCTGCC CTTCCTAAAG TTGCAGAATT AAGAAAAATC TTTGAACCAA       180

AGAGGAAAGA ATTTTTAGAA ATG AAA AGA AAA GAA AGA ATT GCC CGG CGC          230
                       Met Lys Arg Lys Glu Arg Ile Ala Arg Arg
                         1               5                  10

TTA GAA GGA ATT GAA ACC GAC ACG CAG CCC ATC CTC TTG CAG AGC TGC         278
Leu Glu Gly Ile Glu Thr Asp Thr Gln Pro Ile Leu Leu Gln Ser Cys
             15                  20                  25

ACG GGC TTG GTG ACT CAT CGC CTG CTG GAG GAG GAC ACA CCC AGA TAC         326
Thr Gly Leu Val Thr His Arg Leu Leu Glu Glu Asp Thr Pro Arg Tyr
         30                  35                  40

ATG CGT GCC ACA GAC CCG GCC AGC CCG CAC ATT GGT CGA TCA AAT GAA         374
Met Arg Ala Thr Asp Pro Ala Ser Pro His Ile Gly Arg Ser Asn Glu
     45                  50                  55

GAA GAA GAA ACT TCA GAT TCT TCA CTA GAA AAG CAG ACT CGA TCC AAA         422
Glu Glu Glu Thr Ser Asp Ser Ser Leu Glu Lys Gln Thr Arg Ser Lys
 60                  65                  70

CAG TGC ACA GAA ACC TCA GGC ATC CAT GCT GAC TCG CCC TAC AGT TCA         470
Gln Cys Thr Glu Thr Ser Gly Ile His Ala Asp Ser Pro Tyr Ser Ser
 75                  80                  85                  90

GGC ATC ATG GAC ACC CAG AGC CTC GAG TCC AAA GCC GAA AGA ATC GCC         518
Gly Ile Met Asp Thr Gln Ser Leu Glu Ser Lys Ala Glu Arg Ile Ala
                 95                 100                 105

AGG TAC AAA GCA GAG AGA AGA CGG CAG CTG GCA GAA AAG TAT GGG CTC         566
Arg Tyr Lys Ala Glu Arg Arg Arg Gln Leu Ala Glu Lys Tyr Gly Leu
             110                 115                 120

ACC CTG GAT CCG GAA GCA GAC TCT GAA ACT CCA TCT CGA TAC AGC AGG         614
Thr Leu Asp Pro Glu Ala Asp Ser Glu Thr Pro Ser Arg Tyr Ser Arg
         125                 130                 135

TCC AGA AAG GAC CCC GAG GCT GCG GAG AAA AGG GGA GTA AGA AGC GAG         662
Ser Arg Lys Asp Pro Glu Ala Ala Glu Lys Arg Gly Val Arg Ser Glu
     140                 145                 150

CGA TCG GCC AAG TCC AGC AGA GAC GCC GGC TCA TCC TAC TCC AGG ACT         710
Arg Ser Ala Lys Ser Ser Arg Asp Ala Gly Ser Ser Tyr Ser Arg Thr
155                 160                 165                 170

GAG CTC TCG GGG CTC AGG ACC TGC GTG GCT GAG TCC AAG GAC TAT GGC         758
Glu Leu Ser Gly Leu Arg Thr Cys Val Ala Glu Ser Lys Asp Tyr Gly
                 175                 180                 185

CTG CAC CGG AGT GAC GGT GTT TCC GAC ACA GAG GTG CTG CTC AAT GCA         806
Leu His Arg Ser Asp Gly Val Ser Asp Thr Glu Val Leu Leu Asn Ala
             190                 195                 200

GAA AAC CAA AGA CGC GGT CAA GAG CCC AGT GCC ACC GGG CTG GCC CGA         854
Glu Asn Gln Arg Arg Gly Gln Glu Pro Ser Ala Thr Gly Leu Ala Arg
```

-continued

|     | 205 |     |     |     | 210 |     |     |     | 215 |     |     |     |     |      |
|-----|-----|-----|-----|-----|-----|-----|-----|-----|-----|-----|-----|-----|-----|------|
| GAC | CTG | CCC | CTT | GCA | GGG | GAG | GTC | TCC | TCT | TCT | TTC | TCA | TTC | TCC GGG | 902 |
| Asp | Leu | Pro | Leu | Ala | Gly | Glu | Val | Ser | Ser | Ser | Phe | Ser | Phe | Ser Gly |
|     | 220 |     |     |     | 225 |     |     |     | 230 |     |     |     |     |      |

| CGA | GAC | TCT | GCC | CTC | GGT | GAA | GTG | CCA | AGG | TCC | CCA | AAG | GCA | GTG CAC | 950 |
| Arg | Asp | Ser | Ala | Leu | Gly | Glu | Val | Pro | Arg | Ser | Pro | Lys | Ala | Val His |
| 235 |     |     |     |     | 240 |     |     |     | 245 |     |     |     |     | 250  |

| AGC | CTG | CCC | AGT | CCA | TCG | CCT | GGG | CAG | CCG | GCC | TCC | CCA | AGC | CAC TCC | 998 |
| Ser | Leu | Pro | Ser | Pro | Ser | Pro | Gly | Gln | Pro | Ala | Ser | Pro | Ser | His Ser |
|     |     |     |     | 255 |     |     |     |     | 260 |     |     |     | 265 |      |

| ACC | AGT | GAC | CTG | CCA | CTC | CCT | GCG | GAG | GCT | CGA | GCC | AGG | TCA | ACT TCA | 1046 |
| Thr | Ser | Asp | Leu | Pro | Leu | Pro | Ala | Glu | Ala | Arg | Ala | Arg | Ser | Thr Ser |
|     |     |     | 270 |     |     |     | 275 |     |     |     |     | 280 |     |      |

| AAT | TCA | GAA | ATG | CCA | GCT | GCC | GAG | GAT | GAA | GAA | AAG | GTC | GAT | GAG CGA | 1094 |
| Asn | Ser | Glu | Met | Pro | Ala | Ala | Glu | Asp | Glu | Glu | Lys | Val | Asp | Glu Arg |
|     | 285 |     |     |     |     | 290 |     |     |     |     | 295 |     |     |      |

| GCG | AGG | CTG | AGC | GTC | GCT | GCT | AAG | AGG | CTG | CTC | TTC | AGG | GAG | ATG GAG | 1142 |
| Ala | Arg | Leu | Ser | Val | Ala | Ala | Lys | Arg | Leu | Leu | Phe | Arg | Glu | Met Glu |
|     | 300 |     |     |     | 305 |     |     |     |     | 310 |     |     |     |      |

| AAG | TCG | TTT | GAC | GAG | AAG | AGC | GTC | CCA | AAG | CGC | CGC | TCC | CGC | AAT GCG | 1190 |
| Lys | Ser | Phe | Asp | Glu | Lys | Ser | Val | Pro | Lys | Arg | Arg | Ser | Arg | Asn Ala |
| 315 |     |     |     |     | 320 |     |     |     | 325 |     |     |     |     | 330  |

| GCC | GTG | GAG | CAG | AGG | CTG | CGG | CGC | CTC | CAG | GAC | CGG | TCC | CAC | ACG CAG | 1238 |
| Ala | Val | Glu | Gln | Arg | Leu | Arg | Arg | Leu | Gln | Asp | Arg | Ser | His | Thr Gln |
|     |     |     |     | 335 |     |     |     |     | 340 |     |     |     | 345 |      |

| CCC | GTC | ACC | ACC | GAG | GAG | GTG | GTC | ATT | GCA | GCC | ACA | TTG | CAG | GCG TCT | 1286 |
| Pro | Val | Thr | Thr | Glu | Glu | Val | Val | Ile | Ala | Ala | Thr | Leu | Gln | Ala Ser |
|     |     |     | 350 |     |     |     | 355 |     |     |     |     | 360 |     |      |

| GCT | CAC | CAA | AAG | GCA | CTA | GCC | AGA | GAC | CAG | ACA | AAC | GAG | AGC | AAA GAT | 1334 |
| Ala | His | Gln | Lys | Ala | Leu | Ala | Arg | Asp | Gln | Thr | Asn | Glu | Ser | Lys Asp |
|     |     | 365 |     |     |     |     | 370 |     |     |     | 375 |     |     |      |

| TCT | GCT | GAG | CAG | GGA | GAA | CCT | GAC | TCC | TCC | ACT | CTG | AGC | TTA | GCG GAG | 1382 |
| Ser | Ala | Glu | Gln | Gly | Glu | Pro | Asp | Ser | Ser | Thr | Leu | Ser | Leu | Ala Glu |
|     | 380 |     |     |     |     | 385 |     |     |     |     | 390 |     |     |      |

| AAG | CTG | GCC | TTG | TTT | AAC | AAA | CTA | TCT | CAG | CCG | GTC | TCA | AAA | GCC ATT | 1430 |
| Lys | Leu | Ala | Leu | Phe | Asn | Lys | Leu | Ser | Gln | Pro | Val | Ser | Lys | Ala Ile |
| 395 |     |     |     |     | 400 |     |     |     |     | 405 |     |     |     | 410  |

| TCA | ACA | CGG | AAC | AGA | TTA | GAC | ATG | AGA | CAG | AGG | AGG | ATG | AAT | GCT CGT | 1478 |
| Ser | Thr | Arg | Asn | Arg | Leu | Asp | Met | Arg | Gln | Arg | Arg | Met | Asn | Ala Arg |
|     |     |     | 415 |     |     |     |     | 420 |     |     |     |     | 425 |      |

| TAT | CAA | ACC | CAG | CCG | GTC | ACG | CTT | GGA | GAA | GTG | GAA | CAG | GTG | CAG AGT | 1526 |
| Tyr | Gln | Thr | Gln | Pro | Val | Thr | Leu | Gly | Glu | Val | Glu | Gln | Val | Gln Ser |
|     |     |     | 430 |     |     |     | 435 |     |     |     |     | 440 |     |      |

| GGC | AAG | CTC | ATG | GCT | TTC | TCT | CCC | ACC | ATT | AAC | ACT | TCC | GTG | TCC ACC | 1574 |
| Gly | Lys | Leu | Met | Ala | Phe | Ser | Pro | Thr | Ile | Asn | Thr | Ser | Val | Ser Thr |
|     |     | 445 |     |     |     |     | 450 |     |     |     | 455 |     |     |      |

| GTG | GCA | TCT | ACC | GTC | CCC | CCC | ATG | TAT | GCA | GGA | AAT | CTT | CGG | ACA AAG | 1622 |
| Val | Ala | Ser | Thr | Val | Pro | Pro | Met | Tyr | Ala | Gly | Asn | Leu | Arg | Thr Lys |
|     | 460 |     |     |     |     | 465 |     |     |     |     | 470 |     |     |      |

| CCA | CTT | CCA | GAT | GAC | AGC | TTT | GGT | GCC | ACT | GAG | CAG | AAG | TTT | GCT TCT | 1670 |
| Pro | Leu | Pro | Asp | Asp | Ser | Phe | Gly | Ala | Thr | Glu | Gln | Lys | Phe | Ala Ser |
| 475 |     |     |     |     | 480 |     |     |     | 485 |     |     |     |     | 490  |

| TCG | CTA | GAA | AAC | TCC | GAC | TCC | CCA | GTT | AGA | AGC | ATC | CTG | AAA | TCC CAA | 1718 |
| Ser | Leu | Glu | Asn | Ser | Asp | Ser | Pro | Val | Arg | Ser | Ile | Leu | Lys | Ser Gln |
|     |     |     | 495 |     |     |     |     | 500 |     |     |     | 505 |     |      |

| GGC | TGG | CAG | CCC | TCG | GTC | GAG | GGT | GCT | GGG | AGC | AAA | GCA | ATG | TTG AGA | 1766 |
| Gly | Trp | Gln | Pro | Ser | Val | Glu | Gly | Ala | Gly | Ser | Lys | Ala | Met | Leu Arg |
|     |     |     | 510 |     |     |     |     | 515 |     |     |     | 520 |     |      |

| GAA | TTT | GAA | GAG | ACA | GAA | CGC | AAG | GGA | GGC | TTG | ACA | GGT | GGA | GAT GGC | 1814 |
| Glu | Phe | Glu | Glu | Thr | Glu | Arg | Lys | Gly | Gly | Leu | Thr | Gly | Gly | Asp Gly |

```
                   525                 530                 535
GGG GTT ACA AAG TAT GGG TCC TTC GAG GAA GCA GAG CTG TCC TAC CCC      1862
Gly Val Thr Lys Tyr Gly Ser Phe Glu Glu Ala Glu Leu Ser Tyr Pro
        540                 545                 550

GTC CTC AGC AGA GTC CGG GAG GGA GAC AAC CAT AAA GAG GCC ATC TAT      1910
Val Leu Ser Arg Val Arg Glu Gly Asp Asn His Lys Glu Ala Ile Tyr
555                 560                 565                 570

GCC CTT CCG AGG AAA GGA AGC CTG GAG CTC GCC CAT CCT CCC ATC GCC      1958
Ala Leu Pro Arg Lys Gly Ser Leu Glu Leu Ala His Pro Pro Ile Ala
                575                 580                 585

CAG CTT GGT GAT GAC CTG AAG GAA TTT TCC ACC CCA AAG AGC ACC ATG      2006
Gln Leu Gly Asp Asp Leu Lys Glu Phe Ser Thr Pro Lys Ser Thr Met
            590                 595                 600

CAG GCA AGC CCA GAC TGG AAG GAG AGG CAG CTC TTT GAA GAG AAG GTG      2054
Gln Ala Ser Pro Asp Trp Lys Glu Arg Gln Leu Phe Glu Glu Lys Val
        605                 610                 615

GAC TTG GAG AAT GTC ACA AAG AGG AAG TTT TCG CTG AAA GCC GCG GAG      2102
Asp Leu Glu Asn Val Thr Lys Arg Lys Phe Ser Leu Lys Ala Ala Glu
    620                 625                 630

TTC GGG GAA CCC ACT TCT GAG CAG ACC GGC GCG GCT GCT GGG AAA CCG      2150
Phe Gly Glu Pro Thr Ser Glu Gln Thr Gly Ala Ala Ala Gly Lys Pro
635                 640                 645                 650

GCT GCT CCG ACT GCA ACC CCG GTG TCC TGG AAG CCG CAG GAT CCC TCC      2198
Ala Ala Pro Thr Ala Thr Pro Val Ser Trp Lys Pro Gln Asp Pro Ser
                655                 660                 665

GAA CAG CCT CAG GAG AAG CGG TAT CAG AGC CCG TGT GCG ATG TTT GCT      2246
Glu Gln Pro Gln Glu Lys Arg Tyr Gln Ser Pro Cys Ala Met Phe Ala
            670                 675                 680

GCT GGA GAG ATC AAA GCC CCG GCG GTG GAG GGC AGC CTC GAC TCC CCC      2294
Ala Gly Glu Ile Lys Ala Pro Ala Val Glu Gly Ser Leu Asp Ser Pro
        685                 690                 695

AGC AAA ACC ATG TCC ATT AAA GAA AGA TTA GCA CTG TTG AAG AAG AGC      2342
Ser Lys Thr Met Ser Ile Lys Glu Arg Leu Ala Leu Leu Lys Lys Ser
    700                 705                 710

GGT GAG GAA GAC TGG AGA AAC AGA CTC AAC AGA AAG CAG GAA TAC GGC      2390
Gly Glu Glu Asp Trp Arg Asn Arg Leu Asn Arg Lys Gln Glu Tyr Gly
715                 720                 725                 730

AAA GCC TCC ATC ACC AGC AGC CTG CAC ATC CAA GAG ACG GAG CAG TCA      2438
Lys Ala Ser Ile Thr Ser Ser Leu His Ile Gln Glu Thr Glu Gln Ser
                735                 740                 745

CTC AAG AAG AAG CGG GTC ACA GAA AGT CGA GAG AGC CAG ATG ACT ATT      2486
Leu Lys Lys Lys Arg Val Thr Glu Ser Arg Glu Ser Gln Met Thr Ile
            750                 755                 760

GAA GAG AGA AAG CAT CTC ATC ACC GTG AGA GAG GAC GCC TGG AAG ACC      2534
Glu Glu Arg Lys His Leu Ile Thr Val Arg Glu Asp Ala Trp Lys Thr
        765                 770                 775

AGG GGC AAA GGA GCA GCC AAC GAC TCT ACC CAG TTT ACT GTG GCC GGC      2582
Arg Gly Lys Gly Ala Ala Asn Asp Ser Thr Gln Phe Thr Val Ala Gly
    780                 785                 790

AGG ATG GTG AAG CGA GGT CTG GCG TCC CCC ACT GCC ATC ACC CCG GTA      2630
Arg Met Val Lys Arg Gly Leu Ala Ser Pro Thr Ala Ile Thr Pro Val
795                 800                 805                 810

GCA TCC CCT GTT TCC AGC AAA GCA AGG GGC ACT ACA CCA GTT TCC AGA      2678
Ala Ser Pro Val Ser Ser Lys Ala Arg Gly Thr Thr Pro Val Ser Arg
                815                 820                 825

CCC CTG GAA GAT ATC GAA GCC AGA CCA GAC ATG CAG TTA GAG TCG GAC      2726
Pro Leu Glu Asp Ile Glu Ala Arg Pro Asp Met Gln Leu Glu Ser Asp
            830                 835                 840

CTC AAG CTG GAC AGG CTG GAA ACC TTC CTA AGA AGG CTG AAT AAC AAA      2774
Leu Lys Leu Asp Arg Leu Glu Thr Phe Leu Arg Arg Leu Asn Asn Lys
```

-continued

```
                 845                 850                 855
GTT GGT GGG ATG CAA GAA ACA GTC CTC ACT GTC ACT GGG AAA TCG GTG   2822
Val Gly Gly Met Gln Glu Thr Val Leu Thr Val Thr Gly Lys Ser Val
            860                 865                 870

AAA GAG GTG ATG AAG CCG GAC GAT GAT GAA ACC TTT GCC AAG TTT TAC   2870
Lys Glu Val Met Lys Pro Asp Asp Asp Glu Thr Phe Ala Lys Phe Tyr
875                 880                 885                 890

CGC AGC GTG GAC TCC TCT CTA CCG AGA AGC CCC GTA GAG CTG GAC GAG   2918
Arg Ser Val Asp Ser Ser Leu Pro Arg Ser Pro Val Glu Leu Asp Glu
                895                 900                 905

GAT TTC GAT GTC ATT TTT GAT CCT TAT GCC CCC AGG TTG ACA TCC TCG   2966
Asp Phe Asp Val Ile Phe Asp Pro Tyr Ala Pro Arg Leu Thr Ser Ser
            910                 915                 920

GTG GCT GAG CAC AAG CGT GCC GTG CGG CCC AAG CGC CGG GTC CAG GCT   3014
Val Ala Glu His Lys Arg Ala Val Arg Pro Lys Arg Arg Val Gln Ala
        925                 930                 935

TCC AAA AAC CCC CTG AAG ATG CTG GCC GCG AGG GAA GAT CTC CTG CAG   3062
Ser Lys Asn Pro Leu Lys Met Leu Ala Ala Arg Glu Asp Leu Leu Gln
    940                 945                 950

GAG TAC ACT GAG CAG AGA CTG AAC GTG GCC TTC GTG GAG TCA AAG CGG   3110
Glu Tyr Thr Glu Gln Arg Leu Asn Val Ala Phe Val Glu Ser Lys Arg
955                 960                 965                 970

ATG AAA GTC GAA AAG TTG TCC GCC AAC TCC AGC TTC TCA GAA GTC ACC   3158
Met Lys Val Glu Lys Leu Ser Ala Asn Ser Ser Phe Ser Glu Val Thr
                975                 980                 985

CTG GCG GGG TTA GCC AGC AAA GAA AAC TTC AGC AAC GTC AGC CTG CGG   3206
Leu Ala Gly Leu Ala Ser Lys Glu Asn Phe Ser Asn Val Ser Leu Arg
            990                 995                 1000

AGC GTC AAC CTG ACG GAA CAG AAT TCC AAC AAC AGT GCA GTG CCC TAC   3254
Ser Val Asn Leu Thr Glu Gln Asn Ser Asn Asn Ser Ala Val Pro Tyr
        1005                1010                1015

AAG AAG CTG ATG CTG CTG CAG GTT AAA GGA AGA AGA CAC GTG CAG ACG   3302
Lys Lys Leu Met Leu Leu Gln Val Lys Gly Arg Arg His Val Gln Thr
    1020                1025                1030

CGG CTG GTG GAG CCT CGC GCC CCC TCC CTC AAC AGC GGG GAC TGC TTC   3350
Arg Leu Val Glu Pro Arg Ala Pro Ser Leu Asn Ser Gly Asp Cys Phe
1035                1040                1045                1050

CTC CTG CTC TCG CCC CAT CAC TGC TTC CTG TGG GTC GGA GAG TTC GCC   3398
Leu Leu Leu Ser Pro His His Cys Phe Leu Trp Val Gly Glu Phe Ala
                1055                1060                1065

AAC GTG ATC GAG AAG GCG AAG GCC TCA GAA CTT GCG AGT TTA ATT CAG   3446
Asn Val Ile Glu Lys Ala Lys Ala Ser Glu Leu Ala Ser Leu Ile Gln
            1070                1075                1080

ACC AAG AGG GAA CTT GGT TGT AGA GCA ACT TAC ATC CAG ACT GTT GAA   3494
Thr Lys Arg Glu Leu Gly Cys Arg Ala Thr Tyr Ile Gln Thr Val Glu
        1085                1090                1095

GAA GGA ATT AAT ACA CAC ACA CAT GCA GCC AAA GAC TTC TGG AAG CTT   3542
Glu Gly Ile Asn Thr His Thr His Ala Ala Lys Asp Phe Trp Lys Leu
    1100                1105                1110

CTG GGC GGC CAA GCC AGT TAC CAA TCC GCC GGA GAC CCA AAG GAG GAT   3590
Leu Gly Gly Gln Ala Ser Tyr Gln Ser Ala Gly Asp Pro Lys Glu Asp
1115                1120                1125                1130

GAG CTC TAT GAA ACG GCC ATA ATA GAG ACC AAC TGC ATT TAC CGT CTG   3638
Glu Leu Tyr Glu Thr Ala Ile Ile Glu Thr Asn Cys Ile Tyr Arg Leu
                1135                1140                1145

ATG GAT GAC AAA CTC GTT CCT GAT GAT GAC TAC TGG GGG AAG ATC CCA   3686
Met Asp Asp Lys Leu Val Pro Asp Asp Asp Tyr Trp Gly Lys Ile Pro
            1150                1155                1160

AAG TGC TCC CTC CTG CAA TCA AAA GAG GTA CTG GTG TTT GAT TTT GGG   3734
Lys Cys Ser Leu Leu Gln Ser Lys Glu Val Leu Val Phe Asp Phe Gly
```

```
              1165                1170                1175

AGT GAA GTT TAC GTG TGG CAT GGA AAA GAA GTC ACA TTA GCA CAA CGG      3782
Ser Glu Val Tyr Val Trp His Gly Lys Glu Val Thr Leu Ala Gln Arg
        1180                1185                1190

AAA ATC GCC TTT CAG CTG GCA AAG CAC TTG TGG AAT GGA ACC TTT GAC      3830
Lys Ile Ala Phe Gln Leu Ala Lys His Leu Trp Asn Gly Thr Phe Asp
1195                1200                1205                1210

TAC GAG AAT TGT GAC ATT AAC CCG CTG GAT CCT GGG GAA TGC AAT CCC      3878
Tyr Glu Asn Cys Asp Ile Asn Pro Leu Asp Pro Gly Glu Cys Asn Pro
            1215                1220                1225

CTC ATT CCC AGG AAA GGA CAG GGG CGG CCC GAC TGG GCA ATA TTT GGG      3926
Leu Ile Pro Arg Lys Gly Gln Gly Arg Pro Asp Trp Ala Ile Phe Gly
        1230                1235                1240

AGA CTT ACA GAA CAC AAT GAG ACG ATC TTG TTC AAA GAG AAA TTC CTT      3974
Arg Leu Thr Glu His Asn Glu Thr Ile Leu Phe Lys Glu Lys Phe Leu
        1245                1250                1255

GAT TGG ACG GAA CTG AAG AGA CCT AAC GAG AAG AAC GCC AGC GAA CTC      4022
Asp Trp Thr Glu Leu Lys Arg Pro Asn Glu Lys Asn Ala Ser Glu Leu
        1260                1265                1270

GCG CAG CAC AAG GAC GAT GCC CGG GCA GAG GTC AAG CCT TAC GAC GTG      4070
Ala Gln His Lys Asp Asp Ala Arg Ala Glu Val Lys Pro Tyr Asp Val
1275                1280                1285                1290

ACG CGG ATG GTG CCC GTG CCC CAG ACA ACA GCC GGC ACC GTG CTG GAT      4118
Thr Arg Met Val Pro Val Pro Gln Thr Thr Ala Gly Thr Val Leu Asp
            1295                1300                1305

GGG GTC AAC GTG GGC CGA GGC TAC GGG CTG GTG GAA GGG GAC GAC CGG      4166
Gly Val Asn Val Gly Arg Gly Tyr Gly Leu Val Glu Gly Asp Asp Arg
            1310                1315                1320

AGG CAG TTC GAG ATC GCC AGC ATC TCA GTG GAC GTC TGG CAC ATC CTG      4214
Arg Gln Phe Glu Ile Ala Ser Ile Ser Val Asp Val Trp His Ile Leu
        1325                1330                1335

GAG TTC GAC TAC AGC AGG CTC CCC AAG CAG AGC ATC GGG CAG TTC CAC      4262
Glu Phe Asp Tyr Ser Arg Leu Pro Lys Gln Ser Ile Gly Gln Phe His
        1340                1345                1350

GAA GGC GAT GCC TAC GTG GTG AAG TGG AAG TTC ATC GTG AGC ACT GCA      4310
Glu Gly Asp Ala Tyr Val Val Lys Trp Lys Phe Ile Val Ser Thr Ala
1355                1360                1365                1370

GTG GGA AGC CGG CAG AAG GGG GAG CAC TCG GTC AGG GTG GCT GGC AAA      4358
Val Gly Ser Arg Gln Lys Gly Glu His Ser Val Arg Val Ala Gly Lys
            1375                1380                1385

GAG AAA TGT GTC TAC TTC TTC TGG CAA GGC CGC CAG TCG ACC GTG AGT      4406
Glu Lys Cys Val Tyr Phe Phe Trp Gln Gly Arg Gln Ser Thr Val Ser
            1390                1395                1400

GAG AAG GGC ACA TCA GCT CTG ATG ACA GTG GAG CTG GAC GAG GAA AGG      4454
Glu Lys Gly Thr Ser Ala Leu Met Thr Val Glu Leu Asp Glu Glu Arg
        1405                1410                1415

GGG GCC CAG GTC CAG GTC CTG CAG GGC AAG GAG CCC CCC TGT TTC CTG      4502
Gly Ala Gln Val Gln Val Leu Gln Gly Lys Glu Pro Pro Cys Phe Leu
        1420                1425                1430

CAG TGC TTC CAG GGG GGG ATG GTG GTC CAC TCC GGG AGA CGG GAG GAG      4550
Gln Cys Phe Gln Gly Gly Met Val Val His Ser Gly Arg Arg Glu Glu
1435                1440                1445                1450

GAG GAA GAG AAC ACA CAG AGC GAG TGG CGG CTG TAC TGT GTG CGC GGA      4598
Glu Glu Glu Asn Thr Gln Ser Glu Trp Arg Leu Tyr Cys Val Arg Gly
            1455                1460                1465

GAG GTG CCT GTG GAG GGG AAC TTG CTG GAG GTG GCC TGT CAC TGC AGC      4646
Glu Val Pro Val Glu Gly Asn Leu Leu Glu Val Ala Cys His Cys Ser
            1470                1475                1480

AGC CTC AGG TCT AGG ACG TCC ATG GTT GTC CTC AAC GTC CAC AAA GCC      4694
Ser Leu Arg Ser Arg Thr Ser Met Val Val Leu Asn Val His Lys Ala
```

-continued

```
            1485                1490                1495

CTC ATC TAC CTG TGG CAT GGA TGC AAA GCC CAG GCC CAC ACG AAG GAG        4742
Leu Ile Tyr Leu Trp His Gly Cys Lys Ala Gln Ala His Thr Lys Glu
        1500                1505                1510

GTC GGA CGG ACT GCA GCC AAT AAA ATC AAG GAC CAA TGT CCC CTG GAG        4790
Val Gly Arg Thr Ala Ala Asn Lys Ile Lys Asp Gln Cys Pro Leu Glu
1515                1520                1525                1530

GCC GGG CTG CAC AGT AGC AGC AAA GTG ACA ATT CAT GAG TGT GAT GAA        4838
Ala Gly Leu His Ser Ser Ser Lys Val Thr Ile His Glu Cys Asp Glu
            1535                1540                1545

GGC TCG GAG CCC CTG GGG TTC TGG GAC GCT CTG GGG AGG AGA GAC CGG        4886
Gly Ser Glu Pro Leu Gly Phe Trp Asp Ala Leu Gly Arg Arg Asp Arg
        1550                1555                1560

AAA GCC TAC GAC TGC ATG CTT CAA GAT CCT GGA AAT TTT AAC TTC ACA        4934
Lys Ala Tyr Asp Cys Met Leu Gln Asp Pro Gly Asn Phe Asn Phe Thr
    1565                1570                1575

CCC CGC CTG TTC ATC CTC AGC AGC TCC TCT GGT GAC TTC TCA GCC ACA        4982
Pro Arg Leu Phe Ile Leu Ser Ser Ser Ser Gly Asp Phe Ser Ala Thr
        1580                1585                1590

GAG TTC ATG TAT CCC GCC CGA GAC CCC TCT GTG GTC AAC TCT ATG CCC        5030
Glu Phe Met Tyr Pro Ala Arg Asp Pro Ser Val Val Asn Ser Met Pro
1595                1600                1605                1610

TTC CTG CAG GAA GAC CTA TAC AGT GCC CCA CAG CCA GCA CTC TTC CTT        5078
Phe Leu Gln Glu Asp Leu Tyr Ser Ala Pro Gln Pro Ala Leu Phe Leu
            1615                1620                1625

GTT GAC AAT CAC CAC GAG GTG TAC CTC TGG CAA GGC TGG TGG CCC ATC        5126
Val Asp Asn His His Glu Val Tyr Leu Trp Gln Gly Trp Trp Pro Ile
        1630                1635                1640

GAG AAC AAG ATC ACG GGC TCC GCG CGC ATC CGC TGG GCC TCG GAC CGG        5174
Glu Asn Lys Ile Thr Gly Ser Ala Arg Ile Arg Trp Ala Ser Asp Arg
    1645                1650                1655

AAG AGC GCC ATG GAG ACA GTG CTG CAG TAC TGC CGA GGG AAA AAC CTG        5222
Lys Ser Ala Met Glu Thr Val Leu Gln Tyr Cys Arg Gly Lys Asn Leu
        1660                1665                1670

AAG AAG CCG CCC CCC AAG TCT TAC CTC ATC CAC GCT GGC CTG GAA CCC        5270
Lys Lys Pro Pro Pro Lys Ser Tyr Leu Ile His Ala Gly Leu Glu Pro
1675                1680                1685                1690

CTG ACC TTC ACC AAC ATG TTC CCC AGC TGG GAG CAC AGA GAA GAC ATT        5318
Leu Thr Phe Thr Asn Met Phe Pro Ser Trp Glu His Arg Glu Asp Ile
            1695                1700                1705

GCA GAG ATC ACG GAG ATG GAC ACG GAA GTT TCA AAT CAG ATC ACC CTA        5366
Ala Glu Ile Thr Glu Met Asp Thr Glu Val Ser Asn Gln Ile Thr Leu
        1710                1715                1720

GTG GAG GAT GTC TTA GCC AAA CTG TGT AAG ACC ATT TAC CCA CTG GCC        5414
Val Glu Asp Val Leu Ala Lys Leu Cys Lys Thr Ile Tyr Pro Leu Ala
    1725                1730                1735

GAC CTC CTA GCC AGG CCG CTC CCT GAG GGA GTT GAC CCT CTG AAG CTG        5462
Asp Leu Leu Ala Arg Pro Leu Pro Glu Gly Val Asp Pro Leu Lys Leu
    1740                1745                1750

GAG ATC TAT CTC ACC GAC GAG GAC TTC GAG TTT GCA CTA GAC ATG ACC        5510
Glu Ile Tyr Leu Thr Asp Glu Asp Phe Glu Phe Ala Leu Asp Met Thr
1755                1760                1765                1770

CGA GAC GAG TAC AAT GCA CTG CCC GCT TGG AAG CAG GTG AAC CTG AAG        5558
Arg Asp Glu Tyr Asn Ala Leu Pro Ala Trp Lys Gln Val Asn Leu Lys
            1775                1780                1785

AAA GCG AAA GGT CTG TTC TGAGTCAGGA GATGCTGGAG GAACCTGGGT GGTCACTT     5614
Lys Ala Lys Gly Leu Phe
            1790

TCAATACTGA TGGACCAGGA AAATGGATGT TTTAGTGGGG GAGCCTGGTA TTTTTAAATA     5674
```

```
TGTTTTTTCA TCTGCATTTT TAAAACCTGA AGTGACCAGC TCTCCTGCTT GTTTGGGAGT     5734

TGTGTATTTT GTAAATGTTC CAGAGAACTC TCTGGGAACA TGCTTTCCAC ACATCAGCAG     5794

GTGATGTTCG TGAGGTATCC GTGGCCCTAC ACGCACTTAT GCAGCAGGTC CTCAGTGGCG     5854

GCCACGGCAC CGCCCTCCCG CTCCAGCTCA GCGTTGCCTA TTTTTTTGAA GCAGTTCTCT     5914

TTATAAAGTG TTATTTTGAT AGTTTGTGGA TTCTAAAATA TATATATATT TATATAAACA     5974

CCATATAAAT CAAATATGTA TTTAACAAAC CAGTATGTAT TCATTCACTT TTAAGATTTT     6034

TTTTTTTTGG TGTCAAAATA ATATTAAAAG GCAGTTGCCT CTGTTGAGTT AGTTCTGCCA     6094

CCTGTGTGTA CTTTCACCCA CGTTCAGAAG CGTCTCCTTT GGTGTGAAGT CTGACTCGTT     6154

CTGAGTGCTG CTTCCGGTGC TAAGATGAAC AAAGGCTCTT AAGAATCTGT GCGAATCCAC     6214

CTTTCTACCT TAATATCGCC CCCAAATGTA TAGTGCCTTG TTTTATGTAC AGTTTATATA     6274

CAGAAAAGTT TGCTCTGCAT TTTTTGACGA TGGTTTGGAA CAGTATCTAC AATTTTACTC     6334

TAAAATAGTA GAAATTTCGA AAAAAAAAAA AAYYAACTCT ATTTCTAATA CCTGTTGTAA     6394

ACATTATACA TGTCATTTGG TGACGGAGGA ATCCAAAATA AAAGCTTCAG AATAAACACA     6454

ACTTAAAAA                                                              6463
```

(2) INFORMATION FOR SEQ ID NO:4:

(i) SEQUENCE CHARACTERISTICS:
        (A) LENGTH: 1792 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

```
Met Lys Arg Lys Glu Arg Ile Ala Arg Arg Leu Glu Gly Ile Glu Thr
  1               5                  10                  15

Asp Thr Gln Pro Ile Leu Leu Gln Ser Cys Thr Gly Leu Val Thr His
                 20                  25                  30

Arg Leu Leu Glu Glu Asp Thr Pro Arg Tyr Met Arg Ala Thr Asp Pro
             35                  40                  45

Ala Ser Pro His Ile Gly Arg Ser Asn Glu Glu Glu Thr Ser Asp
         50                  55                  60

Ser Ser Leu Glu Lys Gln Thr Arg Ser Lys Gln Cys Thr Glu Thr Ser
 65                  70                  75                  80

Gly Ile His Ala Asp Ser Pro Tyr Ser Ser Gly Ile Met Asp Thr Gln
                 85                  90                  95

Ser Leu Glu Ser Lys Ala Glu Arg Ile Ala Arg Tyr Lys Ala Glu Arg
                100                 105                 110

Arg Arg Gln Leu Ala Glu Lys Tyr Gly Leu Thr Leu Asp Pro Glu Ala
            115                 120                 125

Asp Ser Glu Thr Pro Ser Arg Tyr Ser Arg Ser Arg Lys Asp Pro Glu
        130                 135                 140

Ala Ala Glu Lys Arg Gly Val Arg Ser Glu Arg Ser Ala Lys Ser Ser
145                 150                 155                 160

Arg Asp Ala Gly Ser Ser Tyr Ser Arg Thr Glu Leu Ser Gly Leu Arg
                165                 170                 175

Thr Cys Val Ala Glu Ser Lys Asp Tyr Gly Leu His Arg Ser Asp Gly
            180                 185                 190

Val Ser Asp Thr Glu Val Leu Leu Asn Ala Glu Asn Gln Arg Arg Gly
        195                 200                 205
```

-continued

```
Gln Glu Pro Ser Ala Thr Gly Leu Ala Arg Asp Leu Pro Leu Ala Gly
    210                 215                 220
Glu Val Ser Ser Phe Ser Phe Ser Gly Arg Asp Ser Ala Leu Gly
225                 230                 235                 240
Glu Val Pro Arg Ser Pro Lys Ala Val His Ser Leu Pro Ser Pro Ser
                    245                 250                 255
Pro Gly Gln Pro Ala Ser Pro Ser His Ser Thr Ser Asp Leu Pro Leu
                260                 265                 270
Pro Ala Glu Ala Arg Ala Arg Ser Thr Ser Asn Ser Glu Met Pro Ala
            275                 280                 285
Ala Glu Asp Glu Glu Lys Val Asp Glu Arg Ala Arg Leu Ser Val Ala
    290                 295                 300
Ala Lys Arg Leu Leu Phe Arg Glu Met Glu Lys Ser Phe Asp Glu Lys
305                 310                 315                 320
Ser Val Pro Lys Arg Arg Ser Arg Asn Ala Ala Val Glu Gln Arg Leu
                    325                 330                 335
Arg Arg Leu Gln Asp Arg Ser His Thr Gln Pro Val Thr Thr Glu Glu
                340                 345                 350
Val Val Ile Ala Ala Thr Leu Gln Ala Ser Ala His Gln Lys Ala Leu
            355                 360                 365
Ala Arg Asp Gln Thr Asn Glu Ser Lys Asp Ser Ala Glu Gln Gly Glu
    370                 375                 380
Pro Asp Ser Ser Thr Leu Ser Leu Ala Glu Lys Leu Ala Leu Phe Asn
385                 390                 395                 400
Lys Leu Ser Gln Pro Val Ser Lys Ala Ile Ser Thr Arg Asn Arg Leu
                    405                 410                 415
Asp Met Arg Gln Arg Arg Met Asn Ala Arg Tyr Gln Thr Gln Pro Val
                420                 425                 430
Thr Leu Gly Glu Val Glu Gln Val Gln Ser Gly Lys Leu Met Ala Phe
            435                 440                 445
Ser Pro Thr Ile Asn Thr Ser Val Ser Thr Ala Ser Thr Val Pro
    450                 455                 460
Pro Met Tyr Ala Gly Asn Leu Arg Thr Lys Pro Leu Pro Asp Asp Ser
465                 470                 475                 480
Phe Gly Ala Thr Glu Gln Lys Phe Ala Ser Ser Leu Glu Asn Ser Asp
                    485                 490                 495
Ser Pro Val Arg Ser Ile Leu Lys Ser Gln Gly Trp Gln Pro Ser Val
                500                 505                 510
Glu Gly Ala Gly Ser Lys Ala Met Leu Arg Glu Phe Glu Thr Glu
            515                 520                 525
Arg Lys Gly Gly Leu Thr Gly Gly Asp Gly Gly Val Thr Lys Tyr Gly
    530                 535                 540
Ser Phe Glu Glu Ala Glu Leu Ser Tyr Pro Val Leu Ser Arg Val Arg
545                 550                 555                 560
Glu Gly Asp Asn His Lys Glu Ala Ile Tyr Ala Leu Pro Arg Lys Gly
                    565                 570                 575
Ser Leu Glu Leu Ala His Pro Pro Ile Ala Gln Leu Gly Asp Asp Leu
                580                 585                 590
Lys Glu Phe Ser Thr Pro Lys Ser Thr Met Gln Ala Ser Pro Asp Trp
            595                 600                 605
Lys Glu Arg Gln Leu Phe Glu Glu Lys Val Asp Leu Glu Asn Val Thr
    610                 615                 620
Lys Arg Lys Phe Ser Leu Lys Ala Ala Glu Phe Gly Glu Pro Thr Ser
```

```
                625                 630                 635                 640

Glu Gln Thr Gly Ala Ala Gly Lys Pro Ala Ala Pro Thr Ala Thr
                    645                 650                 655

Pro Val Ser Trp Lys Pro Gln Asp Pro Ser Glu Gln Pro Gln Glu Lys
                660                 665                 670

Arg Tyr Gln Ser Pro Cys Ala Met Phe Ala Ala Gly Glu Ile Lys Ala
            675                 680                 685

Pro Ala Val Glu Gly Ser Leu Asp Ser Pro Ser Lys Thr Met Ser Ile
        690                 695                 700

Lys Glu Arg Leu Ala Leu Leu Lys Lys Ser Gly Glu Asp Trp Arg
705                 710                 715                 720

Asn Arg Leu Asn Arg Lys Gln Glu Tyr Gly Lys Ala Ser Ile Thr Ser
                725                 730                 735

Ser Leu His Ile Gln Glu Thr Glu Gln Ser Leu Lys Lys Lys Arg Val
            740                 745                 750

Thr Glu Ser Arg Glu Ser Gln Met Thr Ile Glu Glu Arg Lys His Leu
        755                 760                 765

Ile Thr Val Arg Glu Asp Ala Trp Lys Thr Arg Gly Lys Gly Ala Ala
    770                 775                 780

Asn Asp Ser Thr Gln Phe Thr Val Ala Gly Arg Met Val Lys Arg Gly
785                 790                 795                 800

Leu Ala Ser Pro Thr Ala Ile Thr Pro Val Ala Ser Pro Val Ser Ser
                805                 810                 815

Lys Ala Arg Gly Thr Thr Pro Val Ser Arg Pro Leu Glu Asp Ile Glu
            820                 825                 830

Ala Arg Pro Asp Met Gln Leu Glu Ser Asp Leu Lys Leu Asp Arg Leu
        835                 840                 845

Glu Thr Phe Leu Arg Arg Leu Asn Asn Lys Val Gly Gly Met Gln Glu
    850                 855                 860

Thr Val Leu Thr Val Thr Gly Lys Ser Val Lys Glu Val Met Lys Pro
865                 870                 875                 880

Asp Asp Asp Glu Thr Phe Ala Lys Phe Tyr Arg Ser Val Asp Ser Ser
                885                 890                 895

Leu Pro Arg Ser Pro Val Glu Leu Asp Glu Asp Phe Asp Val Ile Phe
            900                 905                 910

Asp Pro Tyr Ala Pro Arg Leu Thr Ser Ser Val Ala Glu His Lys Arg
        915                 920                 925

Ala Val Arg Pro Lys Arg Arg Val Gln Ala Ser Lys Asn Pro Leu Lys
    930                 935                 940

Met Leu Ala Ala Arg Glu Asp Leu Leu Gln Glu Tyr Thr Glu Gln Arg
945                 950                 955                 960

Leu Asn Val Ala Phe Val Glu Ser Lys Arg Met Lys Val Glu Lys Leu
                965                 970                 975

Ser Ala Asn Ser Ser Phe Ser Glu Val Thr Leu Ala Gly Leu Ala Ser
            980                 985                 990

Lys Glu Asn Phe Ser Asn Val Ser Leu Arg Ser Val Asn Leu Thr Glu
        995                 1000                1005

Gln Asn Ser Asn Asn Ser Ala Val Pro Tyr Lys Lys Leu Met Leu Leu
    1010                1015                1020

Gln Val Lys Gly Arg Arg His Val Gln Thr Arg Leu Val Glu Pro Arg
025                 1030                1035                1040

Ala Pro Ser Leu Asn Ser Gly Asp Cys Phe Leu Leu Leu Ser Pro His
            1045                1050                1055
```

```
His Cys Phe Leu Trp Val Gly Glu Phe Ala Asn Val Ile Glu Lys Ala
        1060                1065                1070

Lys Ala Ser Glu Leu Ala Ser Leu Ile Gln Thr Lys Arg Glu Leu Gly
    1075                1080                1085

Cys Arg Ala Thr Tyr Ile Gln Thr Val Glu Glu Gly Ile Asn Thr His
        1090                1095                1100

Thr His Ala Ala Lys Asp Phe Trp Lys Leu Leu Gly Gly Gln Ala Ser
105                 1110                1115                1120

Tyr Gln Ser Ala Gly Asp Pro Lys Glu Asp Glu Leu Tyr Glu Thr Ala
            1125                1130                1135

Ile Ile Glu Thr Asn Cys Ile Tyr Arg Leu Met Asp Asp Lys Leu Val
            1140                1145                1150

Pro Asp Asp Tyr Trp Gly Lys Ile Pro Lys Cys Ser Leu Leu Gln
        1155                1160                1165

Ser Lys Glu Val Leu Val Phe Asp Phe Gly Ser Glu Val Tyr Val Trp
    1170                1175                1180

His Gly Lys Glu Val Thr Leu Ala Gln Arg Lys Ile Ala Phe Gln Leu
185                 1190                1195                1200

Ala Lys His Leu Trp Asn Gly Thr Phe Asp Tyr Glu Asn Cys Asp Ile
        1205                1210                1215

Asn Pro Leu Asp Pro Gly Glu Cys Asn Pro Leu Ile Pro Arg Lys Gly
        1220                1225                1230

Gln Gly Arg Pro Asp Trp Ala Ile Phe Gly Arg Leu Thr Glu His Asn
        1235                1240                1245

Glu Thr Ile Leu Phe Lys Glu Lys Phe Leu Asp Trp Thr Glu Leu Lys
        1250                1255                1260

Arg Pro Asn Glu Lys Asn Ala Ser Glu Leu Ala Gln His Lys Asp Asp
265                 1270                1275                1280

Ala Arg Ala Glu Val Lys Pro Tyr Asp Val Thr Arg Met Val Pro Val
        1285                1290                1295

Pro Gln Thr Thr Ala Gly Thr Val Leu Asp Gly Val Asn Val Gly Arg
        1300                1305                1310

Gly Tyr Gly Leu Val Glu Gly Asp Asp Arg Arg Gln Phe Glu Ile Ala
        1315                1320                1325

Ser Ile Ser Val Asp Val Trp His Ile Leu Glu Phe Asp Tyr Ser Arg
    1330                1335                1340

Leu Pro Lys Gln Ser Ile Gly Gln Phe His Glu Gly Asp Ala Tyr Val
345                 1350                1355                1360

Val Lys Trp Lys Phe Ile Val Ser Thr Ala Val Gly Ser Arg Gln Lys
        1365                1370                1375

Gly Glu His Ser Val Arg Val Ala Gly Lys Glu Lys Cys Val Tyr Phe
        1380                1385                1390

Phe Trp Gln Gly Arg Gln Ser Thr Val Ser Glu Lys Gly Thr Ser Ala
    1395                1400                1405

Leu Met Thr Val Glu Leu Asp Glu Glu Arg Gly Ala Gln Val Gln Val
    1410                1415                1420

Leu Gln Gly Lys Glu Pro Pro Cys Phe Leu Gln Cys Phe Gln Gly Gly
425                 1430                1435                1440

Met Val Val His Ser Gly Arg Arg Glu Glu Glu Glu Asn Thr Gln
            1445                1450                1455

Ser Glu Trp Arg Leu Tyr Cys Val Arg Gly Glu Val Pro Val Glu Gly
        1460                1465                1470

Asn Leu Leu Glu Val Ala Cys His Cys Ser Ser Leu Arg Ser Arg Thr
        1475                1480                1485
```

```
Ser Met Val Val Leu Asn Val His Lys Ala Leu Ile Tyr Leu Trp His
    1490                1495                1500

Gly Cys Lys Ala Gln Ala His Thr Lys Glu Val Gly Arg Thr Ala Ala
     505               1510                1515                1520

Asn Lys Ile Lys Asp Gln Cys Pro Leu Glu Ala Gly Leu His Ser Ser
         1525                1530                1535

Ser Lys Val Thr Ile His Glu Cys Asp Glu Gly Ser Glu Pro Leu Gly
     1540                1545                1550

Phe Trp Asp Ala Leu Gly Arg Arg Asp Arg Lys Ala Tyr Asp Cys Met
         1555                1560                1565

Leu Gln Asp Pro Gly Asn Phe Asn Phe Thr Pro Arg Leu Phe Ile Leu
     1570                1575                1580

Ser Ser Ser Ser Gly Asp Phe Ser Ala Thr Glu Phe Met Tyr Pro Ala
     585                 1590                1595                1600

Arg Asp Pro Ser Val Val Asn Ser Met Pro Phe Leu Gln Glu Asp Leu
             1605                1610                1615

Tyr Ser Ala Pro Gln Pro Ala Leu Phe Leu Val Asp Asn His His Glu
         1620                1625                1630

Val Tyr Leu Trp Gln Gly Trp Trp Pro Ile Glu Asn Lys Ile Thr Gly
         1635                1640                1645

Ser Ala Arg Ile Arg Trp Ala Ser Asp Arg Lys Ser Ala Met Glu Thr
     1650                1655                1660

Val Leu Gln Tyr Cys Arg Gly Lys Asn Leu Lys Lys Pro Pro Pro Lys
 665             1670                1675                1680

Ser Tyr Leu Ile His Ala Gly Leu Glu Pro Leu Thr Phe Thr Asn Met
         1685                1690                1695

Phe Pro Ser Trp Glu His Arg Glu Asp Ile Ala Glu Ile Thr Glu Met
         1700                1705                1710

Asp Thr Glu Val Ser Asn Gln Ile Thr Leu Val Glu Asp Val Leu Ala
         1715                1720                1725

Lys Leu Cys Lys Thr Ile Tyr Pro Leu Ala Asp Leu Leu Ala Arg Pro
     1730                1735                1740

Leu Pro Glu Gly Val Asp Pro Leu Lys Leu Glu Ile Tyr Leu Thr Asp
 745             1750                1755                1760

Glu Asp Phe Glu Phe Ala Leu Asp Met Thr Arg Asp Glu Tyr Asn Ala
         1765                1770                1775

Leu Pro Ala Trp Lys Gln Val Asn Leu Lys Lys Ala Lys Gly Leu Phe
         1780                1785                1790
```

(2) INFORMATION FOR SEQ ID NO:5:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:5:

```
Ser Pro Val Glu Leu Asp Glu Asp Phe Asp Val Ile Phe Asp Pro Tyr
 1               5                   10                  15

Ala Pro Arg
```

(2) INFORMATION FOR SEQ ID NO:6:

(i) SEQUENCE CHARACTERISTICS:
        (A) LENGTH: 20 amino acids (B) TYPE: amino acid
        (D) TOPOLOGY: linear (ii) MOLECULE TYPE: peptide (xi) SEQUENCE DESCRIPTION: SEQ ID NO:6:

Met Val Pro Arg Pro Gln Thr Thr Ala Gly Asp Val Leu Asp Gly Val
 1               5                  10                  15

Asn Val Gly Arg
        20

(2) INFORMATION FOR SEQ ID NO:7:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:7:

Tyr Gly Ser Phe Glu Glu Ala Glu Leu Ser Tyr Pro Val Leu Ser Arg
 1               5                  10                  15

(2) INFORMATION FOR SEQ ID NO:8:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:8:

Lys Met Leu Ala Ala Arg Glu Asp Leu Leu Gln Glu Tyr Thr
 1               5                  10

(2) INFORMATION FOR SEQ ID NO:9:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:9:

Val Arg Glu Gly Asp Asn His Lys Glu Ala Ile Tyr Ala
 1               5                  10

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:10:

Tyr Gln Thr Gln Pro Val Thr
 1               5

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:11:

Leu Phe Arg Glu Met Glu Lys
  1               5

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Other
            (B) LOCATION: 3...3
            (D) OTHER INFORMATION: where N at position 3 is inosine
            (A) NAME/KEY: Other
            (B) LOCATION: 6...6
            (D) OTHER INFORMATION: where N at position 6 is inosine
            (A) NAME/KEY: Other
            (B) LOCATION: 12...12
            (D) OTHER INFORMATION: where N at position 12 is inosine (xi) SEQUENCE DESCRIPTION: SEQ ID NO:12:

CCNGTNGARY TNGAYGARGA                                              20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Other
            (B) LOCATION: 3...3
            (D) OTHER INFORMATION: where N at position 3 is inosine
            (A) NAME/KEY: Other
            (B) LOCATION: 6...6
            (D) OTHER INFORMATION: where N at position 6 is inosine
            (A) NAME/KEY: Other
            (B) LOCATION: 12...12
            (D) OTHER INFORMATION: where N at position 12 is inosine (xi) SEQUENCE DESCRIPTION: SEQ ID NO:13:

CKNGGNGCRT ANGGRTCRAA                                              20

(2) INFORMATION FOR SEQ ID NO:14:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

AGTTNGATGA GGATTTCGAT GTCATTTTYG AYCC                              34

(2) INFORMATION FOR SEQ ID NO:15:

(i) SEQUENCE CHARACTERISTICS:
            (A) LENGTH: 22 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

CTCGCGGCCA GCATCTTCAG GG                                                  22

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

GATCTTCCCT CGCGGCCAGC ATCTTCAGGG                                           30

(2) INFORMATION FOR SEQ ID NO:17:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

TCAAACGACT TCTCCATCTC CCTGAAGAGC                                           30

(2) INFORMATION FOR SEQ ID NO:18:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

GTCAGGTTCT CCCTGCTCAG CAGAATCTTT                                           30

(2) INFORMATION FOR SEQ ID NO:19:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

GAGCCAGGTC AACTTCAAAT TCAGAAATG                                            29

(2) INFORMATION FOR SEQ ID NO:20:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:20:

TATTAAGGTA GAAAGGTGGA TTCGCACAGA                                                30

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GATGAGGATT TCGATGTCAT TTTYGATCTT                                                30

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GGCTCCAGAC CAGCGTGGAT AAGGTAAGA                                                 29

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

TAGAAAAGCA AACTCGATCC AAATACTGCA                                                30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GGAGGTTTCT GTGCAGTATT TGGATCGAGT                                                30

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GACCTGTCCT GCAGACGGCG TAAGCCTC                                                  28

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TGGGCTGCGT GTCGGTTTCA ATTCC                                      25

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

TGTGGCACGC ATGTATCTGG GTGTG                                      25

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CTCCAGCAGC AAACATCGCA CACGG                                      25

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

CACCCAGGTT CCTCCAGCAT CTCCT                                      25

(2) INFORMATION FOR SEQ ID NO:30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

CCATCCTAAT ACGACTCACT ATAGGGC                                    27

(2) INFORMATION FOR SEQ ID NO:31:

(i) SEQUENCE CHARACTERISTICS:
        (A) LENGTH: 25 base pairs

```
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:31:

GGCACACGCT ACAAACGACG ACCTC                                            25
```

ACTIN-BINDING POLYPEPTIDES AND NUCLEIC ACIDS ENCODING THE SAME

STATEMENT AS TO FEDERALLY SPONSORED RESEARCH

This invention was made with Government support under grants CA54885 and GM33048 awarded by the National Institutes of Health. The Government may have certain rights in the invention.

BACKGROUND OF THE INVENTION

This invention relates to actin-binding polypeptides called "supervillin" polypeptides, and nucleic acids encoding supervillin polypeptides.

Interactions between the plasma membrane and the actin cytoskeleton are mediated by actin-binding proteins associated with the plasma membrane. These actin-binding proteins are involved in a variety of processes, e.g., controlling cell shape, mediating cell-substrate and cell-cell interactions, organizing membrane proteins into domains, and in regulating membrane domain function. For example, some protein domains contain membrane-spanning proteins, such as ion channels and adhesion molecules, that are localized due to interactions with cortical meshworks of actin filaments cross-linked by spectrin. As another example, intercellular adhesion at adherens junctions, which is mediated by $Ca^{2+}$-sensitive transmembrane proteins called cadherins, depends upon cadherin attachment to actin filaments through linker proteins, such as α-catenin and β-catenin.

SUMMARY OF THE INVENTION

The invention is based on the discovery of nucleic acids encoding supervillin, a novel actin-binding protein associated with the plasma membrane. Supervillin polypeptides based on the wild type supervillin protein include a 1788 amino acid polypeptide isolated from HeLa cells (SEQ ID NO:2) and a 1792 amino acid polypeptide (SEQ ID NO:4) isolated from Madin-Darby bovine kidney (MDBK) cells.

In general, the invention features isolated nucleic acid molecules encoding supervillin polypeptides. For example, the isolated nucleic acid molecule may encode human supervillin (SEQ ID NO:2) or bovine supervillin (SEQ ID NO:4). The isolated nucleic acid may also encode polypeptide having a sequence that is at least 85%, 90%, 95%, 98%, or 99% identical to the sequence of human supervillin (SEQ ID NO:2) or bovine supervillin (SEQ ID NO:4). Examples of supervillin-encoding nucleic acid sequences are those specified by SEQ ID NO:1 and SEQ ID NO:3. The encoded supervillin polypeptide may bind F-actin, associate with plasma membranes, or both.

The term "nucleic acid" encompasses both RNA and DNA, including cDNA, genomic DNA, and synthetic (e.g., chemically synthesized) DNA. The nucleic acid may be double-stranded or single-stranded. Where single-stranded, the nucleic acid may be the sense strand or the antisense strand.

By "isolated nucleic acid" is meant nucleic acid that is not immediately contiguous with both of the coding sequences with which it is immediately contiguous (one on the 5' end and one on the 3' end) in the naturally occurring genome of the organism from which it is derived. Thus, a recombinant nucleic acid could include some or all of the 5' non-coding (e.g., promoter) sequences which are immediately contiguous to the coding sequence. The term therefore includes, for example, a recombinant DNA which is incorporated into a vector; into an autonomously replicating plasmid or virus, such as a retrovirus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

In other embodiments, the isolated nucleic acid molecule encoding supervillin hybridizes to a nucleic acid molecule having the sequence of nucleotides 451–5814 of SEQ ID NO:1, inclusive, or nucleotides 201 through 5576 of SEQ ID NO:3, inclusive, or their complement. In other embodiments, the hybridization occurs under stringent conditions.

"Stringent conditions" means hybridization at 50° C. in Church buffer (7% SDS, 0.5% $NaHPO_4$, 1 mM EDTA, 1% BSA) and washing at 50° C. in 2× SSC. The hybridizing portion of the hybridizing nucleic acids are preferably 20, 30, 50, or 70 bases long. Preferably, the hybridizing portion of the hybridizing nucleic acid is 95% or even 98% or 100% identical to a sequence complementary to a portion of a nucleic acid encoding a supervillin polypeptide. Hybridizing nucleic acids of the type described above can be used as cloning probes, primers (e.g., a PCR primer), or diagnostic probes. Preferred hybridizing nucleic acids encode a polypeptide having some or all of the biological activities possessed by naturally-occurring supervillin protein. The biological activity can be measured using one of the assays described herein. Hybridizing nucleic acids can be splice variants encoded by one of the supervillin genes described herein. Thus, they may encode a protein which is shorter or longer than the various supervillin polypeptides described herein. Hybridizing nucleic acids may also encode proteins which are related to supervillin (e.g., proteins encoded by genes which include a portion having a relatively high degree of identity to a supervillin gene described herein).

The invention also features a host cell which includes an isolated nucleic acid molecule encoding supervillin, as well as a nucleic acid vector containing a nucleic acid molecule encoding a supervillin peptide (e.g., an expression vector; a vector which includes a regulatory element; a vector which includes a regulatory element selected from the group consisting of the cytomegalovirus hCMV immediate early gene, the early promoter of SV40 adenovirus, the late promoter of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors; a vector which includes a regulatory element which directs tissue-specific expression; a vector which includes a reporter gene; a vector which includes a reporter gene selected from the group selected from the group consisting of β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT); a vector that is a plasmid; a vector that is a virus; and a vector that is a retrovirus).

The invention also features substantially pure supervillin polypeptides. Among the polypeptides encompassed within the invention are those corresponding to the region containing nuclear localization sequences and regions containing villin-like domains.

By "polypeptide" is meant any chain of amino acids, regardless of length or post-translational modification (e.g., glycosylation or phosphorylation), and thus includes polypeptides, proteins, and peptides.

By "substantially pure" is meant a preparation which is at least 60% by weight (dry weight) the compound of interest, i.e., a supervillin polypeptide, and which does not include any non-supervillin polypeptides that have essentially the same molecular weight as supervillin, e.g., polypeptides that may migrate at a similar position in an SDS-acrylamide gel. Preferably the preparation is at least 75%, more preferably at least 90%, and most preferably at least 99%, by weight of the supervillin polypeptide. Purity can be measured by any appropriate standard method, e.g., column chromatography, polyacrylamide gel electrophoresis, or HPLC analysis.

The polypeptides of the invention include, but are not limited to full-length supervillin proteins or polypeptides, peptide fragments, recombinant polypeptides, natural polypeptides, and synthetic polypeptides, as well as polypeptides which are preproteins or proproteins. The supervillin polypeptides include, e.g., a supervillin polypeptide that is soluble under physiological conditions, a supervillin polypeptide that binds F-actin, associates with plasma membranes, or both.

The supervillin polypeptide includes an amino acid sequence that is at least 85%, 90%, 95%, 98%, 99%, or 100% identical to the amino acid sequence of SEQ ID NO:2 or SEQ ID NO:4.

The polypeptides of the invention can be expressed fused to another polypeptide, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

By "mature human supervillin" is meant a polypeptide having the sequence shown in FIG. 4 (SEQ ID NO:2) from about amino acid 1 to about amino acid 1788.

By "substantially identical" is meant a polypeptide or nucleic acid having a sequence that is at least 85%, preferably 90%, more preferably 95%, and most preferably 99% or more identical to the sequence of the reference amino acid or nucleic acid sequence. For polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

Sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, other polypeptides will meet the same criteria.

Polypeptides corresponding to one or more domains of supervillin, e.g., the amino terminal regions having putative nuclear localization sequences, or the carboxy terminal regions having villin-like domains, are also within the scope of the invention. Preferred polypeptides are those which are soluble under normal physiological conditions. Also within the invention are soluble fusion proteins in which a full-length form of supervillin or a portion (e.g., one or more domains) thereof is fused to an unrelated protein or polypeptide (i.e., a fusion partner) to create a fusion protein. The supervillin polypeptide may be recombinantly produced, e.g., from expression of an isolated supervillin nucleic acid.

In other embodiments, the invention features a substantially pure polypeptide which includes a first portion linked to a second portion, the first portion including a supervillin polypeptide and the second portion including a detectable marker. By "linked" is meant a first portion connected to a second portion by covalent or noncovalent bonds.

The invention further features an antibody (e.g., a monoclonal antibody or polyclonal antibody) that specifically binds to a supervillin polypeptide. The antibody can be raised against full-length supervillin polypeptides, or peptide fragments such as those of SEQ ID NO:5–11.

The invention also features a pharmaceutical composition which includes a supervillin polypeptide.

Also included in the invention is a method for detecting a supervillin polypeptide in a sample by obtaining a biological sample, contacting the biological sample with an antibody that specifically binds supervillin under conditions that allow the formation of supervillin-antibody complexes, and detecting the complexes (if any) as an indication of the presence or activity of supervillin in the sample.

By "specifically binds" is meant an antibody that recognizes and binds to a particular antigen, e.g., a supervillin polypeptide of the invention, but which does not substantially recognize or bind to other molecules in a sample, e.g., a biological sample, which includes supervillin.

The invention features a method of identifying a compound that modulates the expression or activity of supervillin by comparing the expression or level of activity of supervillin in a cell in the presence and absence of a selected compound, wherein a difference in the level of activity in the presence and absence of the selected compound indicates that the selected compound modulates the activity of supervillin.

In addition, the invention features a method of treating a patient suffering from a disorder associated with aberrant expression or function of supervillin (e.g., excessive expression or activity of supervillin, or insufficient expression or activity of supervillin) by administering to the patient a compound which modulates the activity or expression at supervillin (e.g., inhibits expression or activity of supervillin in a patient having excessive expression or activity of supervillin, or increases the expression or activity in a patient having insufficient supervillin expression or activity). Disorders associated with aberrant expression of supervillin can include, e.g., hyperproliferative diseases such as carcinomas.

The invention also includes a method of diagnosing a disorder associated with aberrant (e.g., increased) expression or activity of supervillin by obtaining a biological sample from a patient and measuring supervillin expression in the biological sample. Increased or decreased supervillin expression or activity in the biological sample compared to a control indicates that the patient suffers from a disorder associated with aberrant expression or activity of supervillin, such as carcinoma, which is indicated by increased activity or expression.

The invention also includes a method of inducing apoptosis in a cell by administering a compound which interferes with expression or function of a supervillin gene to the cell. The compounds can include supervillin antisense oligonucleotides, e.g., those corresponding to SEQ ID NOS:26–29.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is a schematic representation of the predicted amino acid sequence of bovine supervillin (SEQ ID NO:4).

FIGS. 4A and 4B are a schematic representation of the nucleotide sequence of human supervillin cDNA (SEQ ID NO:1) (A) and its predicted amino acid sequence (SEQ ID NO:2) (B).

FIG. 5 is a comparison of the predicted bovine supervillin amino acid sequence (SEQ ID NO:4) (top) and the human supervillin amino acid sequence (SEQ ID NO:2) (bottom).

FIGS. 9A–C are a schematic representation of the nucleotide sequence of bovine supervillin cDNA (SEQ ID NO:3). The start codon begins at nucleotide 201.

DETAILED DESCRIPTION

Figure 2:
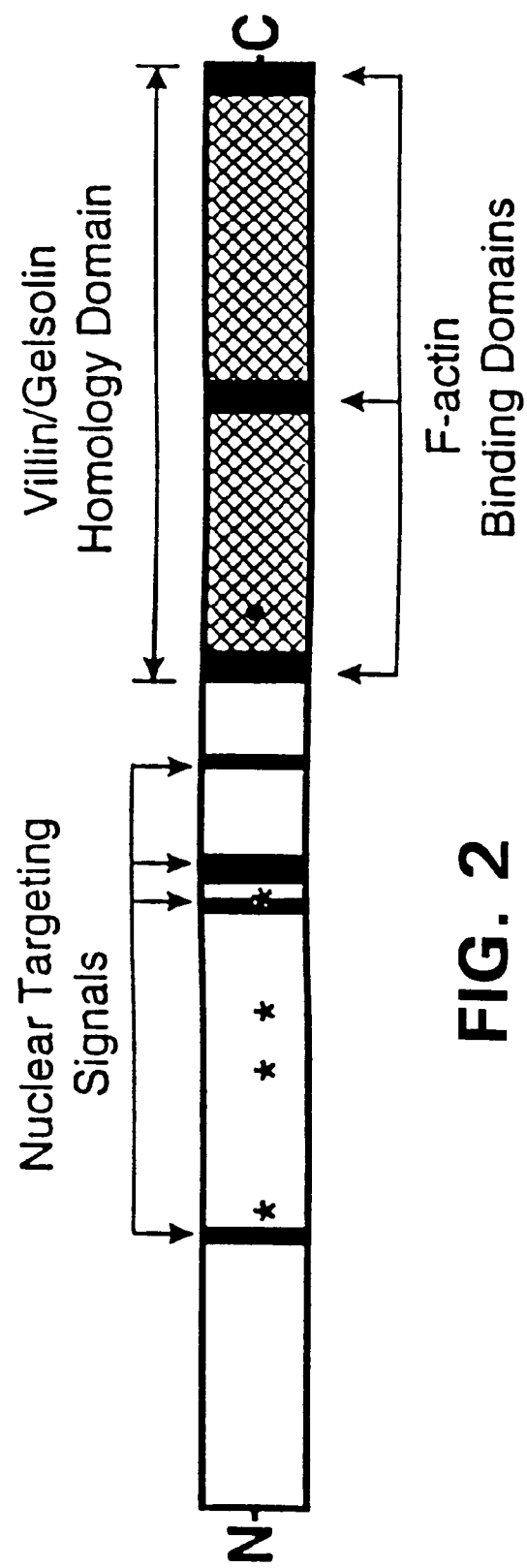
FIG. 2 is a schematic of domain structures within the bovine supervillin protein.

The present invention provides supervillin polypeptides and nucleic acids encoding supervillin polypeptides. Naturally occurring supervillin protein was originally identified as an apparent 205 kDA protein in $^{125}$I F-actin blot overlays of bovine neutrophil membranes (Pestonjamasp et al., *Mol. Biol. Cell,* 6:247, 1995).

The supervillin carboxy terminus is very similar to the villin/gelsolin family of actin-binding proteins. The amino terminus of supervillin is novel and contains several potential nuclear localization signals. Supervillin is a cytosolic and nuclear protein and co-localizes with E-cadherin at sites of adhesion between MDBK cells. The primary sequence motifs and cellular localization(s) of supervillin suggest that this protein is a structural component of the plasma membrane skeleton that may also be involved in the regulation of cell-cell adhesion and/or information transfer to other cell compartments.

Supervillin messenger RNA is present in all cell types examined and is especially prominent in muscle tissue and in carcinoma cells. The RNA detected in muscle tissue is of a slightly greater size than that detected in non-muscle cell types.

Disruption of supervillin expression in subconfluent epithelial cells is associated with the induction of apoptosis in these cells. Supervillin may be involved in promoting cell survival and in mediating cell-cell and/or cell-substrate interactions.

Supervillin Nucleic Acid Molecules

The new supervillin nucleic acid molecules can be cDNA, genomic DNA, synthetic DNA, or RNA, and can be double-stranded or single-stranded (i.e., either a sense or an antisense strand). Fragments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions.

The nucleic acid molecules of the invention can contain naturally occurring sequences, or sequences that differ from those that occur naturally, but, due to the degeneracy of the genetic code, encode the same polypeptide (for example, the polypeptide of SEQ ID NO:2 or SEQ ID NO:4). In addition, these nucleic acid molecules are not limited to sequences that encode only polypeptides, and thus, can include some or all of the non-coding sequences that lie upstream or downstream from a coding sequence.

The new nucleic acid molecules can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

In addition, the isolated nucleic acid molecules encompass fragments that are not found as such in the natural state. Thus, the invention encompasses recombinant molecules, such as those in which a nucleic acid molecule (for example, an isolated nucleic acid molecule encoding supervillin) is incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

In the event the new nucleic acid molecules encode or act as antisense molecules, they can be used, for example, to regulate translation of supervillin mRNA.

The invention also encompasses nucleic acid molecules that hybridize under stringent conditions to a nucleic acid molecule encoding a supervillin polypeptide. The cDNA sequences described herein (e.g., the supervillin sequences shown in FIG. 4 (SEQ ID NO:1) and FIGS. 9A–C (SEQ ID NO:3)) can be used to identify these nucleic acids, which include, for example, nucleic acids that encode homologous polypeptides in other species, and splice variants of the supervillin gene in humans or other mammals. Accordingly, the invention features methods of detecting and isolating these nucleic acid molecules. Using these methods, a sample (for example, a nucleic acid library, such as a cDNA or genomic library) is contacted (or "screened") with a supervillin-specific probe (for example, a fragment of SEQ ID NO:1 or SEQ ID NO:3 that is at least 25 or 50 nucleotides long). The probe will hybridize under stringent conditions to nucleic acids encoding related polypeptides (or to complementary sequences thereof).

The probe, which can contain at least 25 (for example, 25, 50, 100, or 200 nucleotides) can be produced using any of several standard methods (see, for example, Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a supervillin-specific nucleic acid sequence (for example, a nucleic acid encoding the chemokine-like domain) that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high stringency conditions to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2× SSC is 10-fold more concentrated than 0.2× SSC). Nucleic acids are hybridized at 42° C. in 2× SSC/0.1% SDS (sodium dodecylsulfate; a detergent) and then washed in 0.2× SSC/0.1% SDS at room temperature (for conditions of low stringency); 0.2× SSC/0.1% SDS at 42° C. (for conditions of moderate stringency); and 0.1× SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% NaHPO$_4$, 1 M EDTA, 1% BSA) and washing is carried out at 50° C. in 2× SSC.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing supervillin-related coding sequences and/or their complements (that is, "antisense" sequence); (b) expression vectors that contain any of the foregoing supervillin-related coding sequences operatively associated with a regulatory element (examples of which are given below) that directs the expression of the coding sequences; (c) expression vectors containing, in addition to sequences encoding a supervillin polypeptide, nucleic acid sequences that are unrelated to nucleic acid sequences encoding supervillin, such as molecules encoding a reporter or marker; and (d) genetically engineered host cells that contain any of the foregoing expression vectors and thereby express the nucleic acid molecules of the invention in the host cell.

Recombinant nucleic acid molecules can contain a sequence encoding a soluble supervillin polypeptide, mature supervillin, or supervillin including a signal sequence. The full length supervillin polypeptide, a domain of supervillin, or a fragment thereof may be fused to additional polypeptides, as described below. Similarly, the nucleic acid molecules of the invention can encode the mature form of supervillin or a form that encodes a polypeptide which facilitates secretion. In the latter instance, the polypeptide is typically referred to as a proprotein, which can be converted into an active form by removal of the signal sequence, for example, within the host cell. Proproteins can be converted into the active form of the protein by removal of the inactivating sequence.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a supervillin polypeptide and the second portion being, for example, the reporter described above or an immunoglobulin constant region.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequence encoding supervillin ((SEQ ID NO:1) or SEQ ID NO:3)); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing supervillin nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing supervillin polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.*, 2:1791, 1983), in which the coding sequence of the insert may be ligated individually into the vector in frame with the lacZ coding region so that a fusion protein is produced; pIN vectors (Inouye and Inouye, *Nucleic Acids Res.*, 13:3101–3109, 1985; Van Heeke and Schuster, *J. Biol. Chem.*, 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.*, 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region El or E3) will result in a recombinant virus that is viable and capable of expressing a supervillin gene product in infected hosts (for example, see Logan and Shenk, *Proc. Natl. Acad. Sci. USA*, 81:3655–3659, 1984). Specific initiation signals may also be required for efficient translation of inserted nucleic acid molecules. These signals include the ATG initiation codon and adjacent sequences.

In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.*, 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the supervillin sequences described above may be engineered. Rather than using expression vectors which contain viral origins of replication, host cells can be transformed with DNA controlled by appropriate expression control elements (for example, promoter, enhancer sequences, transcription terminators, and polyadenylation sites), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express supervillin. Such engineered cell lines may be particularly useful in screening and evaluation of compounds that affect the endogenous activity of the gene product.

A number of selection systems can be used. For example, the herpes simplex virus thymidine kinase (Wigler, et al., Cell, 11:223, 1977), hypoxanthine-guanine phosphoribosyltransferase (Szybalska and Szybalski, Proc. Natl. Acad. Sci. USA, 48:2026, 1962), and adenine phosphoribosyltransferase (Lowy, et al., Cell, 22:817, 1980) genes can be employed in tk$^-$, hgprt$^-$ or aprt$^-$ cells, respectively. Also, anti-metabolite resistance can be used as the basis of selection for the following genes: dhfr, which confers resistance to methotrexate (Wigler et al., Proc. Natl. Acad. Sci. USA, 77:3567, 1980; O'Hare et al., Proc. Natl. Acad. Sci. USA, 78:1527, 1981); gpt, which confers resistance to mycophenolic acid (Mulligan and Berg, Proc. Natl. Acad. Sci. USA, 78:2072, 1981); neo, which confers resistance to the aminoglycoside G-418 (Colberre-Garapin et al., J. Mol. Biol., 150:1, 1981); and hygro, which confers resistance to hygromycin (Santerre et al., Gene, 30:147, 1984).

Alternatively, any fusion protein may be readily purified by utilizing an antibody specific for the fusion protein being expressed. For example, a system described by Janknecht et al. allows for the ready purification of non-denatured fusion proteins expressed in human cell lines (Proc. Natl. Acad. Sci. USA, 88:8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$-nitriloacetic acid-agarose columns and histidine-tagged proteins are selectively eluted with imidazole-containing buffers.

Supervillin nucleic acid molecules are useful for diagnosis of disorders associated with aberrant expression of supervillin. Supervillin nucleic acid molecules are useful in genetic mapping and chromosome identification.

Supervillin Polypeptides

The supervillin polypeptides described herein are those encoded by any of the nucleic acid molecules described herein and include supervillin fragments, mutants, truncated forms, and fusion proteins. These polypeptides can be prepared for a variety of uses, including, but not limited to, the generation of antibodies, as reagents in diagnostic assays, for the identification of other cellular gene products or compounds that can modulate the activity or expression of supervillin, and as pharmaceutical reagents useful for the treatment of disorders associated with aberrant expression or activity of naturally occurring supervillin protein.

Preferred polypeptides are substantially pure supervillin polypeptides, including those that correspond to the polypeptide with an intact signal sequence, the secreted form of the polypeptide of the human supervillin polypeptide. Especially preferred are polypeptides that are soluble under normal physiological conditions.

The invention also encompasses polypeptides that are functionally equivalent to supervillin. These polypeptides are equivalent to supervillin in that they are capable of carrying out one or more of the functions of supervillin protein in a biological system. Such biological functions can include binding to plasma membranes (as assayed using the methods described in Example 4), binding to F-actin (as assayed using the methods described in Example 5), or both.

Preferred supervillin polypeptides have 20%, 40%, 50%, 75%, 80%, or even 90% of one or more of the biological activities of the full-length, mature wild type human form of supervillin. Such comparisons are generally based on an assay of biological activity in which equal concentrations of the polypeptides are used and compared. The comparison can also be based on the amount of the polypeptide required to reach 50% of the maximal stimulation obtainable.

Functionally equivalent polypeptides can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the summary of the invention.

Polypeptides that are functionally equivalent to supervillin polypeptides ((SEQ ID NO:2) or (SEQ ID NO:4)) can be made using random mutagenesis techniques well known to those skilled in the art (and the resulting mutant supervillin polypeptides can be tested for activity). It is more likely, however, that such polypeptides will be generated by site-directed mutagenesis (again using techniques well known to those skilled in the art). These polypeptides may have increased functionality or decreased functionality.

To design functionally equivalent polypeptides, it is useful to distinguish between conserved positions and variable positions. This can be done by aligning the sequence of supervillin cDNAs that were obtained from various organisms (e.g., as in FIG. 5) It is preferable that conserved residues are not altered.

Mutations within the supervillin coding sequence can be made to generate variant supervillin genes that are better suited for expression in a selected host cell.

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

The polypeptides of the invention can be chemically synthesized (for example, see Creighton, "Proteins: Structures and Molecular Principles," W. H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The invention also features polypeptides that interact with supervillin (and the genes that encode them) and thereby alter the function of supervillin. Interacting polypeptides can be identified using methods known to those skilled in the art. One suitable method is the "two-hybrid system," which detects protein interactions in vivo (Chien et al., *Proc. Natl. Acad. Sci. USA,* 88:9578, 1991), as described in further detail below. A kit for practicing this method is available from Clontech (Palo Alto, Calif.).

Transgenic Animals

Supervillin polypeptides can also be expressed in transgenic animals. These animals represent a model system for the study of disorders that are caused by or exacerbated by overexpression or underexpression of supervillin, and for the development of therapeutic agents that modulate the expression or activity of supervillin.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred for research.

Several techniques known in the art can be used to introduce a supervillin transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA,* 82:6148, 1985); gene targeting into embryonic stem cells (Thompson et al., *Cell,* 56:313, 1989); and electroporation of embryos (Lo, *Mol. Cell. Biol.,* 3:1803, 1983).

The present invention provides for transgenic animals that carry a supervillin transgene in all their cells, as well as animals that carry a transgene in some, but not all of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA,* 89:6232, 1992). The regulatory sequences required for such a cell-type specific activation will depend upon the particular cell type of interest, and will be apparent to those of skill in the art.

When it is desired that the supervillin transgene be integrated into the chromosomal site of the endogenous supervillin the endogenous, gene targeting is preferred. Briefly, when such a technique is to be used, vectors containing some nucleotide sequences homologous to an endogenous supervillin gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous supervillin gene in only that cell type (Gu et al., *Science,* 265:103, 1984). The regulatory sequences required for such a cell-type specific inactivation will depend upon the particular cell type of interest, and will be apparent to those of skill in the art. These techniques are useful for preparing "knock out" animals having no functional supervillin gene.

Once transgenic animals have been generated, the expression of the recombinant supervillin gene can be assayed utilizing standard techniques. Initial screening may be accomplished by Southern blot analysis or PCR techniques to determine whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-PCR. Samples of supervillin gene-expressing tissue can also be evaluated immunocytochemically using antibodies specific for the supervillin transgene product.

For a review of techniques that can be used to generate and assess transgenic animals, skilled artisans can consult Gordon (*Intl. Rev. Cytol.,* 115:171–229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology,* 9:86, 1991; Palmiter et al., *Cell,* 41:343, 1985; Kraemer et al., "Genetic Manipulation of the Early Mammalian Embryo," Cold Spring Harbor Press, Cold Spring Harbor, N.Y., 1985; Hammer et al., *Nature,* 315:680, 1985; Purcel et al., *Science,* 244:1281, 1986; Wagner et al., U.S. Pat. No. 5,175,385; and Krimpenfort et al., U.S. Pat. No. 5,175,384.

Anti-Supervillin Antibodies

Supervillin polypeptides (or immunogenic fragments or analogs) can be used to raise antibodies; such polypeptides can be produced by recombinant techniques or synthesized as described above (see, for example, "Solid Phase Peptide Synthesis," supra; Ausubel et al., supra). In general, the peptides can be coupled to a carrier protein, such as keyhole limpet hemocyanin (KLH), as described in Ausubel et al., supra, mixed with an adjuvant, and injected into a host mammal. Antibodies can be purified by peptide antigen affinity chromatography.

In particular, various host animals can be immunized by injection with a supervillin protein or polypeptide. Host animals include rabbits, chickens, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Potentially useful human adjuvants include BCG (bacille Calmette-Guerin) and *Corynebacterium parvum.* Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the supervillin polypeptides described above and standard hybridoma technology (see, for example, Kohler et al., *Nature,* 256:495, 1975; Kohler et al., *Eur. J. Immunol.,* 6:511, 1976; Kohler et al., *Eur. J. Immunol.,* 6:292, 1976;

Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., Nature, 256:495, 1975, and U.S. Pat. No. 4,376,110; the human B-cell hybridoma technique (Kosbor et al., Immunology Today, 4:72, 1983; Cole et al., Proc. Natl. Acad. Sci. USA, 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific supervillin recognition by Western blot or immunoprecipitation analysis by standard methods, e.g., as described in Ausubel et al., supra. Antibodies that specifically recognize and bind to supervillin polypeptides are useful in the invention. For example, such antibodies can be used in an immunoassay to monitor the level of supervillin produced by a mammal (for example, to determine the amount or subcellular location of supervillin).

Preferably, antibodies of the invention are produced using fragments of the supervillin protein which lie outside highly conserved regions and appear likely to be antigenic, by criteria such as high frequency of charged residues. In one specific example, such fragments are generated by standard techniques of PCR, and are then cloned into the PGEX expression vector (Ausubel et al., supra). Fusion proteins are expressed in E. coli and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera are also checked for their ability to immunoprecipitate recombinant supervillin proteins or control proteins, such as glucocorticoid receptor, CAT, or luciferase.

The antibodies can be used, for example, in the detection of the supervillin in a biological sample as part of a diagnostic assay. Antibodies also can be used in a screening assay to measure the effect of a candidate compound on expression or localization of supervillin. Additionally, such antibodies can be used in conjunction with the gene therapy techniques need to, for example, evaluate the normal and/or engineered supervillin-expressing cells prior to their introduction into a patient. Such antibodies additionally can be used therapeutically in a method for inhibiting abnormal supervillin activity.

In addition, techniques developed for the production of "chimeric antibodies" (Morrison et al., Proc. Natl. Acad. Sci. USA, 81:6851, 1984; Neuberger et al., Nature, 312:604, 1984; Takeda et al., Nature, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against a supervillin protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science, 246:1275, 1989) to allow rapid and easy identification of monoclonal Fab fragments with the desired specificity.

Antibodies to supervillin can, in turn, be used to generate anti-idiotype antibodies that resemble a portion of supervillin using techniques well known to those skilled in the art (see, e.g., Greenspan et al., FASEB J., 7:437, 1993; Nissinoff, J. Immunol., 147:2429, 1991). For example, antibodies that bind to supervillin and competitively inhibit the binding of a binding partner of supervillin can be used to generate anti-idiotype antibodies that resemble a binding partner binding domain of supervillin and, therefore, bind to and neutralize a binding partner of supervillin. Such neutralizing anti-idiotype antibodies or Fab fragments of such anti-idiotype antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics, 7:13–21, 1994; see also U.S. Pat. Nos. 5,545,806 and 5,569,825, both of which are hereby incorporated by reference).

The methods described herein in which anti-supervillin antibodies are employed may be performed, for example, by utilizing pre-packaged diagnostic kits comprising at least one specific supervillin nucleotide sequence or antibody reagent described herein, which may be conveniently used, for example, in clinical settings, to diagnose patients exhibiting symptoms of the disorders described below.

Antisense Nucleic Acids

Treatment regimes based on an "antisense" approach involve the design of oligonucleotides (either DNA or RNA) that are complementary to supervillin mRNA. These oligonucleotides bind to the complementary supervillin mRNA transcripts and prevent translation. Absolute complementarity, although preferred, is not required. A sequence "complementary" to a portion of an RNA, as referred to herein, means a sequence having sufficient complementarily to be able to hybridize with the RNA, forming a stable duplex under normal in vivo conditions; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides complementary to the supervillin coding sequences (e.g., the oligonucleotides described in Example 8) can be used. Alternatively, sequences complementary to the 5' or 3' noncoding regions can also be used to inhibit supervillin expression. Whether designed to hybridize to the 5', 3', or coding region of supervillin mRNA, antisense nucleic acids should be at least six nucleotides in length, and can be oligonucleotides ranging from 6 to about 50 nucleotides in length. In specific aspects the oligonucleotide is at least 10 nucleotides, at least 17 nucleotides, at least 25 nucleotides, or at least 50 nucleotides in length. The oligonucleotides can comprise the sequences 5'-TGGGCTGCGTGTCGGTTTCAATTCC-3' (SEQ ID NO:26), 5'-TGTGGCACGCATGTATCTGGGTGTG-3' (SEQ ID NO:27), 5'-CTCCAGCAGCAAACATCGCACACGG-3' (SEQ ID NO:28), or 5'-CACCCAGGTTCCTCCAGCATCTCCT-3' (SEQ ID NO:29) which are complementary to sequences 237–26, 314–339, 2229–2254, and 5583–5608, respectively, of bovine supervillin cDNA, or the corresponding sequences in the human supervillin cDNA.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, and can be single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA*, 86:6553, 1989; Lemaitre et al., *Proc. Natl. Acad. Sci. USA*, 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques*, 6:958, 1988), or intercalating agents (see, for example, Zon, *Pharm. Res.*, 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide can include at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N2-carboxypropl) uracil, (acp3)w, and 2,6-diaminopurine.

The antisense oligonucleotide can also include at least one modified sugar moiety selected from the group including, but not limited to, arabinose, 2-fluoroarabinose, xylulose, and hexose.

The antisense oligonucleotide can further include at least one modified phosphate backbone, such as a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In another alternative form, the antisense oligonucleotide can be an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.*, 15:6625, 1987). The oligonucleotide is a 2'-0-methylribonucleotide (Inoue et al., *Nucl. Acids Res.*, 15:6131, 1987), or a chimeric RNA-DNA analog (Inoue et al., *FEBS Lett.*, 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (*Nucl. Acids Res.*, 16:3209, 1988), and methylphosphonate oligonucleotides can be prepared by use of controlled pore glass polymer supports (Sarin et al., *Proc. Natl. Acad. Sci. USA*, 85:7448, 1988).

While antisense nucleotides complementary to the supervillin coding region sequence could be used, those complementary to the transcribed untranslated region are most preferred.

The antisense molecules should be delivered to cells that express supervillin in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

Recombinant DNA constructs in which the antisense oligonucleotide is placed under the control of a strong pol III or pol II promoter can be used to transfect target cells in the patient. This will result in the transcription of sufficient amounts of single stranded RNAs that will form complementary base pairs with the endogenous supervillin transcripts and thereby prevent translation of the supervillin mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., Nature, 290:304, 1981); the promoter contained in the 3' long terminal repeat of Rous sarcoma virus (Yamamoto et al., Cell, 22:787–797, 1988); the herpes thymidine kinase promoter (Wagner et al., Proc. Natl. Acad. Sci. USA, 78:1441, 1981); or the regulatory sequences of the metallothionein gene (Brinster et al., Nature, 296:39, 1988).

Ribozymes

Ribozyme molecules designed to catalytically cleave supervillin mRNA transcripts can be used to prevent translation of supervillin mRNA and expression of supervillin (see, e.g., PCT Publication WO 90/11364; Saraver et al., Science, 247:1222, 1990). While various ribozymes that cleave mRNA at site-specific recognition sequences can be used to destroy supervillin mRNAs, hammerhead ribozymes are particularly useful. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., Nature, 334:585, 1988). There are numerous examples of potential hammerhead ribozyme cleavage sites within the nucleotide sequence of human supervillin cDNA. Preferably, the ribozyme is engineered so that the cleavage recognition site is located near the 5' end of the supervillin mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena thermophila (known as the IVS or L-19 IVS RNA), and which has been extensively described by Cech and his collaborators (Zaug et al., Science, 224:574, 1984; Zaug et al., Science, 231:470, 1986; Zug et al., Nature, 324:429, 1986; PCT Application No. WO 88/04300; and Been et al., Cell, 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in supervillin.

As in the antisense approach, the ribozymes can be composed of modified oligonucleotides (e.g., for improved stability, targeting, etc.), and should be delivered to cells which express the supervillin in vivo. A preferred method of delivery involves using a DNA construct "encoding" the ribozyme under the control of a strong constitutive pol III or pol II promoter, so that transfected cells will produce sufficient quantities of the ribozyme to destroy endogenous supervillin messages and inhibit translation. Because ribozymes, unlike antisense molecules, are catalytic, a lower intracellular concentration is required for efficiency.

Other Methods for Reducing Supervillin Expression

Endogenous supervillin gene expression can also be reduced by inactivating or "knocking out" the supervillin gene or its promoter using targeted homologous recombination (see, e.g., U.S. Pat. No. 5,464,764). For example, a mutant, non-functional supervillin (or a completely unrelated DNA sequence) flanked by DNA homologous to the endogenous supervillin gene (either the coding regions or regulatory regions of the supervillin gene) can be used, with or without a selectable marker and/or a negative selectable marker, to transfect cells that express supervillin in vivo. Insertion of the DNA construct, via targeted homologous recombination, results in inactivation of the supervillin gene. Such approaches are particularly suited for use in the agricultural field where modifications to ES (embryonic stem) cells can be used to generate animal offspring with an inactive supervillin. This approach can be adapted for use in humans, provided the recombinant DNA constructs are directly administered or targeted to the required site in vivo using appropriate viral vectors.

Alternatively, endogenous supervillin gene expression can be reduced by targeting deoxyribonucleotide sequences complementary to the regulatory region of the supervillin gene (i.e., the supervillin promoter and/or enhancers) to form triple helical structures that prevent transcription of the supervillin gene in target cells in the body (Helene Anticancer Drug Res., 6:569, 1981; Helene et al., Ann. N.Y. Acad. Sci., 660:27, 1992; and Maher, Bioassays, 14:807, 1992).

Detecting Compounds Associated with Supervillin

The invention also features compounds, e.g., proteins, which interact with supervillin. Any method suitable for detecting protein-protein interactions may be employed for identifying transmembrane proteins, intracellular, or extracellular proteins that interact with supervillin. Among the traditional methods which may be employed are co-immunoprecipitation, crosslinking and co-purification through gradients or chromatographic columns of cell lysates, or proteins obtained from cell lysates, and the use of supervillin to identify proteins in the lysate that interact with supervillin. For these assays, the supervillin polypetide can be a full length supervillin, a soluble extracellular domain of supervillin, or some other suitable supervillin polypeptide. Once isolated, such an interacting protein can be identified and cloned and then used, in conjunction with standard techniques, to identify proteins with which it interacts. For example, at least a portion of the amino acid sequence of a protein which interacts with the supervillin can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and "PCR Protocols: A Guide to Methods and Applications," Innis et al., eds. Academic Press, Inc., NY, 1990).

Additionally, methods can be employed which result directly in the identification of genes which encode proteins that interact with supervillin. These methods include, for example, screening expression libraries, in a manner similar to the well known technique of antibody probing of λgt11 libraries, using labeled supervillin polypeptide or a supervillin fusion protein, e.g., a supervillin polypeptide or domain fused to a marker such as an enzyme, fluorescent dye, a luminescent protein, or to an IgFc domain.

There are also methods which are capable of detecting protein interaction. One method that detects protein interactions in vivo is the two-hybrid system (Chien et al., *Proc. Natl. Acad. Sci. USA,* 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding supervillin, a supervillin polypeptide, or a supervillin fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or LacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, supervillin may be used as the bait gene product. Total genomic or cDNA sequences are fused to the DNA encoding an activation domain. This library and a plasmid encoding a hybrid of bait supervillin gene product fused to the DNA-binding domain are cotransformed into a yeast reporter strain, and the resulting transformants are screened for those that express the reporter gene. For example, a bait supervillin gene sequence, such as supervillin or a domain of supervillin can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait supervillin gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait supervillin gene-GAL4 fusion plasmid into a yeast strain which contains a lacZ gene driven by a promoter which contains GAL4 activation sequence. A cDNA encoded protein, fused to GAL4 transcriptional activation domain, that interacts with bait supervillin gene product will reconstitute an active GAL4 protein and thereby drive expression of the HIS3 gene. Colonies which express HIS3 can then be purified from these strains, and used to produce and isolate the bait supervillin gene-interacting protein using techniques routinely practiced in the art.

Effective Doses

Toxicity and therapeutic efficacy of the polypeptides of the invention and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include an $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma can be measured, for example, by high performance liquid chromatography.

Formulations and Use

Pharmaceutical compositions for use in accordance with the present invention can be formulated in a conventional manner using one or more physiologically acceptable carriers or excipients.

Thus, the compounds and their physiologically acceptable salts and solvates can be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds can be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides.

In addition to the formulations described previously, the compounds can also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, ophthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

Agents affecting supervillin expression can be administered in combination with other therapeutic regimens, e.g., treatments with ionizing radiation and chemotherapeutic agents. Suitable diseases or conditions for use of supervillin include any hyperproliferative disease associated with an increase in supervillin expression or function relative to its expression in normal tissue, e.g., carcinomas or non-malignant hyperproliferative epithelial disorders.

Similarly, agents that increase supervillin expression can be used to treat conditions associated with a decrease in supervillin expression or function relative to normal tissues.

EXAMPLES

The invention will be further described in the following examples, which do not limit the scope of the invention described in the claims. The following examples illustrate the characterization of bovine and human supervillin nucleic acids and polypeptides.

Example 1
Primary Structure of Bovine Supervillin Nucleic Acids and Polypeptides As detected by blot overlays with $^{125}$I-labeled F-actin (an assay described in Chia et al., *J. Cell Biol.,* 120:190, 1993), a polypeptide with an apparent molecular mass of 205,000 daltons (p205) was detected as a major actin-binding protein in a bovine neutrophil membrane fraction (Pestonjamasp et al., *Mol. Biol. Cell,* 6:247, 1995).

To determine if p205 represented a novel protein, p205 protein was isolated from plasma membranes, and its partial peptide sequence was determined. This partial peptide sequence information was then used to isolate complete cDNAs encoding the p205 protein which, for reasons to be explained below, has been named supervillin. Another protein, afadin, that binds F-actin, contains a plasma membrane-binding domain, and also has a molecular weight of about 205,000 daltons, has been described (Mandai et al., *J. Cell Biol.,* 139:517, 1997); however, its sequence is distinct from supervillin.

To isolate supervillin protein in sufficient amounts for partial peptide sequencing, plasma membranes (160 mg) from bovine neutrophils at a concentration of 1 mg/ml were extracted for 60 minutes at 0° C. with TEB (1% TRITON™ X-100, 250 mM NaCl, 2.5 mM MgATP, 2 mM EGTA, 0.3 mM aprotonin, 2 μM leupeptin, 3 μM pepstatin, 1 mM PMSF, and 25 mM Tris-HCL, pH7.4). After centrifugation at 141,000×g for 60 min, the pellet was solubilized by sonication for 1 minutes at 0° C. (bath sonicator) in 10 ml of 4% SDS, 0.1 mM DTT, 10 mM Tris-HCl, pH 7.5, and heated for 10 minutes at 70° C. The suspension was clarified by centrifugation at 240,000×g for 30 minutes and concentrated to 3 ml in a Centricon-100 microconcentrator (Amicon, Beverly, Mass.). High molecular weight polypeptides were resolved by electrophoresis into a ~15 cm-long 5% SDS-polyacrylamide gel. When a visible myosin standard (Amersham) had migrated to ~10 cm, the proteins were electrotransferred onto a PVDF membrane (Millipore, Bedford, Mass.) and visualized by staining with Ponceau S. The band just under myosin, which corresponded to supervillin, was excised, washed extensively with sterile water, and digested with either sequencing-grade TPCK-trypsin (Promega, Madison, Wis.) or Endo-LysC (Promega). Peptides were purified on a microbore HPLC and sequenced.

Microsequencing of the band corresponding to supervillin generated a total of 8 peptide sequences, which are shown in Table I.

TABLE I

| | |
|---|---|
| SPVELDEDFDVIFDPYAPR (pepA) | (SEQ ID NO: 5) |
| MVP<u>R</u>PQTTAG<u>D</u>VLDGVNVGR (pepB) | (SEQ ID NO: 6) |
| YGSFEEAELSYPVLSR | (SEQ ID NO: 7) |
| (K)MLAAREDLLQEYT | (SEQ ID NO: 8) |
| VREGDNHKEAIYA | (SEQ ID NO: 9) |
| YQTQPVT | (SEQ ID NO: 10) |
| LF<u>R</u>EMEK | (SEQ ID NO: 11) |

The placement of the lysine residue indicated in parentheses is inferred based on the cleavage specificity of the endopeptidase (Endo-LysC) used to generate the peptide.

Underlined sequences are those which differ from the amino acids encoded by the full-length bovine supervillin cDNA (SEQ ID NO:4) (see below).

The sequence of the cDNA encoding supervillin was determined from a series of overlapping PCR and PCR-RACE reaction products that spanned the length of the gene.

Degenerate oligonucleotide primers (5'-CCIGTIGARYTIGAYGARGA-3' (SEQ ID NO:12) and 5'-CKIGGIGCRTAIGGRTCRAA-3' (SEQ ID NO:13) corresponding to 20 base pairs at each end of the supervillin peptide A microsequence were used with ADVANTAGE KLENTAQ™ DNA polymerase (Clontech, Palo Alto, Calif.) in an OMN-E CYCLER™, Hybaid Limited, Long Island, N.Y.) to amplify a 53-base pair product from MDBK cDNA. The cDNA was prepared using the MARATHON™ cDNA Amplification Kit (Clontech, Palo Alto, Calif.), and mRNA was made with the POLYATRACT mRNA Isolation System IV (Promega) from total RNA prepared using TRI™ Reagent (Molecular Research Center, Cincinnati, Ohio). Products were cloned into the pGEM-T vector (Promega), and propagated in JM-109 chemically competent cells (Promega). Plasmid with insert was purified by boiling minipreps (Ausubel et al., "Current Protocols in Molecular Biology, Vol. I," Green Publishing Associates, Inc., and John Wiley & Sons, Inc., N.Y., 1989), digested with PstI/AatII, and sequenced (Sequenase Version 2.0, Amersham), yielding the non-degenerate central nucleotides of the MDBK peptide A sequence.

A degenerate oligonucleotide primer (5'-AGTTNGATGAGGATTTCGATGTCATTTTYGAYCC-3' (SEQ ID NO:14)) and the Clontech Marathon Adaptor Primer 1 (AP1) (5'-CCATCCTAATACGACTCACTATAGGGC-3' (SEQ ID NO: 30)) were used with KLENTAQ™ enzyme mix in touchdown PCR program #1 (Clontech) to generate a 3-kb 3'-RACE product from the ds cDNA template. Correct clones were identified by digestion with PstI/AatII; sequencing verified the presence of known codons downstream of the primer.

Primers designed from 3'-RACE products were used in two sequential rounds of 5'-RACE reactions with the Clontech AP1 primer and Klentaq enzyme mix to generate overlapping clones corresponding to the full-length cDNA encoding supervillin. Gene-specific primers used in these reactions were:
5'-CTCGCGGCCAGCATCTTCAGGG-3' (SEQ ID NO:15),
5'-GATCTTCCCTCGCGGCCAGCATCTTCAGGG-3 (SEQ ID NO:16),
5'-TCAAACGACTTCTCCATCTCCCTGAAGAGC-3' (SEQ ID NO:17), or
5'-GTCAGGTTCTCCCTGCTCAGCAGAATCTTT-3' (SEQ ID NO:18). Reaction products were cloned into pGEM-T, and colonies were screened using a modification of a standard protocol (Sambrook et al., "Molecular Cloning, A Laboratory Manual," 2nd Ed. Cold Spring Harbor Laboratory Press, Cold Spring Harbor, N.Y., 1989). Briefly, nitrocellulose filters were placed onto plates containing 100–300 medium-sized colonies (1.0 mm in diameter) for 30 seconds, and holes were punched for alignment. Filters were denatured, neutralized, washed, air dried, stacked individually between sheets of aluminum foil, autoclaved (3 minutes sterilize, 3 minutes dry), and screened with end-labeled oligonucleotides corresponding to sequences upstream of the gene-specific primer (Ausubel et al., "Current Protocols in Molecular Biology, Vol. I," Green Publishing Associates, Inc., and John Wiley & Sons, Inc., NY, 1989).

Non-degenerate oligonucleotide primers (5'-GAGCCAGGTCAACTTCAAATTCAGAAATG-3' (SEQ ID NO:19) and 5'-TATTAAGGTAGAAAGGTGGATTCGCACAGA-3' (SEQ ID NO:20)) and the Expand Long Template PCR System (Boehringer Mannheim) were used in a PCR reaction with first-strand MDBK cDNA. The cDNA was prepared with the SUPERSCRIPT PREAMPLIFICATION SYSTEM™ for first strand cDNA Synthesis (Gibco BRL) from mRNA prepared using the Poly(A)Pure mRNA Isolation Kit (Ambion, Austin, Tex.). The 5198-base pair product was ligated into pGEM-T and completely sequenced.

Full-length and deletion constructs generated from internal AatII and PstI restriction sites were sequenced in both directions. For each nucleotide, 4 to 9 independently-generated cDNAs were sequenced in both directions.

Predicted secondary structure was determined using the PeptideStructure subroutine in the Genetics Computer Group, Inc. (Madison, Wis.) sequence analysis software package. Percent identity and homology were assessed using the GAP and PileUp subroutines in this same package. GAP was used for individual, optimized sequence comparisons and PileUp for multiple sequence alignments. The consensus DNA sequence is shown in FIGS. 9A–C. This DNA encodes a protein of 1792 amino acids beginning at nucleotide 201 with the amino acid sequence shown in FIG. 1. The amino acid sequence starting with the first methionine of the translated open reading frame includes all 8 peptides (shown as double underlines). The amino terminal half of the supervillin polypeptide contains four putative nuclear targeting signals (grey boxes), the longest of which resembles the nucleoplasmin targeting signal (underlined). The carboxy terminal portion of the polypeptide contains a potential tyrosine phosphorylation site (black). Amino acids are indicated by the numbers in the left margin.

The predicted molecular weight of 200,626 (pI ~6.44) (Bjellqvist et al., Electrophoresis, 14:1023, 1993) is in good agreement with that predicted for supervillin by SDS-PAGE. Relative to an "average" protein (Creighton, "Proteins: Structures and Molecular Principles," W. H. Freeman & Co., NY, 1983), supervillin is high in arginine (7.1% vs. 4.7%) and glutamine (9.2% vs. 6.2%) and low in tyrosine (2.3% vs. 3.5%) and cysteine (1.3% vs. 2.8%), variations that are consistent with its relative insensitivity to staining by silver.

Analysis of the deduced amino acid sequence suggests that supervillin is a bipartite protein with distinctly different amino and carboxy terminal domains. These domains are shown schematically in FIG. 2. Putative nuclear targeting regions are shown in the grey boxes and potential protein kinase A phosphorylation sites are indicated with asterisks. The carboxy terminal domain (cross-hatched) shows extensive similarity to villin and gelsolin, with three regions of especially high homology that correspond to potential F-actin binding sites (black boxes). The potential tyrosine phosphorylation site is indicated (•).

The amino terminal half (first ~935 amino acids) contains numerous charge clusters in the context of a primarily alpha-helical secondary structure. One 17-residue motif and three short clusters of positively-charged amino acids fit the consensus sequences for, respectively, nucleoplasmin- and SV40-like nuclear targeting signals (Chelsky et al., *Mol. Cell Biol.*, 9:2487, 1989; Robbins, *Cell*, 64:615, 1991). Because the nucleoplasmin targeting signal is found in 56% of all nuclear proteins but only ~4% of non-nuclear proteins (Dingwall et al., *TIBS*, 16:478, 1991) and because nuclear localization signals are additive (Garcia-Bustos et al., *Biochim. Biophys. Acta.*, 1071:83, 1991), the PSORT protein localization prediction program (Nakai et al., *Genomics*, 14:897, 1992) indicates a 96.4% probability that supervillin partitions into the nucleus. Hence, an analysis of the supervillin primary sequence supports the immunocytological observation of anti-pepA signal within the nuclei of subconfluent cells.

Sequence analysis also suggests a potential mechanism for the regulation of supervillin accumulation in the nucleus. The putative nuclear localization signals are surrounded by 43 serines and threonines that are potentially phosphorylatable by protein kinase A (FIG. 2 asterisks), protein kinase C, and/or casein kinase II. Thus, targeting of supervillin to the nucleus could be regulated by Ser/Thr phosphorylation, a mechanism documented for other proteins that conditionally localize to the nucleus (Garcia-Bustos et al., *Biochim. Biophys. Acta.*, 1071:83, 1991). By contrast, the carboxy-terminal half of supervillin contains only 24 potentially phosphorylatable serines and threonines. This domain does, however, contain a consensus site for tyrosine phosphorylation (Tyr-1157; FIG. 1, black box, FIG. 2, black dot), a protein modification known to regulate adherens junction structure (Anderson et al., *Amer. J. Physiol.*, 269:G467, 1995).

Figure 3:
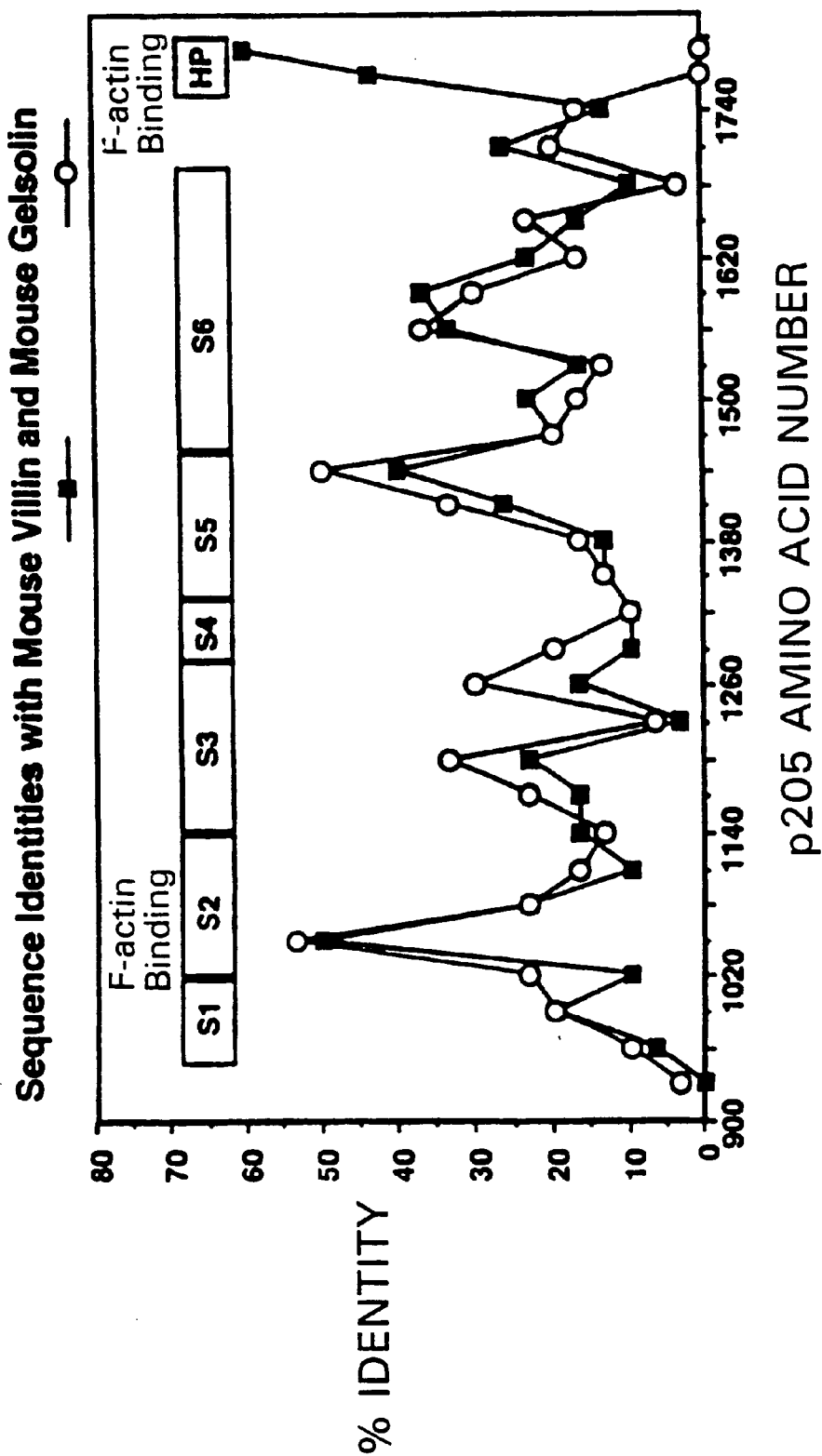
FIG. 3 is a graph showing regions of identity between the carboxy terminus of bovine supervillin and mouse villin (--O--) and gelsolin (--■--) proteins.

As shown in FIG. 3, the supervillin protein has extensive homology with the villin/gelsolin family of cytosolic F-actin binding proteins. The percentage of identical residues in every consecutive 30-amino acid segment of supervillin were plotted versus the number of the last residue in the segment. The locations of the gelsolin and villin homology segments (S1–S6), and the villin headpiece domain (HP) are drawn to scale.

Many short stretches of sequence similarity were identified by the BLASTP search algorithm (Altschul et al., *J. Mol. Biol.*, 215:403, 1990) between sequential segments of supervillin, starting at about Asn-979, through virtually the entire lengths of villin and gelsolin (FIG. 3). In individual, optimized comparisons of each of these sequences with that of the carboxy terminus of supervillin, the overall percent identities were 29% (villin) and 28% (gelsolin), and the overall similarities were 48% and 50%, respectively.

The nature of the similarity with villin and gelsolin is best appreciated when the percent identities are plotted as a function of position along the length of supervillin (FIG. 3). Regions of very high sequence identity are interspersed with regions exhibiting little or no similarity, usually due to the presence of additional residues in supervillin (SEQ ID NO:4). In particular, this analysis identified three localized regions of ~50% sequence identity between supervillin (SEQ NO:4) and sites in villin and/or gelsolin (FIG. 3). Two of these sites include sequences that have been previously shown to bind F-actin (Weeds et al., *Curr. Opin. Cell Biol.*, 5:63, 1993). The first site, amino acids 1023–1032 in supervillin (SEQ ID NO:4), is very similar to a sequence found in the segment-2 region of both gelsolin and villin that, when dimerized, can crosslink actin filaments (de Arruda et al., *J. Biol. Chem.*, 267:13079, 1992). The second of these sites is the carboxy terminus of supervillin, which is extremely similar to the carboxy terminal "headpiece" region of villin, a sequence involved in bundling actin filaments in vitro (Glenney et al., *Proc. Natl. Acad. Sci. USA*, 78:2810, 1981; Janmey et al., *J. Biol. Chem.*, 263:16738, 1988) and in vivo (Franck et al., *J. Cell Biol.*, 111:2475, 1990). Interestingly, most of the amino acids that are conserved between the chick and mouse villin headpieces are also found in the supervillin polypeptide of SEQ ID NO:4, suggesting that this region of supervillin also may bind F-actin.

The third region of high sequence similarity between supervillin, gelsolin, and villin corresponds to carboxy-terminal residues in segment-5 of the latter two proteins (FIG. 2).

Proteolytic fragments (Bryan, *J. Cell Biol.*, 106:1553, 1988) and bacterially-expressed proteins (Way et al., *J. Cell Biol.*, 109:593, 1989) containing segments 4 through 6 of gelsolin contain an otherwise-unmapped Ca2+-dependent site for binding F-actin. It is thus possible that this third region of high homology to villin and gelsolin also corresponds to a sequence that can bind Factin. In any case, this segment-5 homology region in supervillin, as well as many of the other peaks of sequence identity shown in FIG. 3, apparently represents an important structural or functional site common to all three of these proteins.

Other proteins exhibiting high structural similarity with supervillin are protovillin, a ~100-kDa F-actin capping protein from *Dictyostelium discoideum*, and an open reading frame in the *C. elegans* genome that is predicted to encode a ~113-kDa protein. Optimized alignments along the length of each protein indicate that protovillin is 27% identical (49% similar) and that the *C. elegans* ORF is 25% identical (46% similar) to the supervillin carboxy-terminus. More distant relationships with other members of the villin/gelsolin superfamily, including adseverin, scinderin, severin, and fragmin (Weeds et al., *Curr. Opin. Cell Biol.*, 5:63, 1993), also were observed. Thus, at ~200,000 daltons, supervillin is the largest member of the villin/gelsolin superfamily, hence the name "supervillin."

Example 2

Isolation and Characterization of Human Supervillin cDNA Sequences

Degenerate primers based on the bovine supervillin sequence were used to clone human supervillin cDNA from HeLa cells using PCR, and 5'-RACE PCR.

A degenerate primer having the sequence 5'-GATGAGGATTTCGATGTCATTTTYGATCTT-3' (SEQ ID NO:21) and the primer HumR1 5'-GGCTCCAGACCAGCGTGGATAAGGTAAGA-3' (SEQ ID NO:22) were used to generate a PCR product of 2.5 kb. Sequences within this PCR product were then used to design primers having the sequences 5'-TAGAAAAGCAAACTCGATCCAAATACTGCA-3' (SEQ ID NO:23) and 5'-GGAGGTTTCTGTGCAGTATTTGGATCGAGTT-3' (SEQ ID NO:24). These primers generated a 6.0 kb PCR product encoding all of human supervillin except its extreme 5' end.

The 5' end was isolated with PCR reactions using the HU5PGAP primer 5'-GACCTGTCCTGCAGACGGGGTAAGC CTC-3' (SEQ ID NO:25) and the Clontech AP1 primer 5'-CCATCCTAATACGACTCACTATAGGGC-3' (SEQ ID NO:30).

All primers used for the cloning of human supervillin were from IDT (Coralville, Iowa), with the exception of the AP1 primer, which was obtained from Clontech. All PCR reactions were performed on first strand HeLa cDNA, with the exception of the 5'RACE reaction which was performed on the same cDNA, but with Clontech Marathon Adaptors ligated at the 5' and 3' ends.

Figures 4, 4A, 4B, 4C, 4D, 5, 5A, 5B:
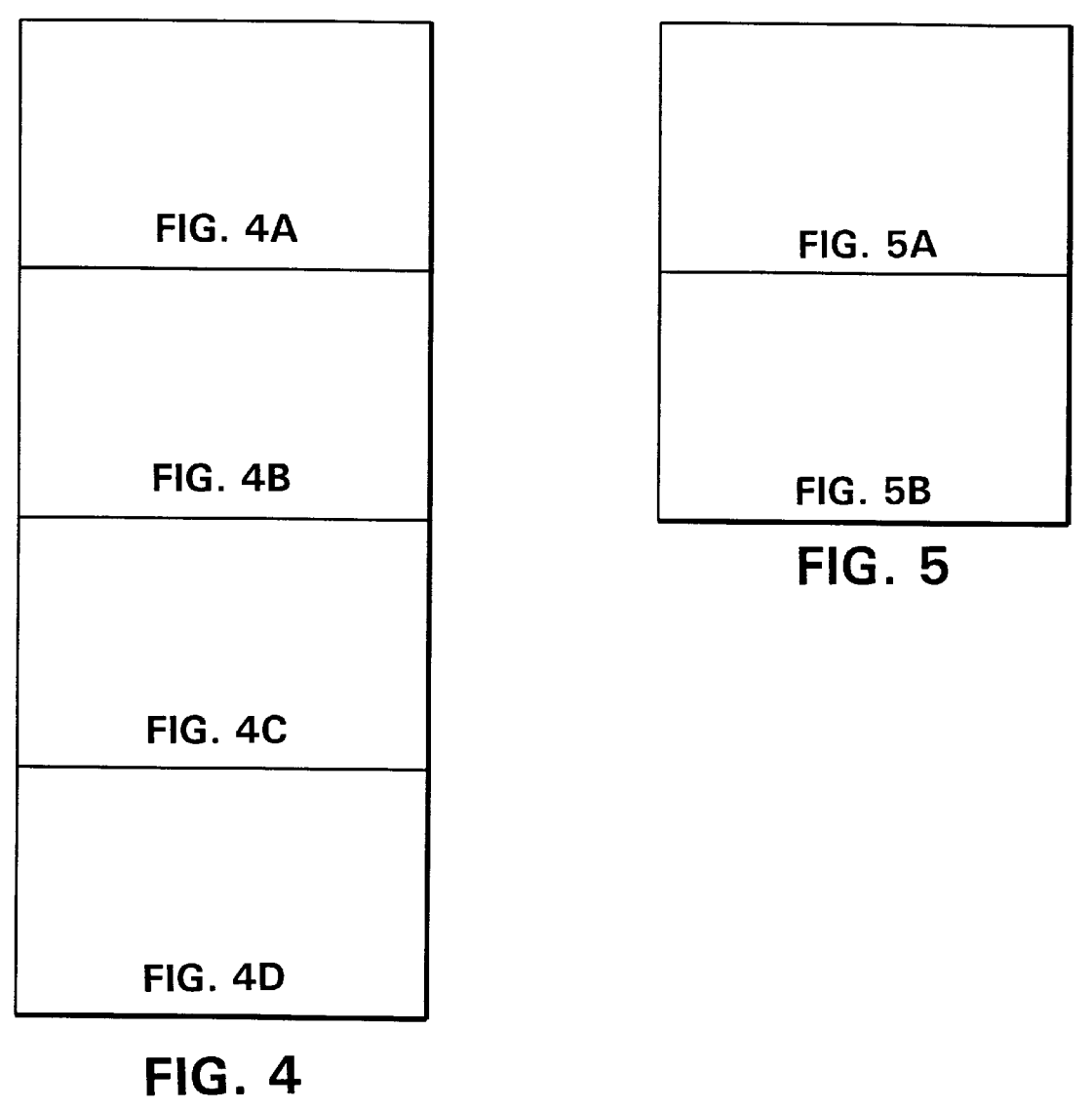
Figure 4C:
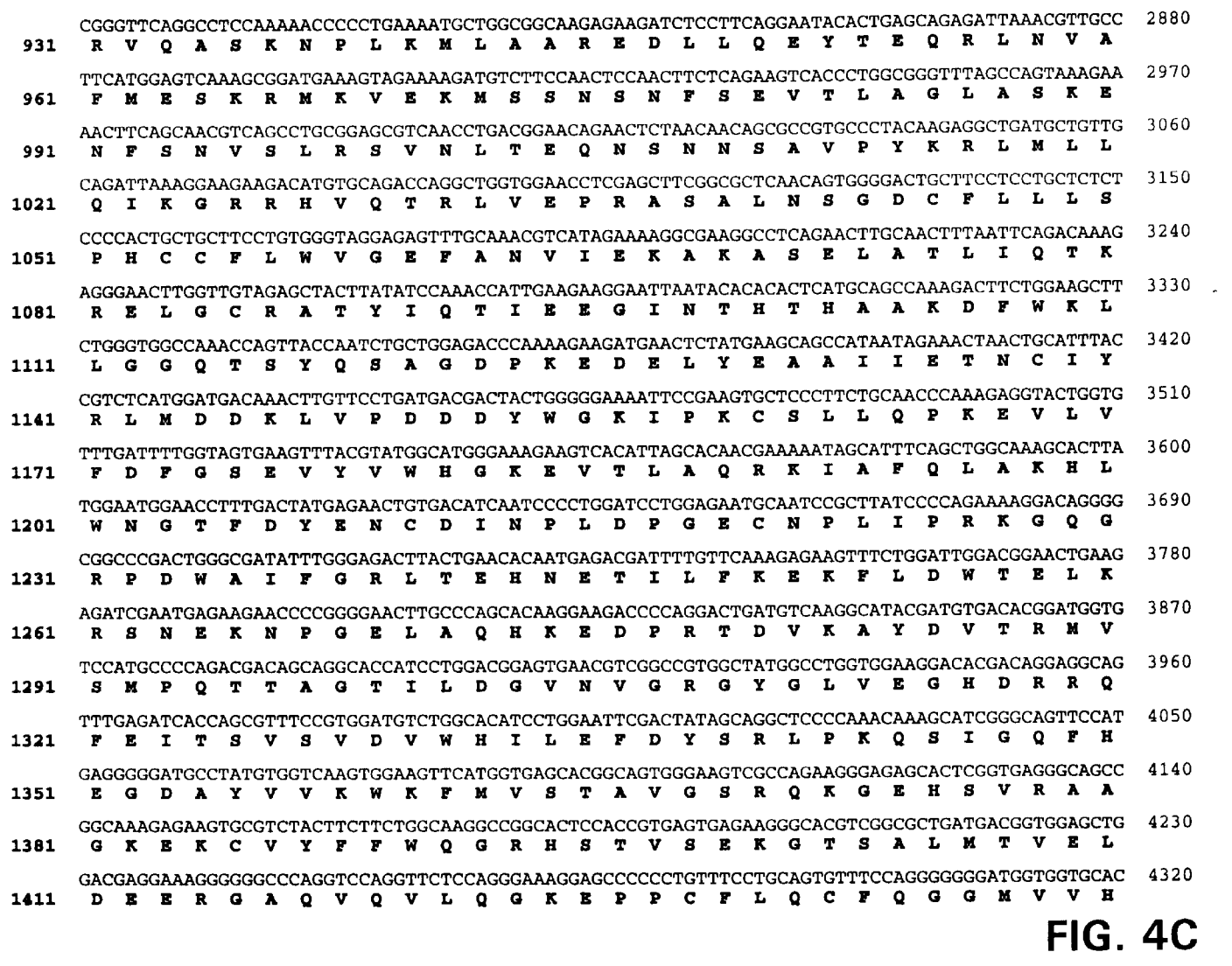

The nucleotide sequence of the human cDNA sequence (SEQ ID NO:1), along with its predicted encoded amino acid sequence (SEQ ID NO:2), is shown in FIG. 4.

Figure 6:
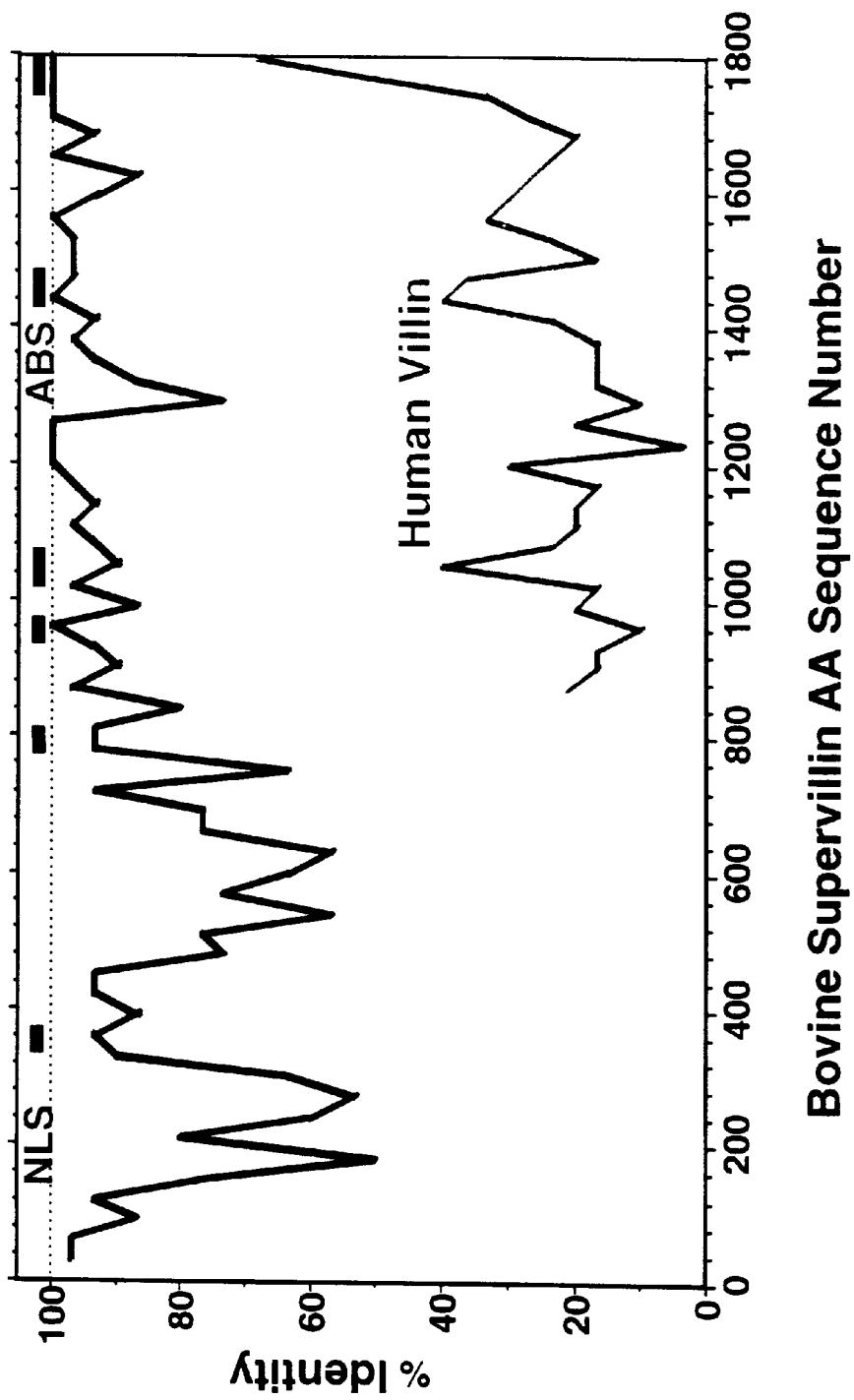
FIG. 6 is a graph comparing regions of identity between the amino acid sequences of bovine supervillin, human supervillin, and human villin.

The bovine and human supervillin amino acid sequences are compared in FIGS. 5 and 6. As demonstrated in FIG. 6, human and bovine supervillin have extensive conservation, especially in the villin-like carboxy terminus. The human sequence contains all three of the potential actin-binding sites and three of the four nuclear localization signals found in the bovine sequence. Overall, the supervillin N-terminus is conserved between cows and humans, with 72.9% identity at the amino acid level. The carboxy terminus is even more highly conserved, with 91.5% amino acid identity and 100% conservation of the villin-like headpiece.

Using nick translated, fluorescently labeled probes, the human supervillin gene was localized to the short arm of chromosome 10, at 10.p11.2. This region contains a breakpoint for chromosomal rearrangements associated with adult T-cell leukemia and acute myelocytic leukemia.

Example 3
Generation of Antibodies to Supervillin-Derived Peptides

Antibodies against the two longest peptides (pepA (SEQ ID NO:5) and pepB (SEQ ID NO:6)) described in Example 1 were used to specifically immunoprecipitate supervillin from neutrophil membrane extracts. Polyclonal antisera were generated against synthetic peptides pepA, SPVELD-EDFDVIFDPYAPR (SEQ ID NO:5) and pepB, VPRPQT-TAGDVLDGVN (SEQ ID NO:6), which correspond to the two longest sequences derived from partial peptide sequencing of the supervillin protein. Anti-peptide antibodies were produced against each peptide after conjugation to keyhole limpet hemocyanin. ELISA titers (Harlow et al., "Antibodies," A Laboratory Manual. Cold Spring Harbor Laboratory, Cold Spring Harbor, N.J., 1988) of antibodies directed against peptide A ranged from 108,600 to 300,000; titers of antibodies against peptide B ranged from 4,300 to 6,700.

Antibodies were affinity purified against the cystinyl aminocaproic acid derivative of the appropriate peptide conjugated to immobilized chicken egg white lysozyme (Ingalls, "Developmentally-regulated changes in *Dictyostelium discoideum* plasma membrane protein composition and actin-binding activity," Princeton University, 1989). IgG was purified by ammonium sulfate precipitation and DE52 chromatography (Hudson et al., "Practical Immunology." Blackwell Scientific Publications, Boston, 156–202, 1980) and was incubated overnight at 4° C. with the appropriate affinity matrix. After extensive washes with PBS (150 mM NaCl, 10 mM sodium phosphate buffer, pH 7.5) and with 0.5 M NaCl, 10 mM Tris-HCl, pH 7.6, high affinity anti-peptide antibodies were eluted with 3.5 M $MgCl_2$, 50 mM Tris-HCl, pH 7.2. These antibodies were immediately diluted with 1 mg/ml BSA, 10 mM Tris-HCl, pH 7.6, dialyzed against 150 mM NaCl, 10 mM Tris-HCl, pH 7.6, and concentrated and stored at −20° C. in this buffer containing 50% glycerol.

Antisera against either peptide (generated in each of 4 rabbits) specifically immunoprecipitated supervillin from SDS- and heat-denatured membrane extracts. Specificity was indicated by the absence of supervillin from immunoprecipitates generated with preimmune sera or with immune sera in the presence of the appropriate peptide antigen. Similar results were obtained with the corresponding affinity-purified antibodies. Thus, both pepA and pepB are derived from supervillin.

Example 4
Characterization of Supervillin's Interaction with the Plasma Membrane Supervillin was first identified in the g fraction of plasma membranes (Pestonjamasp et al., *Mol. Biol. Cell*, 6:247, 1995). The g fraction contains both large sheets of plasma membrane and "secretory vesicles," which are intracellular vesicles of similar density and composition that are believed to represent mobilizable intracellular stores of plasma membrane proteins involved in cell adhesion and other activation-associated surface processes.

To characterize supervillin and its interaction with the plasma membrane, the g fraction was separated into two membrane populations using a modified Percoll gradient as described in (Dahlgren et al., *Biochem. J.*, 311:667, 1995). Neutrophils were isolated from 8 to 16 liters of fresh bovine blood by differential lysis followed by fractionation on preformed gradients of isotonic Percoll (Pharmacia LKB Biotechnology, Piscataway, N.J.) and were disrupted by nitrogen cavitation (Del Buono et al., *J. Cell. Physiol.*, 141:636, 1989). Plasma membranes, secretory vesicles, pooled granules, and cytosol were separated by flotation of the postnuclear supernatant on a step Percoll gradient (Dahlgren et al., *Biochem. J.*, 311:667, 1995).

Briefly, cavitates were centrifuged to remove nuclei and mixed with an equal volume of a 1.12 g/ml Percoll solution in relaxation buffer (Pestonjamasp et al., *Mol. Biol. Cell*, 6:247, 1995). Gradients consisted of 5 ml of 1.12 g/ml Percoll in relaxation buffer, 14 ml of the cavitate/Percoll mixture, 14 ml of a 1.04 g/ml Percoll suspension in relaxation buffer, and 5 ml of relaxation buffer. After centrifugation at 65,000×g for 20 minutes at 4° C., the plasma membrane fraction was collected from the top of the 1.04 g/ml Percoll layer. Secretory vesicles were harvested from the interface between the 1.04 g/ml Percoll layer and the layer that initially contained cavitate. Pooled granules were collected from the bottoms of the centrifuge tubes. "Cytosol" was defined as the supernatant obtained after centrifuging the cavitate-containing layer at 141,000×g for 2 hours at 4° C. The various membrane-containing fractions were centrifuged under the same conditions to remove Percoll, and the less dense organellar pellets were resuspended in relaxation buffer and stored in aliquots at −80° C.

Purity of the plasma membrane fraction was assessed by transmission electron microscopy. The plasma membrane, secretory vesicle, and granule fractions (0.5 ml each) were overlaid onto 2-ml cushions of 64% sucrose in relaxation buffer and centrifuged at 200,000×g for 30 minutes at 4° C. to remove Percoll. Membranes were collected from the tops of the sucrose cushions, diluted with relaxation buffer, and re-centrifuged into a tight pellet at 200,000×g for 15 minutes at 4° C. The pellets were fixed for 1 hour at 0° C. in 2.5% glutaraldehyde, 0.1 M sodium cacodylate, pH 7.4, washed three times with cacodylate buffer, and postfixed with 2% $OsO_4$, 0.1 M sodium cacodylate, pH 7.4. After three more washes with buffer, the pellets were stained en bloc with 0.5% aqueous uranyl acetate, dehydrated in ethanol/acetone, and embedded in EMBED 812—DER 736 (EMS, Ft. Washington, Pa.). Sections of ~65 nm were cut both parallel and perpendicular to the axis of centrifugation and post-stained with 5% aqueous uranyl acetate for 30 minutes and Reynolds' lead citrate for 30 seconds before visualization on a Philips EM 301 microscope at an accelerating voltage of 60 kV.

To examine the distribution of plasma membrane associated actin-binding proteins, nitrocellulose blots were probed for moesin, ezrin, and supervillin using $^{125}$I-labeled F-actin (Chia et al., *Cell Motil. Cytoskeleton.*, 18:164, 1991; Pestonjamasp et al., *Mol. Biol. Cell,* 6:247, 1995).

Other cytoskeletal proteins were visualized with either monoclonal antibodies (β-actin) or polyclonal antibodies (fodrin, myosin II, fodrin). Antibodies against β-actin and nonmuscle myosin II were obtained from Sigma Chemical Company (St. Louis, Mo.) and Biomedical Technologies Inc. (Stoughton, Mass.), respectively. Polyclonal antibodies were visualized with 0.1 μCi/ml $^{125}$I-labeled protein A (Dupont NEN, Wilmington, Del.). Antibody against β-actin was visualized by incubating blots either with 0.25 μg/ml $^{125}$I-labeled goat anti-mouse IgG (Amersham, Searle Corp., Arlington Heights, Ill.) or with 5 μg/ml rabbit anti-mouse IgG (Pierce Chemical Co., Rockford, Ill.), followed by incubation with $^{125}$I-labeled protein A. After exposure to film, relative amounts of labeled protein were quantified with a scanning densitometer (PDI, Huntington Station, N.Y.).

The less dense fraction (density <1.04) was enriched in large membrane sheets with associated amorphous filamentous structures and corresponds to the peak of surface-exposed alkaline phosphatase. Thus, the less dense fraction appeared to be mostly plasma membrane. The denser fraction (density between 1.04–1.06) corresponds to the peak of latent alkaline phosphatase and contains predominantly small osmophilic vesicles. These vesicles probably represent secretory vesicles although some mitochondria are also observed in this fraction. While large amounts of all three major F-actin binding proteins (supervillin, ezrin, moesin) were found in the plasma membrane fraction, the enrichment was greatest for supervillin since ezrin and moesin also were present in the secretory vesicle and cytosolic fractions. As reported previously (Pestonjamasp et al., *Mol. Biol. Cell,* 6:247, 1995), none of these F-actin binding proteins was observed in the pooled granule fraction. There was at least 20 times more supervillin in the plasma membrane fraction than in the secretory vesicle fraction, and 10 to 15 times more than in cytosol. This large enrichment suggests an intimate association of supervillin with the plasma membrane.

To explore the nature of the interaction between supervillin and the plasma membrane, the purified neutrophil plasma membranes were extracted with a series of salt and detergent solutions. Detergent extractions were carried out at 0° C. for 60 minutes with either 1% TRITON™ X-100, 3% octylglucoside, or 0.1% SDS in 1 mM EGTA, 2.5 mM MgATP, 0.3 M aprotinin, 2 μM leupeptin, 3 μM pepstatin, 1 mM PMSF, 25 mM Tris-HCl, pH 7.5, and either 50, 150, or 250 mM NaCl. As a positive control, membranes were extracted at 70° C. for 10 minutes with 1% SDS. Supernatants and pellets were collected after centrifugation at 200,000×g for 60 minutes.

For extraction with salt or alkali, plasma membranes were suspended in 20 mM sodium phosphate, pH 7.5, containing 1 mM EDTA, 1 mM DTT, and the above-mentioned protease inhibitors. Membranes were extracted at 0° C. for 60 minutes with either 2.5 mM MgATP, 0.25M KCl, 1.0 M KCl or for 10 minutes in 0.1 M sodium carbonate or 0.1 M NaOH. Supernatants and pellets were collected after centrifugation at 200,000×g for 60 minutes through a 10% sucrose cushion prepared in the above buffer. Samples were denatured for 10 minutes at 70° C. in Laemmli sample buffer before analysis on SDS-PAGE (Laemmli, *Nature (Lond.),* 227:680, 1970).

Buffers containing 2.5 mM MgATP, a reagent that extracts most of the similarly-sized myosin II, had no effect on the membrane association of supervillin. Similarly, moderately high salt concentrations (0.25 M) that extract significant amounts of membrane-bound moesin and ezrin, had no detectable effect on the extractability of supervillin. Even sodium carbonate, a reagent that extracts many peripherally-bound proteins (Hubbard et al., *J. Cell Biol.*, 96:230, 1983), had no effect on the membrane association of supervillin. On the other hand, supervillin was partially extracted at salt concentrations >1 M and was almost completely extracted by 0.1 M NaOH, indicating that supervillin is a tightly-bound peripheral protein, and not an integral component, of the plasma membrane.

In agreement with this assessment, supervillin also was resistant to extraction by a number of nonionic detergents. At salt concentrations up to 250 mM, supervillin remained insoluble in the presence of 1% TRITON™ X-100, 3% octylglucoside, or 0.1% SDS. The only detergent that effectively solubilized supervillin was 1% SDS. A large fraction of the membrane-associated β-actin was retained in the supervillin-enriched pellet after extraction with buffers containing 250 mM NaCl and either 1% TRITON™ X-100 or 3% octylglucoside, conditions that extracted essentially all moesin and ezrin. Thus, both supervillin and β-actin appear to be detergent-resistant components of a membrane skeleton that does not require either moesin or ezrin for at least some of its integrity.

The inextractability of supervillin under conditions that solubilized most membrane and membrane skeleton proteins, in conjunction with the large amounts of plasma membrane obtainable from bovine neutrophils, suggested that this protein should be readily purified by differential extraction followed by preparative SDS-PAGE. Plasma membranes were thus extracted with a buffer containing 1% TRITON™ X-100, 0.25 M NaCl, and 1 mM MgATP to identify proteins that are tightly associated with the neutrophil plasma membrane skeleton. The inclusion of MgATP in this buffer resulted in the removal of most of the myosin II that migrated near supervillin on SDS-gels. When run on a long 5% polyacrylamide gel, there was a clear separation of supervillin from residual myosin and other similarly-sized membrane skeleton proteins.

Example 5

Characterization of Supervillin's Association with Actin Filaments in Vivo

To further characterize the nature of supervillin's association with actin filaments in vivo, the phalloidin shift assay originally described by Carraway and colleagues (Carraway et al., *Exp. Cell Res.*, 161:150, 1985) was used to determine whether supervillin and endogenous β-actin sedimented together in the same detergent- and salt-resistant complex. In this approach, membranes are extracted with a TRITON™-containing buffer in the presence and absence of 10 μM phalloidin. Microfilament-associated proteins are those that exhibit increased S values when sedimented in the presence of stabilized (plus phalloidin) vs. destabilized (no phalloidin) actin filaments.

Plasma membranes (1 mg/ml), in the presence or absence of 10 μM phalloidin (Boehringer Mannheim GmbH, Mannheim, Germany), were extracted for 1 hour at 0° C. with TRITON™ extraction buffer (TEB): 1% TRITON™ X-100, 250 mM NaCl, 2.5 mM MgATP, 2 mM EGTA, 0.3 mM aprotinin, 2 μM leupeptin, 3 μM pepstatin, 1 mM PMSF, 25 mM Tris-HCl, pH 7.4. Samples (0.8 ml) were centrifuged at 200,000×g for 16 hours at 4° C. into 20–55% linear sucrose gradients (3.6 ml) over a 64% sucrose cushion (0.5 ml). Fractions (0.3 ml) were collected from the top of the gradient with a density gradient fractionator (ISCO, Lincoln, Nebr.) and analyzed for the presence of cytoskeletal proteins after SDS-polyacrylamide gel electrophoresis and electrotransferred to nitrocellulose (Towbin et al., *Proc. Natl. Acad. Sci. U.S.A.*, 76:4350, 1979). Calibration standards and accepted values (Sober, "Handbook of Biochemistry," Second Edition. The Chemical Rubber Co., Cleveland, Ohio, 1970) for Svedberg coefficients (×1013) were: b-amylase (9 S), bovine thyroglobulin (19 S), and *E. coli* small ribosomal subunit (30 S). Changes in the distribution of supervillin were assessed by quantification of bound $^{125}$I-labeled F-actin on overlays as described below.

For these experiments, a buffer containing relatively high concentrations of TRITON™ X-100 (1%), NaCl (250 mM), and MgATP (2.5 mM) was used in order to depolymerize significant amounts of the total actin and to dissociate most membrane skeleton proteins. As expected for an F-actin binding protein, supervillin extracted from neutrophil plasma membranes exhibited a reproducible phalloidin-induced increase in S value. In the presence of phalloidin, supervillin sedimented as a component of a ~30S complex that also contained the bulk of the membrane-associated β-actin. Although variable amounts of a ~13S moiety were observed in two experiments, most supervillin sedimented as a ~26S complex in the absence of phalloidin. Surprisingly, although much of the β-actin was rendered monomeric by the harsh buffer conditions, significant amounts continued to sediment with high S values in the absence of phalloidin stabilization. In contrast to the behavior of supervillin and β-actin, little or no fodrin, myosin, ezrin, or moesin exhibited significant phalloidin-induced shifts in sedimentability under these conditions.

More evidence for the association of supervillin with β-actin in situ was obtained by demonstrating that supervillin and F-actin co-sediment in reciprocal immunoprecipitation assays.

For most experiments, supervillin was immunoprecipitated with antibodies against peptide A, but some experiments also employed antibodies against peptide B. To show that both peptides originated from supervillin, membranes (6 mg) were extracted with TEB, solubilized with 1% SDS (0.6 ml) at 70° C. for 10 minutes and diluted 10 fold with RIPA buffer (150 mM NaCl, 1% NP-40, 0.5% sodium deoxycholate, 0.1% SDS, 50 mM Tris-HCl pH 8.0) lacking SDS to generate a final concentration of 0.1% SDS. The suspension was clarified by centrifugation at 200,000×g for 30 minutes, preadsorbed for 3 hours at 4° C. with nonspecific rabbit IgG bound to protein A-agarose beads (BioRad) (Firestone et al., *Meth. Enzymol.*, 182:688, 1990), and centrifuged for 30 seconds at 100×g. Supervillin was precipitated from 0.5 ml aliquots of the supernatant by overnight incubation at 4° C. with antisera and protein A agarose beads. Controls employed either preimmune sera or immune sera in the presence of the appropriate competing peptide (66.6 mg/ml). Proteins bound to the agarose beads were sedimented through 1 M sucrose in RIPA buffer and solubilized with Laemmli sample buffer.

To demonstrate co-immunoprecipitation of actin with supervillin, neutrophil plasma membranes (1.0 mg/ml) were solubilized for 1 hour at 0° C. with TEB, preadsorbed, and clarified, as described above. Clarified suspensions (0.25 ml) were incubated overnight at 4° C. with protein A-agarose beads containing 150 mg of either affinity-purified antibodies against peptide A or non specific rabbit IgG. The beads were centrifuged for 3 minutes at 200×g through 1 M sucrose in TEB and washed three times with the high-stringency RIPA buffer before solubilization for analysis by SDS-PAGE.

To demonstrate co-precipitation of supervillin with actin, plasma membranes were treated briefly at 0° C. with either fluorescein-phalloidin (Molecular Probes, Eugene, Oreg.) or unlabeled phalloidin (Boehringer Mannheim) at a ratio of 1 mg of phalloidin per mg of membrane protein. Membranes (1 mg/ml) were extracted for 1 hour at 0° C. with TEB, preabsorbed, and clarified, as above. Clarified suspensions (0.45 ml) were incubated overnight at 4° C. with protein A-agarose beads and 400 mg of either purified anti-fluorescein IgG (Luna et al., *J. Biol. Chem.*, 257:13095, 1982) or nonspecific IgG. This amount of anti-fluorescein IgG is approximately equimolar to the amount of phalloidin bound to membrane actin. Beads were centrifuged through 1 M sucrose in TEB and solubilized in Laemmli sample buffer.

High-affinity polyclonal antibodies against fluorescein (Luna et al., *J. Biol. Chem.*, 257:13095, 1982; Voss, "Fluorescein Hapten: An Immunological Probe," CRC Press, Inc., Boca Raton, Fla., 193 pages, 1984) were also used to pellet actin filaments stabilized with fluorescein-labeled phalloidin. Neutrophil plasma membranes were incubated with fluorescein-phalloidin, and then phalloidin-bound actin filaments were precipitated from detergent-solubilized extracts with anti-fluorescein. Essentially all of the supervillin in the initial extract co-precipitated with F-actin bound to fluorescein-phalloidin, whereas little or no supervillin was found in control experiments with nonspecific IgG or with unlabeled phalloidin.

In converse experiments, β-actin co-pelleted with supervillin immunoprecipitated with affinity-purified antibodies against pepA. Less than 5% as much β-actin co-precipitated with equivalent amounts of nonspecific IgG under these conditions.

The phalloidin shift experiments and the co-immunoprecipitation assays suggest that the direct association between supervillin and rabbit α-actin observed on F-actin blot overlays also occurs between supervillin and β-actin on the neutrophil plasma membrane. Thus, supervillin apparently forms large complexes with endogenous β-actin under conditions that suggest an extremely tight association, direct or indirect, in the neutrophil membrane skeleton.

Example 6

Distribution of Supervillin Gene Products in Various Cell and Tissue Types

The distribution of supervillin in diverse cell types was examined using immunoblot analyses with affinity-purified antibodies against supervillin, and in northern blot hybridization analyses using supervillin probes.

Cells were grown with 10% FBS unless otherwise specified. MDBK cells were grown in MEM with Earls balanced salts; SHSY5Y human neuroblastoma cells in RPMI medium 1640; NIH-3T3 cells and COS-7 monkey kidney cells in Dulbecco's modified eagle medium; pig kidney epithelial cells (LLC-PK1) in Medium 199 with 3% FBS; NRK cells in F-12 nutrient mixture; HeLa-S3 cells (available from the American Type Culture Collection, Bethesda, Md. as ATCC NO. CCL-2.2) in Joklik MEM with 5% FBS (Irvine Scientific, Santa Ana, Calif.). Reagents for tissue culture were purchased from Gibco BRL (Grand Island, N.Y.).

Both human cervical carcinoma cells and bovine kidney epithelial cells contained at least as much supervillin as bovine neutrophils. Also, the anti-pepA antibody was highly specific for supervillin in these tissue culture cells since they lacked an immunocrossreactive ~90 kDa protein found in neutrophil granules. Other transformed and non-transformed cell lines also contained a 205-kDa band recognized by both affinity-purified anti-pepA antibodies and $^{125}$I-labeled F-actin. For instance, supervillin was present in neuroblastoma SHSY5Y cells, in 3T3 fibroblasts, and in a number of epithelial cell lines. Although the pepA antibodies appeared to be specific for supervillin in these cells, a second polypeptide with a slightly slower mobility was observed in F-actin blot overlays of 3T3 mouse and normal rat kidney cells. Thus, while supervillin is a major actin-binding protein in many cell types, it is not the only protein in this size range that can be visualized by $^{125}$I-labeled F-actin on blot overlays.

Figure 7:
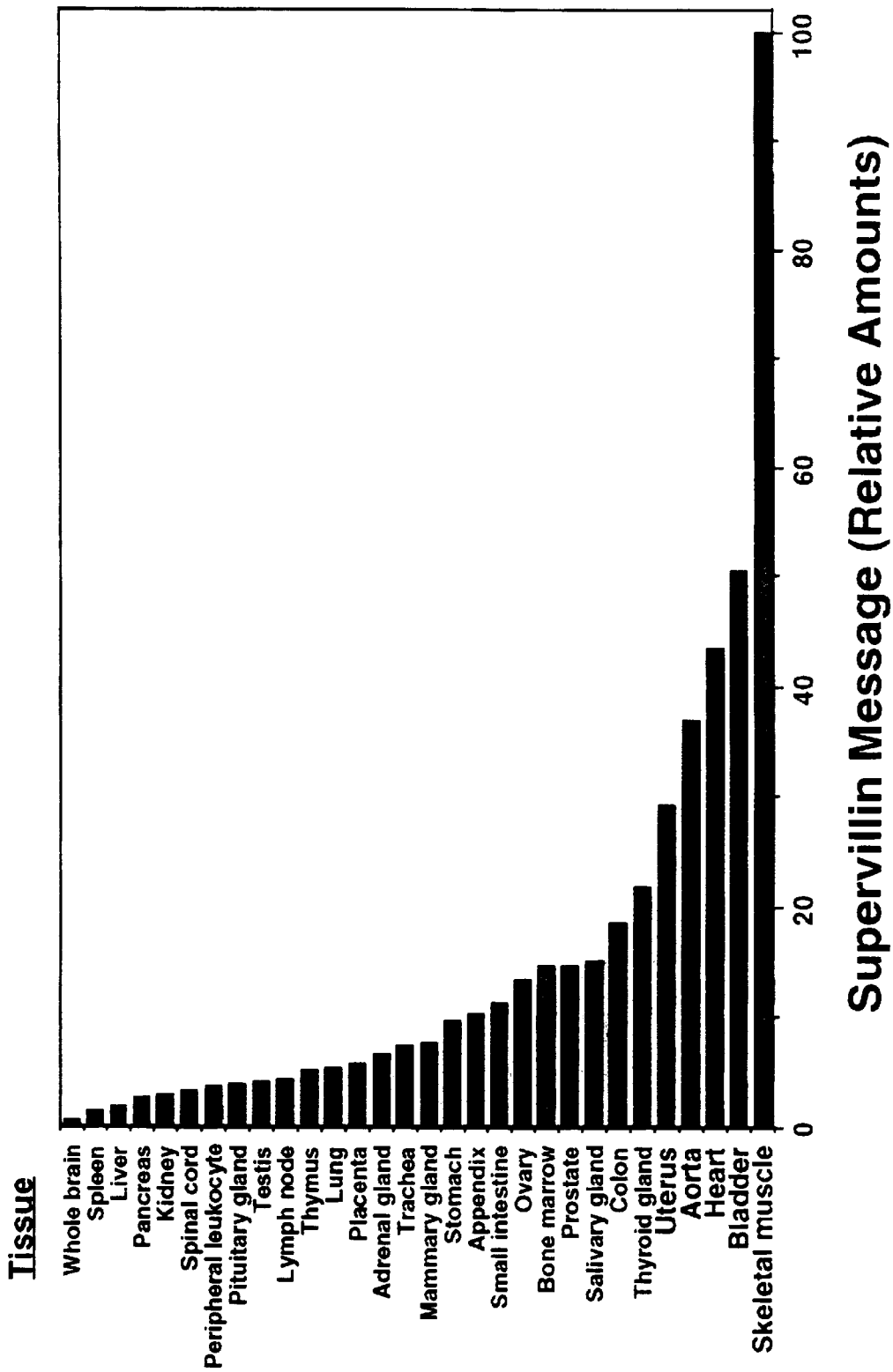
FIG. 7 is a histogram showing the relative abundance of supervillin mRNA in various tissues.

These studies were complemented by studies examining the presence of supervillin RNA sequences in various cell types. A blot of human RNA isolated from various tissues (HUMAN RNA MASTER BLOT™ (Clontech, Palo Alto, Calif.), on which loading of RNA had been normalized, was probed for the presence of supervillin mRNA. FIG. 7 illustrates the relative amount of supervillin message in various body tissues and organs.

Supervillin RNAs were detected in all human tissues tested, and were most abundant in muscle, bone marrow, thyroid gland, and salivary gland. Comparatively little message is found in the brain. Supervillin transcripts of two distinct sizes were identified. Muscle supervillin mRNA is about 8.4 kb in size, while the message size in most tissues and cell lines is about 7.4 kb.

Supervillin RNA levels were examined in a variety of cancer cell lines. Relatively high levels of the 7.4 kb supervillin message was detected in HeLa cervical carcinoma cell line S3, colorectal adenocarcinoma cell line SW480, and lung carcinoma cell line A549. Lower levels of supervillin transcripts were detected in melanoma cell line G361, promyelocytic leukemia cell line HL-60 and lymphoblastic leukemia cell line MOLT-4. Little or no message was detected in chronic myelogenous leukemia cell line K-562 and Burkitt's lymphoma cell line Ragi.

Example 7
Intracellular Localization of Supervillin

Immunofluorescence was used to determine the site or sites within the cell at which supervillin gene products localized.

Confluent or subconfluent MDBK cells grown on coverslips were washed twice in PBS and fixed for 20 minutes at room temperature with PBS containing 1% EM grade formaldehyde (EMS). EGTA-treated cells were washed with Dulbecco's-PBS (138 mM NaCl, 2.7 mM KCl, 8.1 mM Na2HPO4, 1.2 mM KH2PO4, pH 7.0) and incubated at 37° C. with 3 mM EGTA in the same buffer for 10, 20, and 30 minutes before fixation. After three washes with PBS, the fixed cells were permeabilized with 1% TRITON™ X-100 in PBS for 1 minute at room temperature and then washed three more times. The coverslips were blocked with 10% horse serum, 1% BSA, and 0.02% sodium azide in PBS for ~2 hours at room temperature or overnight at 4° C. Coverslips were then incubated for 2 to 4 hours at 37° C. with either a monoclonal pan-cadherin antibody (Sigma) diluted 1:1000 in blocking solution, and/or affinity-purified antibodies against supervillin peptide A at 150 μg/ml in blocking solution. After three washes in PBS, coverslips were incubated with a 1:750 dilution of Texas Red-labeled goat anti-rabbit IgG (Cappel, Durham, N.C.) and/or a 1:1000 dilution of Oregon Green-labeled goat anti-mouse IgG (Molecular Probes) for 1 hour at room temperature. In some experiments, the secondary antibody solution also contained 10 units/ml Bodipy-phallicidin (Molecular Probes).

At these antibody concentrations, no significant background was observed in the absence of primary antibody, and no bleed-through fluorescence was detected in samples labeled singly with either primary antibody. After the final washes, samples were mounted with Slowfade-Light Antifade Medium (Molecular Probes) and observed using a BioRad MRC 1024 confocal microscope (Hercules, Calif.) equipped with LaserSharp Version 2.1A software.

To explore further the extent of the association between supervillin and cadherin-containing junctional complexes, confluent monolayers of MDBK cells were treated with 3 mM EGTA, which induces the release of intercellular contacts and a coordinate internalization of vesicles containing E-cadherin and bound junctional proteins (Kartenbeck et al., J. Cell Biol., 113:881, 1991). At early times after treatment with EGTA, supervillin co-localized with ring-like structures of bundled actin filaments and E-cadherin during their contraction into the cytoplasm away from the membrane (Kartenbeck et al., J. Cell Biol., 113:881, 1991; Volberg et al., J. Cell Biol., 102:1832, 1986). At later times after EGTA-mediated cell-cell dissociation, supervillin and E-cadherin continued to co-localize in fragmented bar-like structures near the nucleus. As these structures broke down with time (Kartenbeck et al., J. Cell Biol., 113:881, 1991; Volberg et al., J. Cell Biol., 102:1832, 1986), supervillin became dissociated into cytoplasmic punctae that no longer co-localized significantly with the large juxtanuclear structures containing cadherin. However, supervillin and cadherin continued to co-localize at sites of residual cell-cell contact. No significant intranuclear staining for either supervillin or cadherin was observed at any time after addition of EGTA.

These results indicate an extensive association, direct or indirect, between E-cadherin and supervillin in adherens-like junctions and suggest that supervillin also can reside in a separate, punctate cytoplasmic compartment, e.g., on vesicles. These observations further suggest that the nuclear signal observed in subconfluent cells may represent yet another supervillin-containing intracellular compartment.

Several lines of evidence suggest supervillin is associated with plasma membranes in HeLa and MDBK cells. First, supervillin was enriched approximately ten fold, about the same fold enrichment as a biotin cell surface marker, in crude plasma membrane fractions (Atkinson, Meth. Cell Biol., 7:157, 1973) from both cell types (see also Example 1, supra). Second, immunofluorescence localization with affinity-purified anti-pepA antibodies showed labeling of plasma membranes in both low density and confluent cells. While low density cells also contained appreciable amounts of signal in punctate dots throughout the cytoplasm and within the nucleus, most of the supervillin in confluent MDBK cells was localized at lateral cell borders. Double labeling with antibodies against E-cadherin showed colocalization with supervillin at sites of both initial and established cell-cell contact. This close association of supervillin and E-cadherin suggests that supervillin may be involved in the formation or stabilization of adherens-type junctions in epithelial cells.

Example 8
Inhibition of Supervillin Gene Expression

To determine if disruption of supervillin expression was associated with a cellular phenotype, antisense phosphorpothiorate oligonucleotides shown in Table II were synthesized and transfected into MDBK cells.

TABLE II

Antisense Phosphorothioate DNAs Directed Against Bovine Supervillin

| Name | Complementary Sequences in Bovine Supervillin cDNA | DNA Sequence |
| --- | --- | --- |
| SV-1 | 237–262 | 5'-TGGGCTGCGTGTCGGTTTCAATTCC-3' (SEQ ID NO: 26) |
| SV-2 | 314–339 | 5'-TGTGGCACGCATGTATCTGGGTGTG-3' (SEQ ID NO: 27) |
| SV-3 | 2229–2254 | 5'-CTCCAGCAGCAAACATCGCACACGG-3' (SEQ ID NO: 28) |
| SV-4 | 5583–5608 | 5'-CACCCAGGTTCCTCCAGCATCTCCT-3' (SEQ ID NO: 29) |

(Start ATG = 201)

Subconfluent MDBK cells were treated for four hours separately with each of the four 0.2 μM phosphorothioate supervillin antisense oligonucleotides (α-SV) or with 0.2 μM of a control oligonucleotide which was the "reversemer" of SEQ ID NO:3, i.e., 5'-GGCACACGCTACAAACGACGACCTC-3' (SEQ ID NO:31). Treated cells were grown in MEM with serum, then fixed, stained to reveal nuclei, and counted.

Figure 8A:
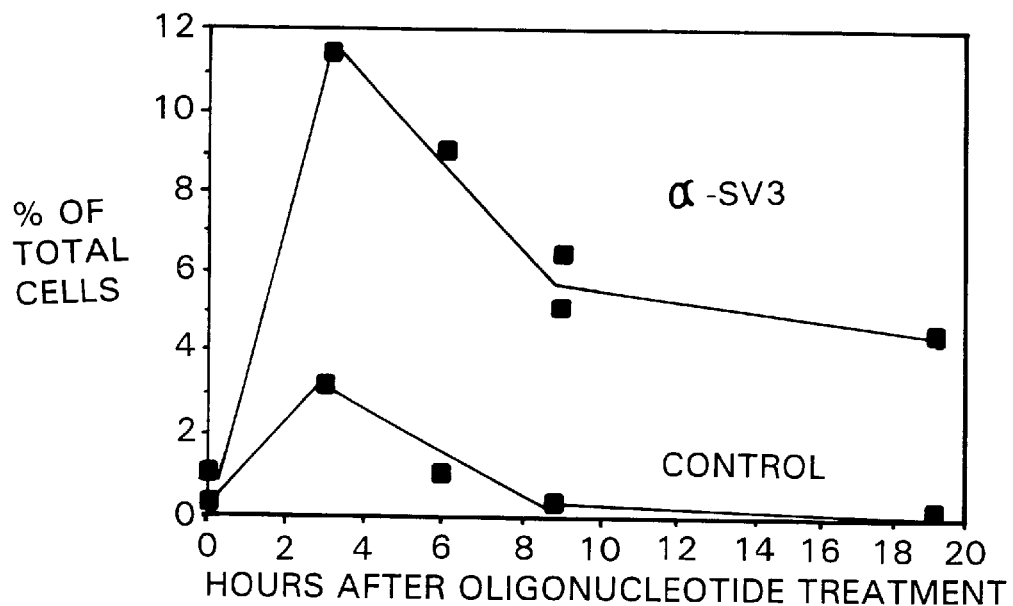
FIGS. 8A and 8B are graphs showing the incidence of apoptosis in cells transfected with supervillin antisense oligonucleotide α-SV3 or control oligonucleotide (A) and the percentage of mitotic nuclei in cells transfected with supervillin antisense oligonucleotide α-SV3 or control oligonucleotide (B).
Figure 8B:
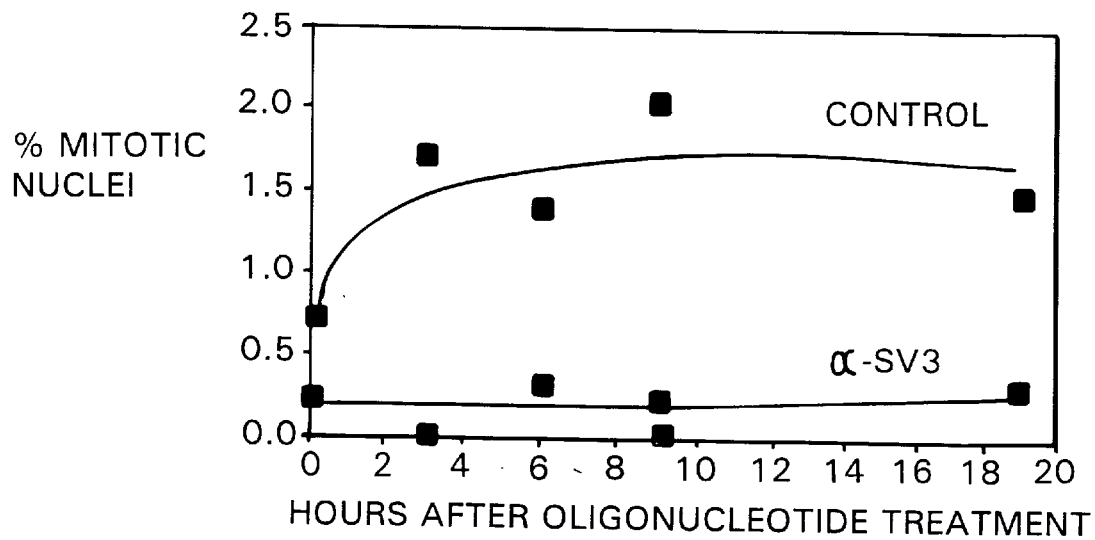

The results of a representative experiment are shown in FIG. 8A and FIG. 8B. FIG. 8A reveals that apoptosis begins within hours in a higher percentage of cells treated with the α-SV3 antisense oligonucleotide relative to a control oligonucleotide. FIG. 8B indicates that fewer of the α-SV3 treated cells entered mitosis relative to control cells. The oligonucleotides α-SV1, α-SV2, and α-SV4 similarly inhibited cell growth. These results suggest that the biological function of supervillin is to block apoptosis in sub-confluent epithelial cells.

Example 9
Diagnostic Assays Utilizing Supervillin Hybridization Probes

As described above, a nucleic acid probe containing some or all of the supervillin-encoding sequences of the invention (e.g., SEQ ID NO:1 or SEQ ID NO: 3) is used to detect supervillin mRNA in a sample of epithelial cells (e.g., a tissue section) suspected of being malignant. The probe used would be a single-stranded DNA or RNA (preferably DNA) antisense to the supervillin coding sequence. It is produced by synthetic or recombinant DNA methods, and labelled with a radioactive tracer or other standard detecting means. The probe includes from 15 up to the full supervillin coding sequence, and preferably is at least 30 nucleotides long. The assay is carried out by standard methods of in situ hybridization or Northern analysis, using stringent hybridization conditions. Control hybridization assays are run in parallel using normal epithelial cells or tissue sections from the same type of tissue as the test sample, and/or cells from a known carcinoma or carcinoma-derived cell line, or a cancer-containing tissue section. Cells which exhibit a substantially increased level of hybridization to the probe, compared to the level seen with normal epithelial cells, are likely to be malignant. The amount of hybridization is quantitated by standard methods, such as counting the grains of radioactivity-exposed emulsion on an in situ hybridization assay of a biopsy slide, or by densitometric scan of a Northern blot X-ray film. Alternatively, comparison of the test assay results with the results of the control assays is relative rather than quantitative, particularly where the difference in levels of hybridization is dramatic. This assay is useful for detecting malignant cells in epithelial tissue.

Example 10
Diagnostic Assays Utilizing Supervillin Antibodies

Antibodies specific for supervillin are generated by standard polyclonal or monoclonal methods, using as immunogen a purified, naturally-occurring supervillin; recombinant supervillin; or any antigenic fragment of supervillin (e.g., the pepA or pepp peptides described above) which induces antibodies that react with naturally-occurring supervillin. The latter fragment can be produced by synthetic or recombinant methods, or by proteolytic digestion of supervillin. If desired, the antigenic fragment is linked by standard methods to a molecule which increases the immunogenicity of the fragment, such as keyhole limpet hemocyanin (as described above). The polyclonal or monoclonal antibodies so produced are screened using purified recombinant or naturally occurring supervillin, or as described above, to select those which form an immunocomplex with supervillin specifically.

The antibodies so produced are employed in diagnostic methods for detecting cells, tissues, or biological fluids in which the presence of supervillin is increased relative to normal cells, an indication that the patient has a carcinoma. The sample tested may be a fixed section of a tissue biopsy, a preparation of cells obtained from a suspect tissue, or a sample of biological fluid, such as blood, serum, urine, sweat, tears, cerebrospinal fluid, milk, ductal fluid, or semen. Standard methods of immunoassay may be used, including those described above as well as sandwich ELISA. If the tested cells express increased levels of supervillin protein in this assay relative to normal cells of the same tissue type, the tested cells are likely to represent a carcinoma.

Example 11
Screens For and Uses of Therapeutic Agents Based on their Interaction with Supervillin Carcinoma or other cells in which the endogenous supervillin gene is up-regulated are used as a screening tool to identify compounds or treatment strategies that reduce expression of the supervillin gene. These cells are constructed by transfection with vectors expressing supervillin under the control of a strong promoter.

The cells are treated in vitro with the candidate compounds, and the amount of supervillin expression is determined using either a hybridization assay (e.g., Northern analysis) or an immunoassay. If a given compound is found to inhibit supervillin expression in the carcinoma cells, it is then further tested to see whether treatment with the compound prevents carcinoma growth in vivo in an appropriate animal model. An appropriate animal model is a transgenic model constructed using the techniques described above in which a supervillin gene is expressed under the control of an inducible promoter.

A compound effective both in inhibiting supervillin expression and in preventing carcinoma growth is a potential therapeutic useful for the treatment of carcinomas in which supervillin expression is increased compared to normal cells. Further evaluation of the clinical usefulness of such a compound follows standard methods of evaluating toxicity and clinical effectiveness of anticancer agents.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule encoding a supervillin polypeptide which binds actin, said molecule comprising a nucleotide sequence encoding a polypeptide having a sequence that is at least 85% identical to SEQ ID No:2, wherein the percent identity is calculated using the Genetics Computer Group Sequence Analysis Software Package with the default parameters.

2. The nucleic acid molecule of claim 1, wherein said nucleotide sequence encodes a polypeptide that binds F-actin.

3. The nucleic acid molecule of claim 1, said molecule encoding the human supervillin of SEQ ID NO:2.

4. The isolated nucleic acid molecule of claim 1, said molecule comprising the nucleotide sequence from about location 451 to about location 5814 of SEQ ID NO:1.

5. The isolated nucleic acid molecule of claim 1, said molecule hybridizing under stringent conditions to a nucleic acid sequence complementary to a nucleic acid molecule comprising the sequence of nucleotides from location 451 to location 5814, inclusive, of SEQ ID NO:1.

6. The isolated nucleic acid molecule of claim 1, said molecule encoding a polypeptide comprising the amino acid sequence of SEQ ID NO:2, or an amino acid sequence comprising one or more conservative substitutions in the amino acid sequence of SEQ ID NO:2.

7. A nucleic acid vector comprising the nucleic acid molecule of claim 1.

8. The nucleic acid vector of claim 7, wherein said vector is an expression vector.

9. The vector of claim 7, further comprising a regulatory element operably linked to said nucleic acid molecule.

10. The vector of claim 7, wherein said vector is a plasmid.

11. The vector of claim 7, wherein said vector is a virus.

12. A host cell comprising the isolated nucleic acid molecule of claim 1.

13. An isolated nucleic acid molecule encoding a supervillin polypeptide which binds actin, said molecule comprising a nucleotide sequence encoding a polypeptide having a sequence that is at least 85% identical to the sequence of SEQ ID No:4, wherein the percent identity is calculated using the Genetics Computer Group Sequence Analysis Software Package with the default parameters.

14. The nucleic acid molecule of claim 8, said molecule encoding a polypeptide having the sequence of SEQ ID NO:4.

15. The isolated nucleic acid molecule of claim 13, said molecule comprising the nucleotide sequence of nucleotides from location 201 to location 5576 of SEQ ID NO:3.

16. The isolated nucleic acid molecule of claim 13, said molecule hybridizing under stringent conditions to a nucleic acid sequence complementary to a nucleic acid molecule comprising the sequence of nucleotides from location 201 to location 5454, inclusive, of SEQ ID NO:3.

* * * * *